United States Patent
Griswold-Prenner et al.

(10) Patent No.: US 10,400,018 B2
(45) Date of Patent: Sep. 3, 2019

(54) TAU PEPTIDES, ANTI-TAU ANTIBODIES, AND METHODS OF USE THEREOF

(71) Applicant: iPierian, Inc., South San Francisco, CA (US)

(72) Inventors: Irene Griswold-Prenner, Jackson, WY (US); Graham Parry, San Mateo, CA (US); Tony SangYoung Byun, Brisbane, CA (US)

(73) Assignee: iPierian, Inc., South San Francisco, CA (US)

( * ) Notice: Subject to any disclaimer, the term of this patent is extended or adjusted under 35 U.S.C. 154(b) by 0 days.

(21) Appl. No.: 15/117,268

(22) PCT Filed: Feb. 14, 2014

(86) PCT No.: PCT/US2014/016597
§ 371 (c)(1),
(2) Date: Aug. 8, 2016

(87) PCT Pub. No.: WO2015/122922
PCT Pub. Date: Aug. 20, 2015

(65) Prior Publication Data
US 2016/0347804 A1 Dec. 1, 2016

(51) Int. Cl.
C07K 16/18 (2006.01)
C07K 14/47 (2006.01)
A61K 39/00 (2006.01)
A61K 49/00 (2006.01)
G01N 33/577 (2006.01)
A61K 38/00 (2006.01)

(52) U.S. Cl.
CPC ...... *C07K 14/4711* (2013.01); *A61K 39/0007* (2013.01); *A61K 49/0004* (2013.01); *C07K 16/18* (2013.01); *G01N 33/577* (2013.01); *A61K 38/00* (2013.01); *A61K 2039/55505* (2013.01); *A61K 2039/575* (2013.01); *A61K 2039/6081* (2013.01); *C07K 2317/24* (2013.01); *C07K 2317/34* (2013.01); *C07K 2317/92* (2013.01); *G01N 2333/47* (2013.01); *G01N 2333/4709* (2013.01)

(58) Field of Classification Search
None
See application file for complete search history.

(56) References Cited

U.S. PATENT DOCUMENTS

| | | | |
|---|---|---|---|
| 5,492,812 A | 2/1996 | Vooheis | |
| 5,535,663 A | 7/1996 | Yamashita et al. | |
| 5,600,392 A | 2/1997 | Sakamoto et al. | |
| 5,666,808 A | 9/1997 | Yamashita et al. | |
| 5,733,734 A | 3/1998 | Trojanowski et al. | |
| 5,811,310 A | 9/1998 | Ghanbari et al. | |
| 5,843,779 A | 12/1998 | Vandermeeren et al. | |
| 5,861,257 A | 1/1999 | Vandermeeren et al. | |
| 6,008,024 A | 12/1999 | Vandermeeren et al. | |
| 6,010,913 A | 1/2000 | Vandermeeren et al. | |
| 6,121,003 A | 9/2000 | Vanmechelen et al. | |
| 6,232,437 B1 | 5/2001 | Vandermeeren et al. | |
| 6,238,892 B1 | 5/2001 | Mercken et al. | |
| 6,500,674 B1 | 12/2002 | Vandermeeren et al. | |
| 6,680,173 B2 | 1/2004 | Vanmechelen et al. | |
| 6,900,293 B2 | 5/2005 | Mercken et al. | |
| 7,387,879 B2 | 6/2008 | Vanmechelen et al. | |
| 7,427,392 B1 | 9/2008 | Seubert et al. | |
| 7,442,516 B2 * | 10/2008 | Ohno | C07K 16/18 435/7.1 |
| 7,446,180 B2 | 11/2008 | Novak | |
| 7,466,180 B2 | 12/2008 | Slawecki | |
| 8,012,936 B2 | 9/2011 | Sigurdsson et al. | |
| 8,163,873 B2 | 4/2012 | Mercken et al. | |
| 8,409,584 B2 | 4/2013 | Wisniewski et al. | |
| 8,926,974 B2 | 1/2015 | Griswold-Prenner et al. | |
| 8,980,270 B2 | 3/2015 | Griswold-Prenner et al. | |
| 8,980,271 B2 | 3/2015 | Griswold-Prenner et al. | |
| 9,051,367 B2 | 6/2015 | Griswold-Prenner et al. | |
| 9,447,180 B2 | 9/2016 | Griswold-Prenner et al. | |
| 9,567,395 B2 | 2/2017 | Griswold-Prenner et al. | |
| 9,777,058 B2 | 10/2017 | Griswold-Prenner et al. | |
| 10,040,847 B2 | 8/2018 | Griswold-Prenner et al. | |

(Continued)

FOREIGN PATENT DOCUMENTS

| | | |
|---|---|---|
| JP | 2010-530740 | 9/2010 |
| JP | 6290212 | 3/2018 |

(Continued)

OTHER PUBLICATIONS

Lin, Wen-Lang et al., "Filamentous Tau in Oligodendrocytes and Astrocytes of Transgenic Mice Expressing the Human Tau Isoform with the P301L Mutation," American Journal of Pathology, vol. 162(1):213-218 (2003).

Liu, Li et al., "Trans-Synaptic Spread of Tau Pathology in Vivo," PLoS One, vol. 7(2):e31302, doi: 10.1371/journal.bone.0031302, 9 pages (2012).

Meredith, Jere E. Jr. et al., "Characterization of Novel CSF Tau and ptau Biomarkers for Alzheimer's Disease," PLoS One, vol. 8(10):e76523, doi: 1031371/journal.pone.0076523, 14 pages (2013).

Meredith, Jere et al., "Novel Tau Fragments are Present in Human CSF," Alzheimer's Association International Conference, p. P276-P277, Poster Presentation No. P2-039, 2 pages (2012).

(Continued)

*Primary Examiner* — Sergio Coffa
(74) *Attorney, Agent, or Firm* — Fish & Richardson P.C.

(57) ABSTRACT

Isolated tau peptides, and compositions comprising the peptides are disclosed. Further provided are antibodies specific for an isolated tau peptide. Methods of using the isolated tau peptide in diagnostic and treatment including using a pharmaceutical composition comprising the isolated tau peptide for stimulating an immune response in an individual to a tau peptide, and methods of using antibodies in detection, diagnosis, and treatment of disorders including a tauopathy are further provided.

32 Claims, 23 Drawing Sheets
Specification includes a Sequence Listing.

(56) References Cited

U.S. PATENT DOCUMENTS

| | | |
|---|---|---|
| 2001/0018191 A1 | 8/2001 | Mercken et al. |
| 2002/0001857 A1 | 1/2002 | Vandermeeren et al. |
| 2002/0019016 A1 | 2/2002 | Vanmechelen et al. |
| 2003/0138972 A1 | 7/2003 | Vandermeeren et al. |
| 2003/0143760 A1 | 7/2003 | Vandermeeren et al. |
| 2003/0147811 A1 | 8/2003 | Wisniewski et al. |
| 2003/0194742 A1 | 10/2003 | Vanmechelen et al. |
| 2004/0014142 A1 | 1/2004 | VanMechelen et al. |
| 2004/0038430 A1 | 2/2004 | Vandermeeren et al. |
| 2004/0072261 A1 | 4/2004 | Kostanjevecki et al. |
| 2004/0091942 A1 | 5/2004 | Vanmechelen et al. |
| 2004/0110250 A1 | 6/2004 | Wischik et al. |
| 2004/0265919 A1 | 12/2004 | Vanderstichele et al. |
| 2005/0014821 A1 | 1/2005 | Tsai et al. |
| 2005/0181460 A1 | 8/2005 | Ohno et al. |
| 2005/0191685 A1 | 9/2005 | Vanmechelen et al. |
| 2005/0196844 A1 | 9/2005 | Lee |
| 2005/0221391 A1 | 10/2005 | Davies |
| 2005/0255113 A1 | 11/2005 | Huston et al. |
| 2005/0260697 A1 | 11/2005 | Wang et al. |
| 2005/0261475 A1 | 11/2005 | Tseng et al. |
| 2006/0008853 A1 | 1/2006 | Mercken et al. |
| 2006/0122122 A1 | 6/2006 | Kobayashi et al. |
| 2006/0167227 A1 | 7/2006 | Kontsekova |
| 2007/0218491 A1 | 9/2007 | Vasan et al. |
| 2008/0050383 A1 | 2/2008 | Sigurdsson et al. |
| 2008/0057593 A1 | 3/2008 | Vanderstichele et al. |
| 2008/0213834 A1 | 9/2008 | Reed et al. |
| 2008/0220449 A1 | 9/2008 | Vasan et al. |
| 2008/0261889 A1 | 10/2008 | Vanmechelen et al. |
| 2009/0047675 A1 | 2/2009 | Roberts et al. |
| 2009/0137051 A1 | 5/2009 | Mercken et al. |
| 2009/0317805 A1 | 12/2009 | Wang et al. |
| 2010/0055722 A1 | 3/2010 | Nayak et al. |
| 2010/0063250 A1 | 3/2010 | Kontsekova |
| 2010/0284909 A1 | 11/2010 | Wisniewski et al. |
| 2010/0297108 A1 | 11/2010 | Henco et al. |
| 2010/0316564 A1 | 12/2010 | Sigurdsson |
| 2010/0323343 A1 | 12/2010 | Egan et al. |
| 2011/0027817 A1 | 2/2011 | Arancio et al. |
| 2011/0143380 A1 | 6/2011 | Holtzman et al. |
| 2011/0143443 A9 | 6/2011 | Mercken et al. |
| 2011/0177109 A1 | 7/2011 | Smith, III et al. |
| 2011/0201098 A1 | 8/2011 | Laureyn et al. |
| 2011/0250237 A1 | 10/2011 | O'Hagan et al. |
| 2011/0312059 A1 | 12/2011 | Moe et al. |
| 2011/0318358 A1 | 12/2011 | Sigurdsson et al. |
| 2012/0029169 A1 | 2/2012 | Moe et al. |
| 2012/0087861 A1 | 4/2012 | Nitsch et al. |
| 2012/0142602 A1* | 6/2012 | Brady ............... C07K 14/4711 514/17.7 |
| 2012/0183599 A1 | 7/2012 | Pfeifer et al. |
| 2012/0244146 A1 | 9/2012 | Chain |
| 2012/0244174 A1 | 9/2012 | Chain |
| 2012/0276009 A1 | 11/2012 | Pfeifer et al. |
| 2013/0028914 A1 | 1/2013 | Kayed |
| 2013/0156783 A1 | 6/2013 | Wisniewski et al. |
| 2013/0266514 A1 | 10/2013 | Nitsch et al. |
| 2013/0266585 A1 | 10/2013 | Nitsch et al. |
| 2013/0266586 A1 | 10/2013 | Nitsch et al. |
| 2013/0287838 A1 | 10/2013 | Hickman et al. |
| 2013/0288280 A1 | 10/2013 | Ladenson et al. |
| 2013/0295021 A1 | 11/2013 | Chen et al. |
| 2013/0310541 A1 | 11/2013 | Bohrmann et al. |
| 2014/0056901 A1 | 2/2014 | Agadjanyan et al. |
| 2014/0086921 A1 | 3/2014 | Griswold-Prenner et al. |
| 2014/0099303 A1 | 4/2014 | Griswold-Prenner et al. |
| 2014/0099304 A1 | 4/2014 | Griswold-Prenner et al. |
| 2014/0234214 A1 | 8/2014 | Griswold-Prenner et al. |
| 2014/0294831 A1 | 10/2014 | Griswold-Prenner et al. |
| 2015/0050281 A1 | 2/2015 | Griswold-Prenner et al. |
| 2015/0232544 A1 | 8/2015 | Griswold-Prenner et al. |
| 2015/0239963 A1 | 8/2015 | Griswold-Prenner et al. |
| 2016/0031978 A1 | 2/2016 | Brady et al. |
| 2016/0122421 A1 | 5/2016 | Griswold-Prenner et al. |
| 2016/0289309 A1 | 10/2016 | Griswold-Prenner et al. |
| 2016/0355578 A1 | 12/2016 | Griswold-Prenner et al. |
| 2017/0174755 A1 | 6/2017 | Griswold-Prenner et al. |

FOREIGN PATENT DOCUMENTS

| | | |
|---|---|---|
| WO | 9620218 A1 | 7/1996 |
| WO | 9822120 A1 | 5/1998 |
| WO | 0245743 A2 | 6/2002 |
| WO | 03014960 A2 | 2/2003 |
| WO | 2004007547 A2 | 1/2004 |
| WO | 2005010044 A2 | 2/2005 |
| WO | WO 2005/080986 | 9/2005 |
| WO | 2005120166 A2 | 12/2005 |
| WO | WO 2007/068105 | 6/2007 |
| WO | WO 2008/150949 | 12/2008 |
| WO | 2010/115843 A2 | 10/2010 |
| WO | WO 2010/144711 | 12/2010 |
| WO | 2011013034 A1 | 2/2011 |
| WO | 2011026031 A1 | 3/2011 |
| WO | 2011056300 A1 | 5/2011 |
| WO | 2012045882 A2 | 4/2012 |
| WO | 2012049570 A1 | 4/2012 |
| WO | 2012054008 A2 | 4/2012 |
| WO | WO 2012/045882 * | 4/2012 |
| WO | 2012106363 A2 | 8/2012 |
| WO | WO 2012/126013 | 9/2012 |
| WO | 2013007839 A1 | 1/2013 |
| WO | WO 2013/004717 | 1/2013 |
| WO | 2013041962 A1 | 3/2013 |
| WO | 2013044147 A1 | 3/2013 |
| WO | 2013050567 A1 | 4/2013 |
| WO | 2013063086 A1 | 5/2013 |
| WO | 2013096380 A2 | 6/2013 |
| WO | 2013151762 A1 | 10/2013 |
| WO | 2014008404 A1 | 1/2014 |
| WO | 2014028777 A2 | 2/2014 |
| WO | 2014031694 A2 | 2/2014 |
| WO | 2014200921 A1 | 12/2014 |
| WO | 2015081085 A2 | 6/2015 |
| WO | 2015/122922 A1 | 8/2015 |

OTHER PUBLICATIONS

Min, Sang-Won et al., "Acetylation of Tau Inhibits Its Degradation and Contributes to Tauopathy," Neuron., vol. 67(6):953-966 (2010).

Odetti, P. et al., "Lipoperoxidation is selectively involved in progressive supranuclear palsy," Journal of Neuropathology and Experimental Neurology, 59(5): 393-397 (2000).

Plouffe, Vanessa et al., "Hyperphosphorylation and Cleavage of D421 Enhance Tau Secretion," PLoS One, vol. 7(5):e36873, doi: 1031371/journal.pone.0036873, 13 pages (2012).

Rafii, Michael S. et al., "Recent developments in Alzheimer's disease therapeutics," BMC Medicine, vol. 7(7), doi: 103.1186/1741-7015-7-7, 4 pages (2009).

Saman, Sudad et al., "Exosome-associated Tau Is Secreted in Tauopathy Models and Is Selectively Phosphorylated in Cerebrospinal Fluid in Early Alzheimer Disease," The Journal of Biological Chemistry, vol. 287(6):3842-3849 (2012).

Second Written Opinion for Application No. PCT/US2013/055203, 8 pages, dated Jul. 28, 2014.

Sigurdsson, E. "Tau-Focused Immunotherapy for Alzheimer's Disease and Related Tauopathies," Curr Alzheimer Res., vol. 6(5): 446-450 (2009).

Sigurdsson, Einar M., "Immunotherapy Targeting Pathological Tau Protein in Alzheimer's Disease and Related Tauopathies," J. Alzheimer's Dis., vol. 15(2):157-168 (2008).

Terwel, Dick et al., "Changed Conformation of Mutant Tau-P301L Underlies the Moribund Tauopathy, Absent in Progressive, Nonlethal Axonopathy of Tau-4R/2N Transgenic Mice," The Journal of Biological Chemistry, vol. 280(5):3963-3973 (2005).

Troquier, Laetitia et al., "Targeting Phospho-Ser422 by Active Tau Immunotherapy in the THY-Tau22 Mouse Model: A Suitable Therapeutic Approach," Current Alzheimer Research, vol. 9:397-405 (2012).

(56) References Cited

OTHER PUBLICATIONS

Vigo-Pelfrey, C. et al., "Elevation of microtubule-associated protein tau in the cerebrospinal fluid of patients with Alzheimer's disease," Neurology, vol. 45:788-793 (1995).
Ward, Sarah M. et al., "Tau oligomers and tau toxicity in neurodegenerative disease," Biochem. Soc. Trans, vol. 40:667-671 (2012).
Waxman, Elisa A. et al., "Induction of intracellular tau aggregation is promoted by a-synuclein seeds, and provides novel insights into the hyperphosphorylation of tau," J. Neurosci., vol. 31(21):7604-7618 (2011).
Whiteman, Ineka T. et al., "Rapid Changes in Phosph-MAP/Tau Epitopes during Neuronal Stress: Cofilin-Actin Rods Primarily Recruit Microtubule Binding Domain Epitopes," PLoS One, vol. 6(6):e20878, doi: 1031371/journal.pone.0020878, 12 pages (2011).
Williams, D.R. "Tauopathies: classification and clinical update on neurodegenerative diseases associated with microtubule-associated protein tau," Internal Medicine Journal, vol. 36 (10):652-660 (2006).
Yamamori, Hidenaga et al., "Tau in cerebrospinal fluid: a sensitive sandwich enzyme-linked immunosorbent assay using tyramide signal amplification," Neurosci. Lett., vol. 418(2):186-189 (2007).
Yanamandra K. et al., "Anti-Tau Antibodies that Block Tau Aggregate Seeding in Vitro Markedly Decrease Pathology and Improve Cognition in Vivo," Neuron, vol. 80(2): 402-414 (2013).
Yanamandra K. et al., "Supplementary Information Anti-tau antibodies that block tau aggregate seeding in vitro markedly decrease pathology and improve cognition in vivo", (2013) Retrieved from the Internet: URL:http://www.ncbi.nlm.nih.gov/pmc/articles/PMC3924573/bin/NIHMS548975-supplement-Supplementary data.docx, 32 pages.
Yoshiyama, Yasumasa et al., "Therapeutic strategies for tau mediated neurodegeneration," J. Neurol. Neurosurg. Psychiatry, vol. 84:784-795 (2013).
Arnesen, T., "Towards a Functional Understanding of Protein N-Terminal Acetylation," PLoS Biology, vol. 9(5): e1001074, doi: 10.1371/journal.pbio.1001074, 5 pages (2011).
Asuni, Ayodeji A. et al., "Immunotherapy Targeting Pathological Tau Conformers in a Tangle Mouse Model Reduces Brain Pathology with Associated Functional Improvements," The Journal of Neuroscience, vol. 27(34):9115-9129 (2007).
Bartos, Ales et al., "Patients with Alzheimer disease have elevated intrathecal synthesis of antibodies against tau protein and heavy neurofilament," Journal of Neuroimmunology, vol. 252:100-105 (2012).
Bi, Mian et al., "Tau-Targeted Immunization Impedes Progression of Neurofibrillary Histopathology in Aged P301L Tau Transgenic Mice," PLoS One, vol. 6(12):e26860, doi: 10.1371/journal.pone.0026860, 7 pages (2011).
Binder, Lester I. et al., "Tau, tangles, and Alzheimer's disease," Biochimica et Biophysica Acta, vol. 1739:216-223 (2005).
Borroni, B. et al., "Pattern of Tau forms in CSF is altered in progressive supranuclear palsy," Neurobiology of Aging, vol. 30:34-40 (2009).
Boutajangout, Allal et al., "Passive immunization targeting pathological phospho-tau protein in a mouse model reduces functional decline and clears tau aggregates from the brain," Journal of Neurochemistry, vol. 118:658-667 (2011).
Braak, Heiko et al., "Staging of Alzheimer's Disease-Related Neurofibrillary Changes," Neurobiology of Aging, vol. 16(3)271-284 (1995).
Bright, J. et al., "Human secreted tau increases amyloid-beta production," Neurobiology of Aging, vol. 36: 693-709 (2015).
Brunden, Kurt R. et al., "Advances in Tau-focused drug discovery for Alzheimer's disease and related tauopathies," Nat. Rev. Drug Discov., vol. 8(10):783-793 (2009).
Carmel, Gilles et al., The Structural Basis of Monoclonal Antibody Alz50's Selectivity for Alzheimer's Disease Pathology, vol. 271(51):32789-32795 (1996).
Castillo-Carranza, D. et al., "Tau aggregates as immunotherapeutic targets," Frontiers in Bioscience, vol. 5:426-438. (2013).

Chai, X. et al., "Passive Immunization with Anti-Tau Antibodies in Two Transgenic Models: Reduction of Tau Pathology and Delay of Disease Progression," J. Biol. Chem., vol. 286(39): 34457-34467 (2011).
Chow, K. Martin et al., "Aminopeptidases do not directly degrade tau protein," Molecular Neurodegeneration, vol. 5:48, doi: 10.1186/1750-1326-5-48, 10 pages (2010).
De Meyer, Geert et al., "Diagnosis-Independent Alzheimer Disease Biomarker Signature in Cognitively Normal Elderly People," Arch. Neurol., vol. 67(8):949-956 (2010).
De Strooper, Bart, "Proteases and Proteolysis in Alzheimer Disease: A Multifactorial View on the Disease Process," Physiol. Rev., vol. 90:465-494 (2010).
Demeule, Michel et al., "Identification and Design of Peptides as a New Drug Delivery System for the Brain," The Journal of Pharmacology and Experimental Therapeutics, vol. 324(3):1064-1072 (2008).
European Search Report, EP Application No. 13830020.7, dated May 9, 2016, 9 pages.
Fagan, Anne M. et al., "Cerebrospinal Fluid biomarkers of Alzheimer's disease," Biomark. Med., vol. 4(1):51-63 (2010).
Garcia-Sierra, Francisco et al., "Conformational changes and truncation of tau protein during tangle evolution in Alzheimer's disease," Journal of Alzheimer's Disease, vol. 5:65-77 (2003).
GenBank Accession No. CAI54295, "kappa light chain variable region, partial [Mus musculus]," 3 pages Apr. 15, 2005.
GenBank Accession No. NP_058525, "microtubule-associated protein tau isoform 4 [*Homo sapiens*]," 32 pages, Jan. 5, 2014.
Ghoshal, N. "Tau Conformational Changes Correspond to Impairments of Episodic Memory in Mild Cognitive Impairment and Alzheimer's Disease," Experimental Neurology, vol. 177( 2):475-493 (2002).
Ghoshal, Nupur et al., "Tau-66: evidence for a novel tau conformation in Alzheimer's disease," Journal of Neurochemistry, vol. 77:1372-1385 (2001).
Gomez-Ramos, A. et al., "Extracellular tau is toxic to neuronal cells," FEBS Letters vol. 580, pp. 4842-4850 (2006).
Griswold-Prenner, I. et al., "Effects of a Tau therapeutic antibody of the ISF/CSF levels of secreted Tau in the P301L mouse model," Neuroscience, Nanosymposium, Poster No. 598.07, 2 pages (2013).
Gu, J. et al., "Two Novel Tau Antibodies Targeting the 396/404 Region Are Primarily Taken Up by Neurons and Reduce Tau Protein Pathology," The Journal of Biological Chemistry, vol. 288(46):33081-33095 (2013).
Guillozet-Bongaarts, Angela L. et al., "Tau truncation during neurofibrillary tangle evolution in Alzheimer's disease," Neurobiology of Aging, vol. 26:1015-1022 (2005).
Higuciii, Makoto et al., "Tau Protein and Tauopathy," Neuropsychopharmacology—5th Generation of Progress, Williams, & Wilkins, Philadelphia, Chapter 94, pp. 1339-1354 (2002).
Horowitz, Peleg M. et al., "Early N-Terminal Changes and Caspase-6 Cleavage of Tau in Alzheimer's Disease," The Journal of Neuroscience, vol. 24(36):7895-7902 (2004).
Hu, William T. et al., "Biomarker Discovery for Alzheimer's Disease, Frontotemporal Lobar Degeneration, and Parkinson's Disease," Acta Neuropathol., vol. 120(3):385-399 (2010).
International Preliminary Report on Patentability for Application No. PCT/US2013/55203, 34 pages, dated Sep. 19, 2014
International Preliminary Report on Patentability, PCT/US2014/041553, dated Dec. 15, 2015, 7 pages.
International Preliminary Report on Patentability, PCT/US2014/067360, dated Feb. 4, 2016, 29 pages.
International Preliminary Report on Patentability, PCTUS2014/016597, dated Aug. 16, 2016, 9 pages.
International Search Report and Written Opinion for Application No. PCT/US2014/041553, 14 pages, dated Sep. 2, 2014.
International Search Report and Written Opinion, PCT/US2014/067360, dated Jun. 17, 2015, 22 pages.
International Search Report and Written Opinion, PCT/US2014/016597, dated Jul. 24, 2014, 14 pages.
Ishiguro, Koichi et al., "Phosphorylated tau in human cerebrospinal fluid is a diagnostic marker for Alzheimer's disease," Neuroscience Letters, vol. 270:91-94 (1999).

(56) References Cited

OTHER PUBLICATIONS

Israel, Mason A. et al., "Probing sporadic and familial Alzheimer's disease using induced pluripotent stem cells," Nature, vol. 482(7384):216-220 (2012).
Jicha, Gregory A. et al., "Sequence Requirements for Formation of Conformational Variants of Tau Similar to Those Found in Alzheimer's Disease," Journal of Neuroscience Research, vol. 56:713-723 (1999).
Johnson, Gail V.W. et al., "The tau Protein in Human Cerebrospinal Fluid in Alzheimer's Disease Consists of Proteolytically Derived Fragments," Journal of Neurochemistry, vol. 68:430-433 (1997).
Kanaan, Nicholas M. et al., "Pathogenic Forms of Tau Inhibit Kinesin-Dependent Axonal Transport through a Mechanism Involving Activation of Axonal Phosphotransferases," The Journal of Neuroscience, vol. 31(27):9858-9868 (2011).
Kanaan, Nicholas M. et al., "Phosphorylation in the amino terminus of tau prevents inhibition of anterograde axonal transport," Neurobiol. Aging, vol. 33(4):826.e15-826.e30 (2012).
Kfoury, N. et al."Trans-cellular Propagation of Tau Aggregation by Fibrillar Species," J. Biol. Chem., vol. 287(23):19440-19451. (2012).
Kim, Won Hee et al., "Secretion of human tau fragments resembling CFF-tau Alzheimer's disease is modulated by the presence of the exon 2 insert," FEBS Letters, vol. 584:3085-3088 (2010).
Ksiezak-Reding, H. et al., "Mapping of the Alz 50 Epitope in Microtubule-Associated Proteins Tau," Journal of Neuroscience Research, vol. 25:412-419 (1990).
Kuo, M. et al., "N-terminal polyubiquitination and degradation of the Art tumor Suppressor," Genes Dev., vol. 18(15):1862-1874 (2004).
Lewis, Jada et al., "Neurofibrillary tangles, amyotrophy and progressive motor disturbance in mice expressing mutant (P301L) tau protein," Nature Genetics, vol. 25:402-405 (2000).
International Preliminary Report on Patentability for Application No. PCT/US2014/041553, dated Dec. 15, 2015, 7 pages.
International Search Report and Written Opinion, PCT/US2013/055203, 18 pages, dated Mar. 18, 2014.
Supplementary European Search Report in European Application No. 14882522.7, dated Aug. 16, 2017, 10 pages.
Angal et al., "A single amino acid substitution abolishes the heterogeneity of chimeric mouse/human (IgG4) antibody," Mol Immunol. 30(1):105-8 (Jan. 1993) Abstract, 1 page.
Nance et al., "A Dense Poly(Ethylene Glycol) Coating Improves Penetration of Large Polymeric Nanoparticles Within Brain Tissue," Science Translational Medicine, Aug. 2012, 4(149): 149ra119-149ra119.

"[No Author Listed],""iPierian to Present Data on Tau Antibody Preclinical Efficacy Study for Alzheimer's Program at Society for Neuroscience Annual Meeting, FirstWord Pharma, Nov. 1, 2013, [retrieved on Jun. 29, 2018], retrieved from the internet: <URL: https://www.firstwordpharma.com/node/1151454?tsid=17>, 2 pages".
[No Author Listed], "Treating tau: Finally, Clinical Candidates Are Stepping Into the Ring," Alzforum, Apr. 27, 2017, [retrieved on Feb. 6, 2018], retrieved from: URL <http://www.alzforum.org/news/conference-coverage/treating-tau-finally-clinical-candidates-are-stepping-ring>, 8 pages.
Biogen, "Biogen Licenses Phase 2 Anti-Tau Antibody from Bristol-Myers Squibb," Biogen Media, Apr. 13, 2017, [retrieved on Feb. 6, 2018], retrieved from: URL<http://media.biogen.com/printpdf/5118>, 2 pages.
Braak et al., "Alzheimer's pathogenesis: is there neuron-to-neuron propagation?," Acta Neuropathol, (2011), 121:589-595.
D'Abramo et al., "Tau Passive Immunotherapy in Mutant P301L Mice: Antibody Affinity versus Specificity," PLOS One, 8(4):e62402, pp. 1-10 (Apr. 2013).
De Calignon et al., "Propagation of tau pathology in a model of early Alzheimer's disease," Neuron, (2012), 73:685-697.
Eschlböck S et al., "Interventional trials in atypical parkinsonism," Parkinsonism and Related Disorders, vol. 22:590. doi: 10.1016/j.parkreldis.2015.09.038 (2016).
Fiore, "Anti-Tau Drugs for PSP Move into Phase II," Medpage Today, Jun. 8, 2017, [retrieved on Feb. 6, 2018], retrieved from: URL:<https://www.medpagetoday.com/meetingcoverage/mds/65883>, 3 pages.
Frost et al., "Propagation of tau misfolding from the outside to the inside of a cell," The Journal of Biological Chemistry, (2009), 284(19):12845-12852.
Guo et al., "Seeding of normal Tau by pathological Tau conformers drives pathogenesis of Alzheimer-like tangles," The Journal of Biological Chemistry, (2011), 286(17):15317-15331.
International Search Report and Written Opinion, PCT/US2017/037991, dated Apr. 18, 2018, 21 pages.
Kunze et al., "Co-pathological connected primary neurons in a microfluidic device for Alzheimer studies," Biotechnology and Bioengineering, (2011), 108(9):2241-2245.
Kunzmann, "Monoclonal Antibody Effective Against Progressive Supranuclear Palsy," MD Magazine, Feb. 6, 2018, [retrieved on Feb. 6, 2018], retrieved from: URL<http://www.mdmag.com/print.php?url=/conference-coverage/mds-2017/monoclonal-anitbody-effective-against-progressive-supranuclear-palsy>, 2 pages.
Santa-Maria et al., "Paired helical filaments from Alzheimer disease brain induce intracellular accumulation of Tau protein in aggresomes," Journal of Biological Chemistry, (2012), 287(24):20522-20533.

* cited by examiner

```
                 10         20         30         40         50         60
fetal      MAEPRQEFEVMEDHAGTYGLGDRKDQGGYTMHQDQEGDTDAGLKAEEAGIGDTPSLEDEA
#2            AEPRQEFEVMEDHAGTYGLGDRKDQGGYTMHQDQEGDTDAGLKAEEAGIGDTPSLEDEA
#3            AEPRQEFEVMEDHAGTYGLGDRKDQGGYTMHQDQEGDTDAGLKAEEAGIGDTPSLEDEA
#4            AEPRQEFEVMEDHAGTYGLGDRKDQGGYTMHQDQEGDTDAGLKAEEAGIGDTPSLEDEA
eTau 2-172    AEPRQEFEVMEDHAGTYGLGDRKDQGGYTMHQDQEGDTDAGLKAEEAGIGDTPSLEDEA
eTau 2-176    AEPRQEFEVMEDHAGTYGLGDRKDQGGYTMHQDQEGDTDAGLKAEEAGIGDTPSLEDEA
eTau 2-166    AEPRQEFEVMEDHAGTYGLGDRKDQGGYTMHQDQEGDTDAGLKAEEAGIGDTPSLEDEA 70         80         90        100        110        120
fetal      AGHVTQARMVSKSKDGTGSDDKKAKGADGKTKIATPRGAAPPGQKGQANATRIPAKTPPA
#2         AGHVTQARMVSKSKDGTGSDDKKAKGADGKTKIATPRGAAPPGQKGQANATRIPAKTPPA
#3         AGHVTQARMVSKSKDGTGSDDKKAKGADGKTKIATPRGAAPPGQKGQANATRIPAKTPPA
#4         AGHVTQAR (68) (SEQ ID NO:6)
eTau 2-172 AGHVTQARMVSKSKDGTGSDDKKAKGADGKTKIATPRGAAPPGQKGQANATRIPAKTPPA
eTau 2-176 AGHVTQARMVSKSKDGTGSDDKKAKGADGKTKIATPRGAAPPGQKGQANATRIPAKTPPA
eTau 2-166 AGHVTQARMVSKSKDGTGSDDKKAKGADGKTKIATPRGAAPPGQKGQANATRIPAKTPPA 130        140        150        160        170        180
fetal      PKTPPSSGEPPKSGDRSGYSSPGSPGTPGSRSRTPSLPTPPTREPKKVAVVRTPPKSPSS
#2         PKTPPSSGEPPKSGDRSGYSSPGSPGTPGSR (151) (SEQ ID NO:4)
#3         PK (122) (SEQ ID NO:5)
eTau 2-172 PKTPPSSGEPPKSGDRSGYSSPGSPGTPGSRSRTPSLPTPPTREPKKVAVVR (SEQ ID NO:2)
eTau 2-176 PKTPPSSGEPPKSGDRSGYSSPGSPGTPGSRSRTPSLPTPPTREPKKVAVVRTPPK (SEQ ID NO:1)
eTau 2-166 PKTPPSSGEPPKSGDRSGYSSPGSPGTPGSRSRTPSLPTPPTREPK (SEQ ID NO:3)
```

FIG. 1A fetal   AKSRLQTAPVPMPDLKNVKSKIGSTENLKHQPGGGKVQIVYKPVDLSKVTSKCGSLGNIH
fetal   HKPGGGQVEVKSEKLDFKDRVQSKIGSLDNITHVPGGGNKKIETHKLTFRENAKAKTDHG
fetal   AEIVYKSPVVSGDTSPRHLSNVSSTGSIDMVDSPQLATLADEVSASLAKQGL (SEQ ID NO:7)

FIG. 1B

Tau383 (0N4R)

MAEPRQEFEV MEDHAGTYGL GDRKDQGGYT MHQDQEGDTD AGLKAEEAGI GDTPSLEDEA
AGHVTQARMV SKSKDGTGSD DKKAKGADGK TKIATPRGAA PPGQKGQANA TRIPAKTPPA
PKTPPSSGEP PKSGDRSGYS SPGSPGTPGS RSRTPSLPTP PTREPKKVAV VRTPPKSPSS
AKSRLQTAPV PMPDLKNVKS KIGSTENLKH QPGGGKVQII NKKLDLSNVQ SKCGSKDNIK
HVPGGGSVQI VYKPVDLSKV TSKCGSLGNI HHKPGGGQVE VKSEKLDFKD RVQSKIGSLD
NITHVPGGGN KKIETHKLTF RENAKAKTDH GAEIVYKSPV VSGDTSPRHL SNVSSTGSID
MVDSPQLATL ADEVSASLAK QGL (SEQ ID NO:8)

FIG. 2

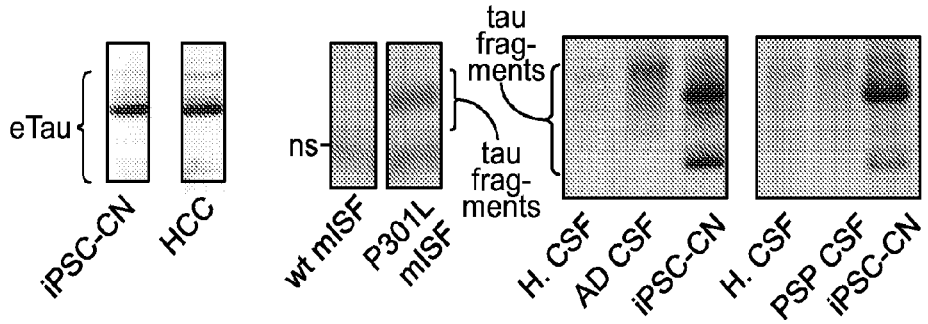
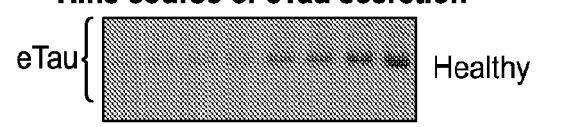
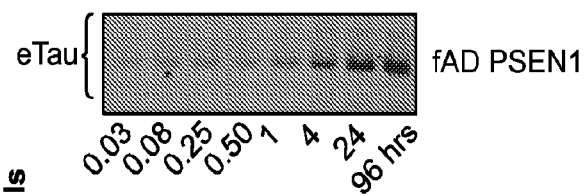
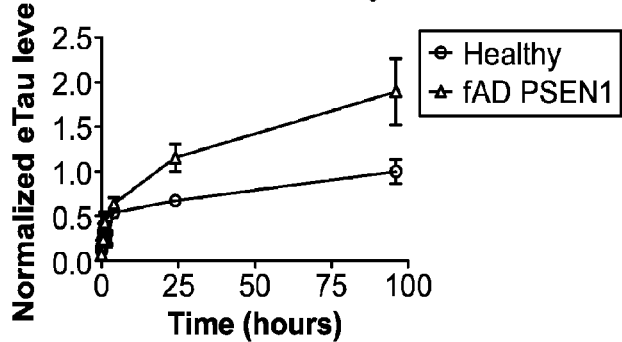
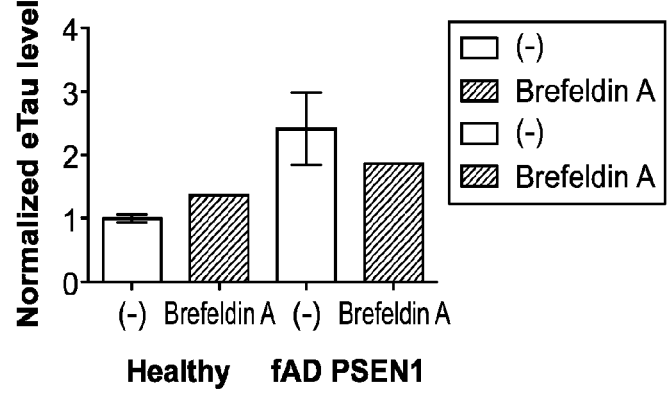
FIG. 5

A
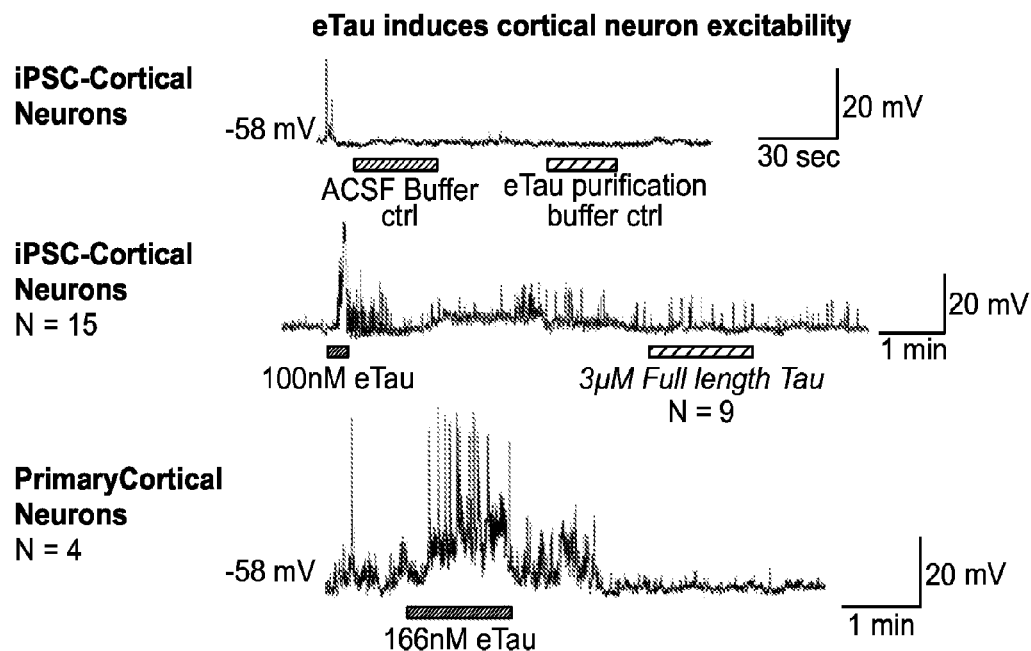
B
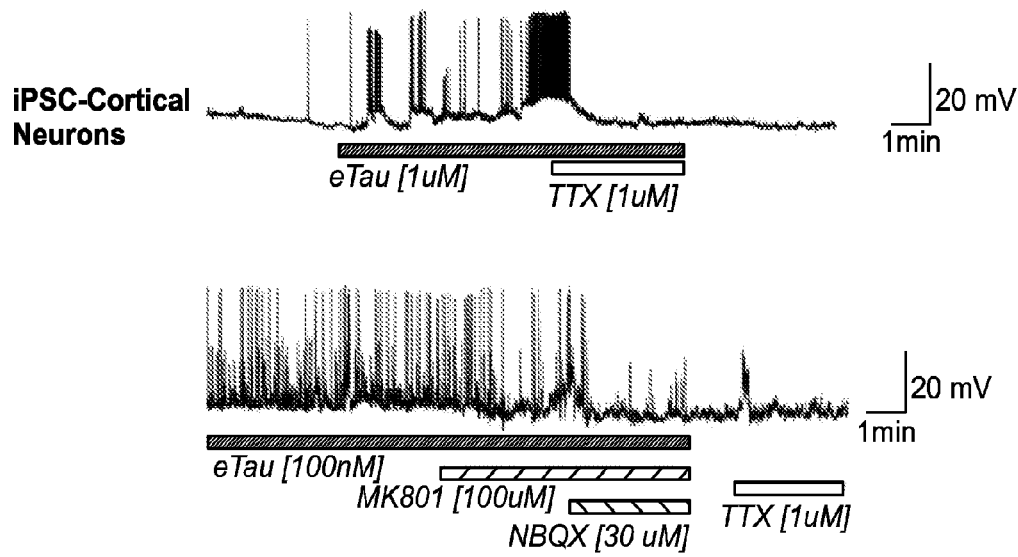
FIG. 8

C
eTau increases calcium mobilization
iPSC-Cortical Neurons
iPSC-Cortical Neurons
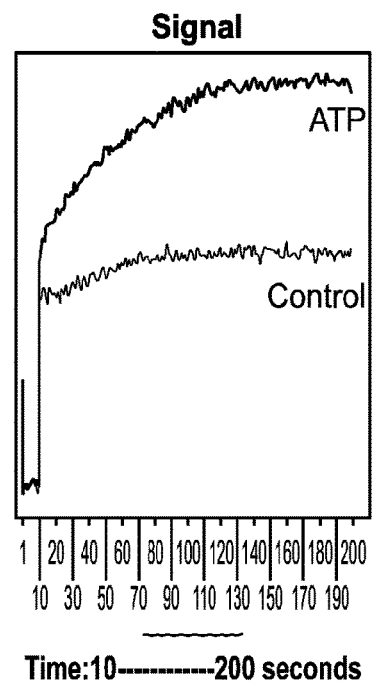
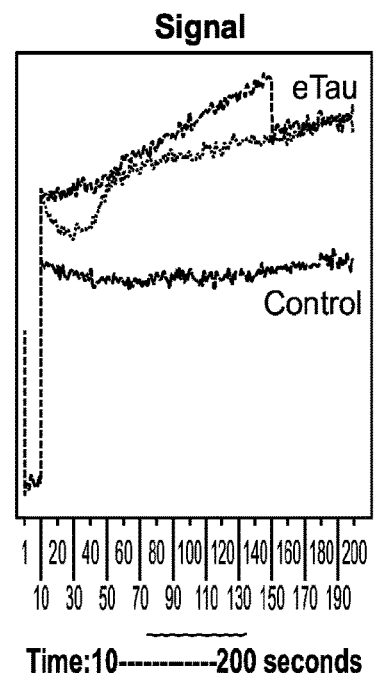
FIG. 8 (Cont.)

A
Western blots of eTau treated MCC
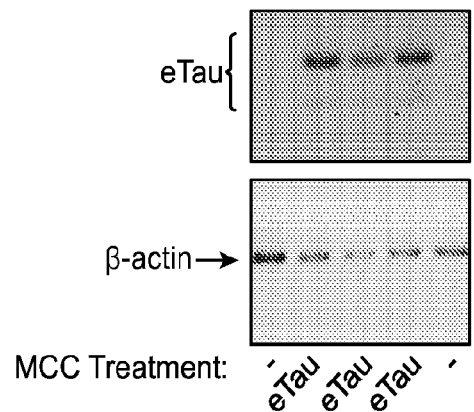
B
Human tau staining in eTau treated MCC
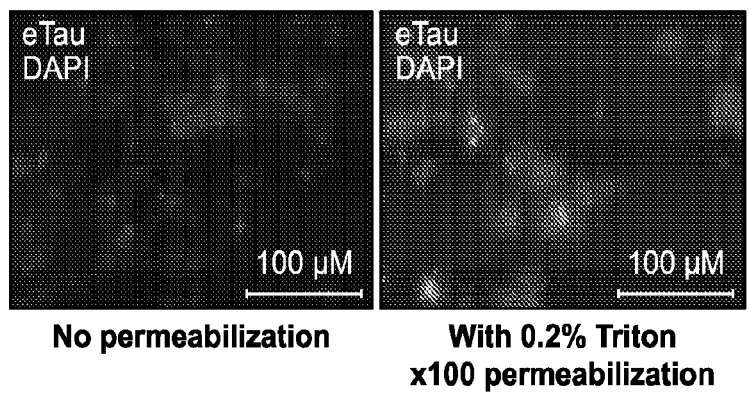
C
Confocal imaging of eTau treated MCC
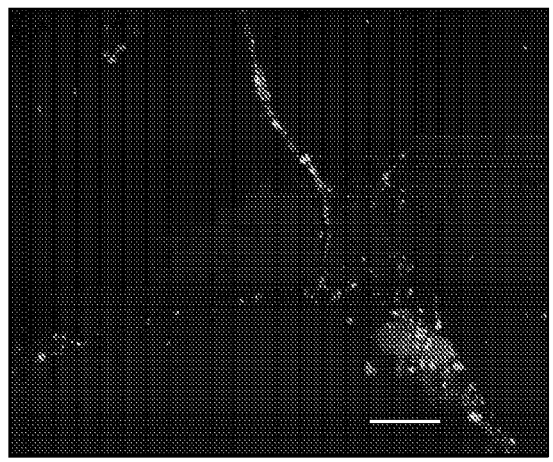
FIG. 9

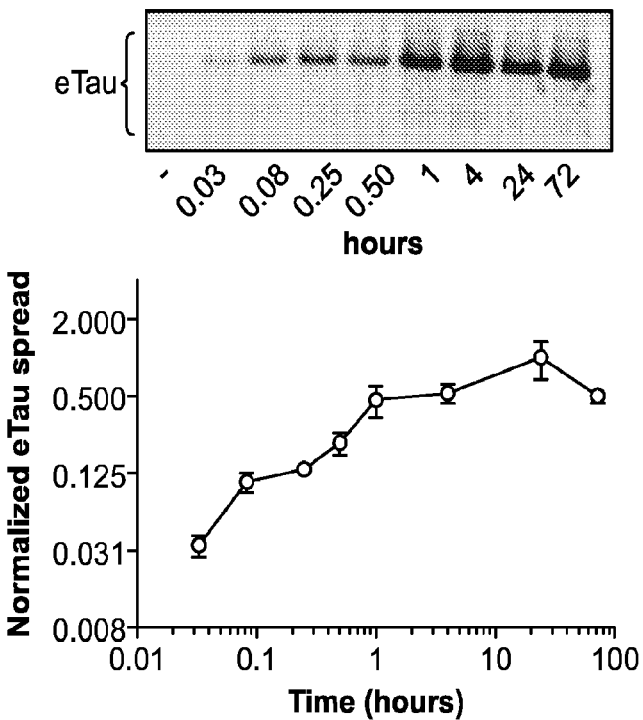
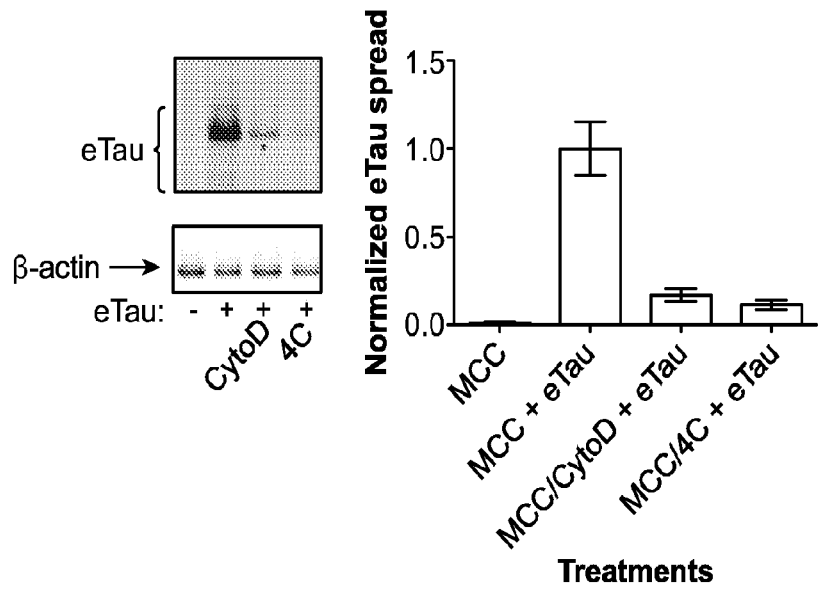
FIG. 9 (Cont.)

Recombinant eTau fragments uptake by MCC

1= 0.1x media reTau 1a
2= 0.1x media reTau 2
3= 0.1x media reTau 3
4= MW ladder
5= MCC
6= MCC + reTau 1a (50nM)
7= MCC + reTau 2 (50nM)
8= MCC + reTau 3 (50nM)

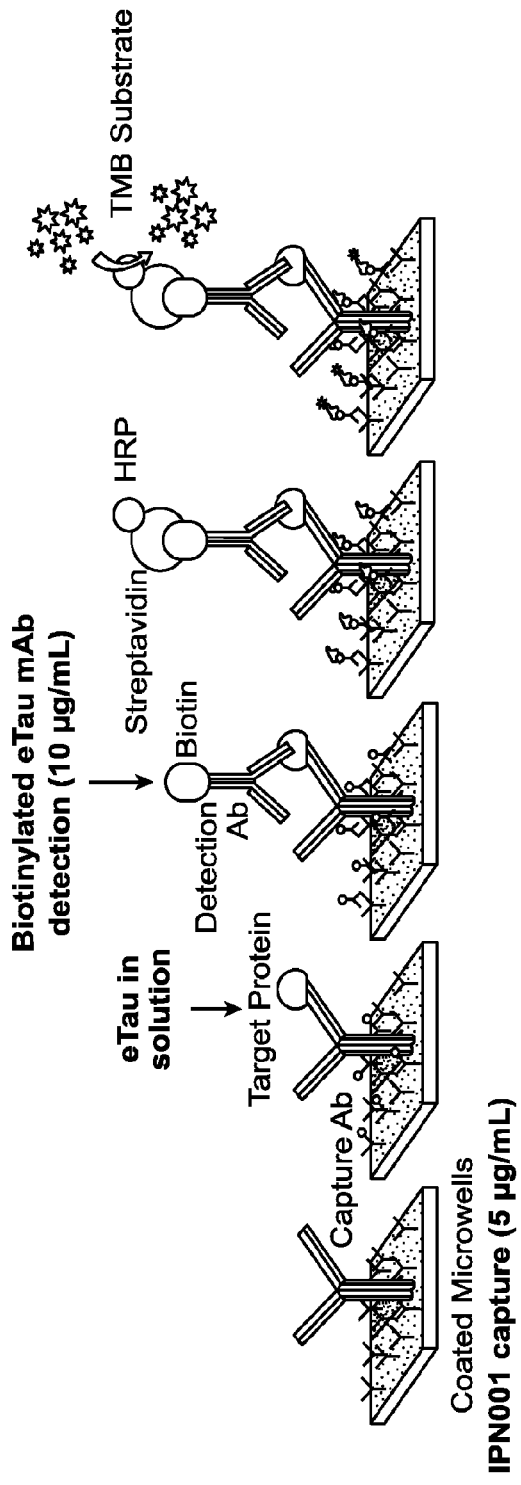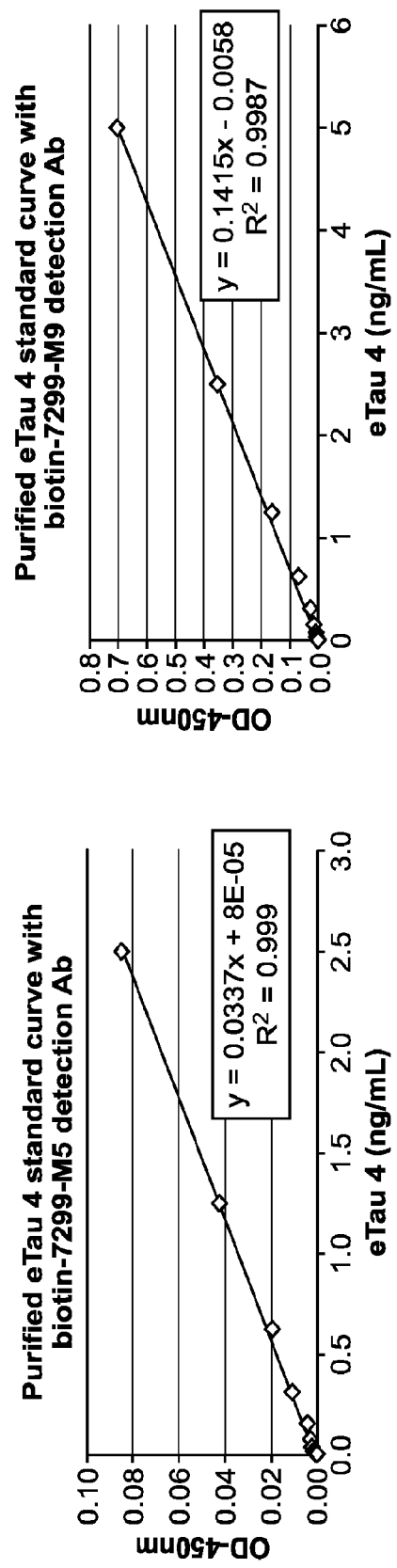
FIG. 16

Table 6

| | CDR1 | CDR2 | CDR3 | VARIABLE REGION |
|---|---|---|---|---|
| 7295-M6 VL | SEQ ID NO:9<br>RSSQTIVHSNGNTYLE | SEQ ID NO:10<br>KVSNRFS | SEQ ID NO:11<br>FQGSHVPFT | SEQ ID NO:15<br>DIVLTQTPLSLPVSLGDPASISCRSSQTIVHSNGN<br>TYLEWYLQKPGQSPKLLIYKVSNRFSGVPDRFS<br>GSGSGTDFTLKISRVEAEDLGVYYCFQGSHVPF<br>TFGSGTKLEIKRADAAPTVST |
| 7295-M6 VH | SEQ ID NO:12<br>GFNIKDYYIH | SEQ ID NO:13<br>WIDPENGDTEYAPKFQG | SEQ ID NO:14<br>APGY | SEQ ID NO:16<br>LPEVQLEESGAELVRSGASVTLSCTASGFNIKD<br>YYIHWVKQRPEQGLEWIGWIDPENGDTEYAPK<br>FQGKATMTADTSSNTAYLQLSSLTSEDTAVYY<br>CNGAPGYWGPGTTLTVSSAKTTPPSVYS |
| 7295-M8 VL | SEQ ID NO:17<br>RSSQTIVHSNGNTYLE | SEQ ID NO:18<br>KVSNRFS | SEQ ID NO:19<br>FQGSHVPFT | SEQ ID NO:23<br>DIVLTQTPLSLPVSLGDPASISCRSSQTIVHSNGN<br>TYLEWYLQKPGQSPKLLIYKVSNRFSGVPDRFS<br>GSGSGTDFTLKISRVEAEDLGVYYCFQGSHVPF<br>TFGSGTKLEIKRADAAPTVST |
| 7295-M8 VH | SEQ ID NO:20<br>GFNIKDYYIH | SEQ ID NO:21<br>WIDPENGDTEYAPKFQG | SEQ ID NO:22<br>APGY | SEQ ID NO:24<br>LPEVQLEESGAELVRSGASVTLSCTASGFNIKD<br>YYIHWVKQRPEQGLEWIGWIDPENGDTEYAPK<br>FQGKATMTADTSSNTAYLQLSSLTSEDTAVYY<br>CNGAPGYWGPGTTLTVSSAKTTPPSVYS |

FIG. 17

Table 7

| | CDR1 | CDR2 | CDR3 | VARIABLE REGION |
|---|---|---|---|---|
| 7298-M1 VL | SEQ ID NO:25 RASKSVSTSDYSYMH | SEQ ID NO:26 LASNLES | SEQ ID NO:27 QHSRELPFT | SEQ ID NO:31 DIVLTQSPTSLAVSLGQRATISCRASKSVSTSDYS YMHWYQQKPGQPPKLLIYLASNLESGVPARFSGS GSGTDFTLNIHPVEEEDAATYYCQHSRELPFTFGG GTKLEIKRADAAPTVST |
| 7298-M1 VH | SEQ ID NO:28 SGFTFTDYYMS | SEQ ID NO:29 NRNKTKGYTTEYSASVK | SEQ ID NO:30 GMDY | SEQ ID NO:32 LPEVQLEESGGGLVQPGGSLSLSCAASGFTFTDY YMSWVRQPPGKALEWVALNRNKTKGYTTEYSA SVKGRFTISRDNSQSILYLQMNALRAEDSATYYC ARGMDYWGQGTSVTVSSAKTTPPSVYS |
| 7298-M2 VL | SEQ ID NO:33 RASKSVSTSDYSYMH | SEQ ID NO:34 LASNLES | SEQ ID NO:35 QHSRELPFT | SEQ ID NO:39 DIVLTQSPTSLAVSLGQRATISCRASKSVSTSDYS YMHWYQQKPGQPPKLLIYLASNLESGVPARFSGS GSGTDFTLNIHPVEEEDAATYYCQHSRELPFTFGG GTKLEIKRADAAPTVST |
| 7298-M2 VH | SEQ ID NO:36 GFTFSTYPMS | SEQ ID NO:37 SISNGGSTYYPDTV | SEQ ID NO:38 GRDYHFDF | SEQ ID NO:40 LPEVQLEESGGGLVKPGGSLKLSCAASGFTFSTYP MSWVRQTPEKRLEWVASISNGGSTYYPDTVKGR FTISRDNARNILQMSSLRSEDTAMYYCARGRD YHFDFWGQGTTLTVSSAKTTPPSVYS |

FIG. 18

Table 8

| | CDR1 | CDR2 | CDR3 | VARIABLE REGION |
|---|---|---|---|---|
| 7299-M2 VL | SEQ ID NO:41<br>KSSQSLLYSDGKTFLN | SEQ ID NO:42<br>LVSKLQS | SEQ ID NO:43<br>VQGTHFPYT | SEQ ID NO:47<br>DIVLTQTPLTLSVTIGQPASISCKSSQSLLYSDG<br>KTFLNWLLQSPGQSPRLLIYLVSKLQSGVPDRF<br>SGSGSGTDFTLKISRVEAEDLGVYCVQGTHFP<br>YTFGGGTKLEIKRADAAPTVST |
| 7299-M2 VH | SEQ ID NO:44<br>GYTFTNYWIN | SEQ ID NO:45<br>IYPGSTRANYNEKFKS | SEQ ID NO:46<br>THSI | SEQ ID NO:48<br>LPQVQLEESGAELVKPGASVKLSCKASGYTFT<br>NYWINWVKQRPGQGLEWIGNIYPGSTRANYN<br>EKFKSKATLTVDTSSSTAYMQVSSLTSDDSAV<br>YYCTRTHSIWGQGTQVTVSAAKTTPPSVYS |
| 7299-M5 VL | SEQ ID NO:49<br>KSSQSLLYSDGKTYLN | SEQ ID NO:50<br>QVSKLDP | SEQ ID NO:51<br>LQGTYYPHT | SEQ ID NO:55<br>DIVMTQSPLSLSVTIGQPASISCKSSQSLLYSDG<br>KTYLNWLQQRPGQSPKRLVYQVSKLDPGIPDR<br>FSGSGSETDFTLKLSRVEAEDLGVYYCLQGTY<br>YPHTFGGGTKLEIKRADAAPTVST |
| 7299-M5 VH | SEQ ID NO:52<br>GYTFISNWMH | SEQ ID NO:53<br>IDPSDSETHYNQKFKD | SEQ ID NO:54<br>RDRDGYYFDY | SEQ ID NO:56<br>LPEVKLEESGAELVKPGASVKLSCKASGYTFIS<br>NWMHWVKQRPGQGLEWIGNIDPSDSETHYNQ<br>KFKDKATLTVDKSSSTAYMQLSSLTSEDSAVY<br>YCARRDRDGYYFDYWGQGTILTVSSAKTTPPS<br>VYS |
| 7299-M9 VL | SEQ ID NO:57<br>KSSQSLLYSDGKTYLN | SEQ ID NO:58<br>QVSKLDP | SEQ ID NO:59<br>LQGTYYPH | SEQ ID NO:63<br>DIVITQSPLSLSVTIGQPASISCKSSQSLLYSDGK<br>TYLNWLQQRPGQSPKRLVYQVSKLDPGIPDRF<br>SGSGSETDFTLKLSRVEAEDLGVYYCLQGTYY<br>PHITFGGGTKLEIKRADAAPTVST |
| 7299-M9 VH | SEQ ID NO:60<br>GYTFTNYWIN | SEQ ID NO:61<br>IYPGSTRANYNEKFK | SEQ ID NO:62<br>THSI | SEQ ID NO:64<br>LPEVKLEQSGAELVKPGASVKLSCKASGYTFT<br>NYWINWVKQRPGQGLEWIGNIYPGSTRANYN<br>EKFKSKATLTVDTSSSTAYMQVSSLTSDDSAV<br>YYCTRTHSIWGQGTQVTVSAAKTTPPSVYS |

FIG. 19

Table 9

| | CDR1 | CDR2 | CDR3 | VARIABLE REGION |
|---|---|---|---|---|
| 7297-2M1 VL | SEQ ID NO:65<br>KASQDINKYIA | SEQ ID NO:66<br>YTSTLQS | SEQ ID NO:67<br>LQYDHLLT | SEQ ID NO:71<br>DIVLTQTPSSLSASLGGKVTITCKASQDINKYIA WYQHKPGKGPRLLIHYTSTLQSGIPSRFSGSGS GRDYSFSISNLEPEDIATYYCLQYDHLLTFGAG TKLELKRADAAPTVST |
| 7297-2M1 VH | SEQ ID NO:68<br>GYTFISNWMH | SEQ ID NO:69<br>NIDPSDSETHYNQKFKD | SEQ ID NO:70<br>RDRDGYYFDY | SEQ ID NO:72<br>LPEVQLEQSGAELVKPGASVKLSCKASGYTFIS NWMHWVKQRPGQGLEWIGNIDPSDSETHYNQ KFKDKATLTVDKSSSTAYMQLSSLTSEDSAVY YCARRDRDGYYFDYWGQGTTLTVSSAKTTPPS VYS |

SEQUENCE LISTING

<160> NUMBER OF SEQ ID NOS: 100

<210> SEQ ID NO 1
<211> LENGTH: 175
<212> TYPE: PRT
<213> ORGANISM: Homo sapiens

<400> SEQUENCE: 1

Ala Glu Pro Arg Gln Glu Phe Glu Val Met Glu Asp His Ala Gly Thr
1               5                   10                  15
Tyr Gly Leu Gly Asp Arg Lys Asp Gln Gly Gly Tyr Thr Met His Gln
            20                  25                  30
Asp Gln Glu Gly Asp Thr Asp Ala Gly Leu Lys Ala Glu Glu Ala Gly
        35                  40                  45
Ile Gly Asp Thr Pro Ser Leu Glu Asp Glu Ala Ala Gly His Val Thr
    50                  55                  60
Gln Ala Arg Met Val Ser Lys Ser Lys Asp Gly Thr Gly Ser Asp Asp
65                  70                  75                  80
Lys Lys Ala Lys Gly Ala Asp Gly Lys Thr Lys Ile Ala Thr Pro Arg
                85                  90                  95
Gly Ala Ala Pro Pro Gly Gln Lys Gly Gln Ala Asn Ala Thr Arg Ile
            100                 105                 110
Pro Ala Lys Thr Pro Pro Ala Pro Lys Thr Pro Ser Ser Gly Glu
            115                 120                 125
Pro Pro Lys Ser Gly Asp Arg Ser Gly Tyr Ser Ser Pro Gly Ser Pro
        130                 135                 140
Gly Thr Pro Gly Ser Arg Ser Arg Thr Pro Ser Leu Pro Thr Pro Pro
145                 150                 155                 160
Thr Arg Glu Pro Lys Lys Val Ala Val Val Arg Thr Pro Pro Lys
                165                 170                 175

<210> SEQ ID NO 2
<211> LENGTH: 171
<212> TYPE: PRT
<213> ORGANISM: Homo sapiens

<400> SEQUENCE: 2

Ala Glu Pro Arg Gln Glu Phe Glu Val Met Glu Asp His Ala Gly Thr
1               5                   10                  15
Tyr Gly Leu Gly Asp Arg Lys Asp Gln Gly Gly Tyr Thr Met His Gln
            20                  25                  30
Asp Gln Glu Gly Asp Thr Asp Ala Gly Leu Lys Ala Glu Glu Ala Gly
        35                  40                  45
Ile Gly Asp Thr Pro Ser Leu Glu Asp Glu Ala Ala Gly His Val Thr
    50                  55                  60
Gln Ala Arg Met Val Ser Lys Ser Lys Asp Gly Thr Gly Ser Asp Asp
65                  70                  75                  80
Lys Lys Ala Lys Gly Ala Asp Gly Lys Thr Lys Ile Ala Thr Pro Arg
                85                  90                  95
Gly Ala Ala Pro Pro Gly Gln Lys Gly Gln Ala Asn Ala Thr Arg Ile
            100                 105                 110
Pro Ala Lys Thr Pro Pro Ala Pro Lys Thr Pro Ser Ser Gly Glu
            115                 120                 125
Pro Pro Lys Ser Gly Asp Arg Ser Gly Tyr Ser Ser Pro Gly Ser Pro
        130                 135                 140
Gly Thr Pro Gly Ser Arg Ser Arg Thr Pro Ser Leu Pro Thr Pro Pro
145                 150                 155                 160
Thr Arg Glu Pro Lys Lys Val Ala Val Val Arg
                165                 170

<210> SEQ ID NO 3
<211> LENGTH: 165

```
<212> TYPE: PRT
<213> ORGANISM: Homo sapiens

<400> SEQUENCE: 3

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Pro Ala Pro Lys Thr Pro Pro Ser Ser Gly Glu
        115                 120                 125

Pro Pro Lys Ser Gly Asp Arg Ser Gly Tyr Ser Ser Pro Gly Ser Pro
    130                 135                 140

Gly Thr Pro Gly Ser Arg Ser Arg Thr Pro Ser Leu Pro Thr Pro Pro
145                 150                 155                 160

Thr Arg Glu Pro Lys
                165

<210> SEQ ID NO 4
<211> LENGTH: 150
<212> TYPE: PRT
<213> ORGANISM: Homo sapiens

<400> SEQUENCE: 4

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Pro Ala Pro Lys Thr Pro Pro Ser Ser Gly Glu
        115                 120                 125

Pro Pro Lys Ser Gly Asp Arg Ser Gly Tyr Ser Ser Pro Gly Ser Pro
    130                 135                 140

Gly Thr Pro Gly Ser Arg
145                 150

<210> SEQ ID NO 5
<211> LENGTH: 121
```

```
<212> TYPE: PRT
<213> ORGANISM: Homo sapiens

<400> SEQUENCE: 5

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Pro Ala Pro Lys
        115                 120

<210> SEQ ID NO 6
<211> LENGTH: 67
<212> TYPE: PRT
<213> ORGANISM: Homo sapiens

<400> SEQUENCE: 6

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
50                  55                  60

Gln Ala Arg
65

<210> SEQ ID NO 7
<211> LENGTH: 352
<212> TYPE: PRT
<213> ORGANISM: Homo sapiens

<400> SEQUENCE: 7

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
```

```
            100                 105                 110
Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
                260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 8
<211> LENGTH: 383
<212> TYPE: PRT
<213> ORGANISM: Homo sapiens

<400> SEQUENCE: 8

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
            115                 120                 125
```

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 9
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 9

Arg Ser Ser Gln Thr Ile Val His Ser Asn Gly Asn Thr Tyr Leu Glu
1               5                   10                  15

<210> SEQ ID NO 10
<211> LENGTH: 7
<212> TYPE: PRT
<213> ORGANISM: Artificial sequence
<220> FEATURE:
<223> OTHER INFORMATION: synthetic polypeptide

<400> SEQUENCE: 10

Lys Val Ser Asn Arg Phe Ser
1               5

<210> SEQ ID NO 11
<211> LENGTH: 9
<212> TYPE: PRT
<213> ORGANISM: Artificial sequence

```
<220> FEATURE:
<223> OTHER INFORMATION: synthetic polypeptide

<400> SEQUENCE: 11

Phe Gln Gly Ser His Val Pro Phe Thr
1               5

<210> SEQ ID NO 12
<211> LENGTH: 10
<212> TYPE: PRT
<213> ORGANISM: Artificial sequence
<220> FEATURE:
<223> OTHER INFORMATION: synthetic polypeptide

<400> SEQUENCE: 12

Gly Phe Asn Ile Lys Asp Tyr Tyr Ile His
1               5                   10

<210> SEQ ID NO 13
<211> LENGTH: 17
<212> TYPE: PRT
<213> ORGANISM: Artificial sequence
<220> FEATURE:
<223> OTHER INFORMATION: synthetic polypeptide

<400> SEQUENCE: 13

Trp Ile Asp Pro Glu Asn Gly Asp Thr Glu Tyr Ala Pro Lys Phe Gln
1               5                   10                  15

Gly

<210> SEQ ID NO 14
<211> LENGTH: 4
<212> TYPE: PRT
<213> ORGANISM: Artificial sequence
<220> FEATURE:
<223> OTHER INFORMATION: synthetic polypeptide

<400> SEQUENCE: 14

Ala Pro Gly Tyr
1

<210> SEQ ID NO 15
<211> LENGTH: 122
<212> TYPE: PRT
<213> ORGANISM: Artificial sequence
<220> FEATURE:
<223> OTHER INFORMATION: synthetic polypeptide

<400> SEQUENCE: 15

Asp Ile Val Leu Thr Gln Thr Pro Leu Ser Leu Pro Val Ser Leu Gly
1               5                   10                  15

Asp Pro Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

```
Arg Ala Asp Ala Ala Pro Thr Val Ser Thr
        115                 120

<210> SEQ ID NO 16
<211> LENGTH: 125
<212> TYPE: PRT
<213> ORGANISM: Artificial sequence
<220> FEATURE:
<223> OTHER INFORMATION: synthetic polypeptide

<400> SEQUENCE: 16

Leu Pro Glu Val Gln Leu Glu Glu Ser Gly Ala Glu Leu Val Arg Ser
1               5                   10                  15

Gly Ala Ser Val Thr Leu Ser Cys Thr Ala Ser Gly Phe Asn Ile Lys
            20                  25                  30

Asp Tyr Tyr Ile His Trp Val Lys Gln Arg Pro Glu Gln Gly Leu Glu
        35                  40                  45

Trp Ile Gly Trp Ile Asp Pro Glu Asn Gly Asp Thr Glu Tyr Ala Pro
    50                  55                  60

Lys Phe Gln Gly Lys Ala Thr Met Thr Ala Asp Thr Ser Ser Asn Thr
65                  70                  75                  80

Ala Tyr Leu Gln Leu Ser Ser Leu Thr Ser Glu Asp Thr Ala Val Tyr
                85                  90                  95

Tyr Cys Asn Gly Ala Pro Gly Tyr Trp Gly Pro Gly Thr Thr Leu Thr
            100                 105                 110

Val Ser Ser Ala Lys Thr Thr Pro Pro Ser Val Tyr Ser
        115                 120                 125

<210> SEQ ID NO 17
<211> LENGTH: 16
<212> TYPE: PRT
<213> ORGANISM: Artificial sequence
<220> FEATURE:
<223> OTHER INFORMATION: synthetic polypeptide

<400> SEQUENCE: 17

Arg Ser Ser Gln Thr Ile Val His Ser Asn Gly Asn Thr Tyr Leu Glu
1               5                   10                  15

<210> SEQ ID NO 18
<211> LENGTH: 7
<212> TYPE: PRT
<213> ORGANISM: Artificial sequence
<220> FEATURE:
<223> OTHER INFORMATION: synthetic polypeptide

<400> SEQUENCE: 18

Lys Val Ser Asn Arg Phe Ser
1               5

<210> SEQ ID NO 19
<211> LENGTH: 9
<212> TYPE: PRT
<213> ORGANISM: Artificial sequence
<220> FEATURE:
<223> OTHER INFORMATION: synthetic polypeptide

<400> SEQUENCE: 19

Phe Gln Gly Ser His Val Pro Phe Thr
1               5

<210> SEQ ID NO 20
```

```
<211> LENGTH: 10
<212> TYPE: PRT
<213> ORGANISM: Artificial sequence
<220> FEATURE:
<223> OTHER INFORMATION: synthetic polypeptide

<400> SEQUENCE: 20

Gly Phe Asn Ile Lys Asp Tyr Tyr Ile His
1               5                   10

<210> SEQ ID NO 21
<211> LENGTH: 17
<212> TYPE: PRT
<213> ORGANISM: Artificial sequence
<220> FEATURE:
<223> OTHER INFORMATION: synthetic polypeptide

<400> SEQUENCE: 21

Trp Ile Asp Pro Glu Asn Gly Asp Thr Glu Tyr Ala Pro Lys Phe Gln
1               5                   10                  15

Gly

<210> SEQ ID NO 22
<211> LENGTH: 4
<212> TYPE: PRT
<213> ORGANISM: Artificial sequence
<220> FEATURE:
<223> OTHER INFORMATION: synthetic polypeptide

<400> SEQUENCE: 22

Ala Pro Gly Tyr
1

<210> SEQ ID NO 23
<211> LENGTH: 122
<212> TYPE: PRT
<213> ORGANISM: Artificial sequence
<220> FEATURE:
<223> OTHER INFORMATION: synthetic polypeptide

<400> SEQUENCE: 23

Asp Ile Val Leu Thr Gln Thr Pro Leu Ser Leu Pro Val Ser Leu Gly
1               5                   10                  15

Asp Pro Ala Ser Ile Ser Cys Arg Ser Ser Gln Thr Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
                100                 105                 110

Arg Ala Asp Ala Ala Pro Thr Val Ser Thr
            115                 120

<210> SEQ ID NO 24
<211> LENGTH: 125
<212> TYPE: PRT
<213> ORGANISM: Artificial sequence
<220> FEATURE:
```

<223> OTHER INFORMATION: synthetic polypeptide

<400> SEQUENCE: 24

```
Leu Pro Glu Val Gln Leu Glu Glu Ser Gly Ala Glu Leu Val Arg Ser
1               5                   10                  15
Gly Ala Ser Val Thr Leu Ser Cys Thr Ala Ser Gly Phe Asn Ile Lys
                20                  25                  30
Asp Tyr Tyr Ile His Trp Val Lys Gln Arg Pro Glu Gln Gly Leu Glu
            35                  40                  45
Trp Ile Gly Trp Ile Asp Pro Glu Asn Gly Asp Thr Glu Tyr Ala Pro
        50                  55                  60
Lys Phe Gln Gly Lys Ala Thr Met Thr Ala Asp Thr Ser Ser Asn Thr
65                  70                  75                  80
Ala Tyr Leu Gln Leu Ser Ser Leu Thr Ser Glu Asp Thr Ala Val Tyr
                85                  90                  95
Tyr Cys Asn Gly Ala Pro Gly Tyr Trp Gly Pro Gly Thr Thr Leu Thr
            100                 105                 110
Val Ser Ser Ala Lys Thr Thr Pro Pro Ser Val Tyr Ser
        115                 120                 125
```

<210> SEQ ID NO 25
<211> LENGTH: 15
<212> TYPE: PRT
<213> ORGANISM: Artificial sequence
<220> FEATURE:
<223> OTHER INFORMATION: synthetic polypeptide

<400> SEQUENCE: 25

```
Arg Ala Ser Lys Ser Val Ser Thr Ser Asp Tyr Ser Tyr Met His
1               5                   10                  15
```

<210> SEQ ID NO 26
<211> LENGTH: 7
<212> TYPE: PRT
<213> ORGANISM: Artificial sequence
<220> FEATURE:
<223> OTHER INFORMATION: synthetic polypeptide

<400> SEQUENCE: 26

```
Leu Ala Ser Asn Leu Glu Ser
1               5
```

<210> SEQ ID NO 27
<211> LENGTH: 9
<212> TYPE: PRT
<213> ORGANISM: Artificial sequence
<220> FEATURE:
<223> OTHER INFORMATION: synthetic polypeptide

<400> SEQUENCE: 27

```
Gln His Ser Arg Glu Leu Pro Phe Thr
1               5
```

<210> SEQ ID NO 28
<211> LENGTH: 11
<212> TYPE: PRT
<213> ORGANISM: Artificial sequence
<220> FEATURE:
<223> OTHER INFORMATION: synthetic polypeptide

<400> SEQUENCE: 28

```
Ser Gly Phe Thr Phe Thr Asp Tyr Tyr Met Ser
1               5                   10
```

<210> SEQ ID NO 29
<211> LENGTH: 17
<212> TYPE: PRT
<213> ORGANISM: Artificial sequence
<220> FEATURE:
<223> OTHER INFORMATION: synthetic polypeptide

<400> SEQUENCE: 29

Asn Arg Asn Lys Thr Lys Gly Tyr Thr Thr Glu Tyr Ser Ala Ser Val
1               5                   10                  15

Lys

<210> SEQ ID NO 30
<211> LENGTH: 4
<212> TYPE: PRT
<213> ORGANISM: Artificial sequence
<220> FEATURE:
<223> OTHER INFORMATION: synthetic polypeptide

<400> SEQUENCE: 30

Gly Met Asp Tyr
1

<210> SEQ ID NO 31
<211> LENGTH: 121
<212> TYPE: PRT
<213> ORGANISM: Artificial sequence
<220> FEATURE:
<223> OTHER INFORMATION: synthetic polypeptide

<400> SEQUENCE: 31

Asp Ile Val Leu Thr Gln Ser Pro Thr Ser Leu Ala Val Ser Leu Gly
1               5                   10                  15

Gln Arg Ala Thr Ile Ser Cys Arg Ala Ser Lys Ser Val Ser Thr Ser
                20                  25                  30

Asp Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Gly Gly Thr Lys Leu Glu Ile Lys Arg
            100                 105                 110

Ala Asp Ala Ala Pro Thr Val Ser Thr
        115                 120

<210> SEQ ID NO 32
<211> LENGTH: 127
<212> TYPE: PRT
<213> ORGANISM: Artificial sequence
<220> FEATURE:
<223> OTHER INFORMATION: synthetic polypeptide

<400> SEQUENCE: 32

Leu Pro Glu Val Gln Leu Glu Glu Ser Gly Gly Gly Leu Val Gln Pro
1               5                   10                  15

Gly Gly Ser Leu Ser Leu Ser Cys Ala Ala Ser Gly Phe Thr Phe Thr
                20                  25                  30

```
Asp Tyr Tyr Met Ser Trp Val Arg Gln Pro Pro Gly Lys Ala Leu Glu
            35                  40                  45

Trp Val Ala Leu Asn Arg Asn Lys Thr Lys Gly Tyr Thr Thr Glu Tyr
 50                  55                  60

Ser Ala Ser Val Lys Gly Arg Phe Thr Ile Ser Arg Asp Asn Ser Gln
 65                  70                  75                  80

Ser Ile Leu Tyr Leu Gln Met Asn Ala Leu Arg Ala Glu Asp Ser Ala
                85                  90                  95

Thr Tyr Tyr Cys Ala Arg Gly Met Asp Tyr Trp Gly Gln Gly Thr Ser
                100                 105                 110

Val Thr Val Ser Ser Ala Lys Thr Thr Pro Pro Ser Val Tyr Ser
        115                 120                 125
```

<210> SEQ ID NO 33
<211> LENGTH: 15
<212> TYPE: PRT
<213> ORGANISM: Artificial sequence
<220> FEATURE:
<223> OTHER INFORMATION: synthetic polypeptide

<400> SEQUENCE: 33

```
Arg Ala Ser Lys Ser Val Ser Thr Ser Asp Tyr Ser Tyr Met His
 1               5                  10                  15
```

<210> SEQ ID NO 34
<211> LENGTH: 7
<212> TYPE: PRT
<213> ORGANISM: Artificial sequence
<220> FEATURE:
<223> OTHER INFORMATION: synthetic polypeptide

<400> SEQUENCE: 34

```
Leu Ala Ser Asn Leu Glu Ser
 1               5
```

<210> SEQ ID NO 35
<211> LENGTH: 9
<212> TYPE: PRT
<213> ORGANISM: Artificial sequence
<220> FEATURE:
<223> OTHER INFORMATION: synthetic polypeptide

<400> SEQUENCE: 35

```
Gln His Ser Arg Glu Leu Pro Phe Thr
 1               5
```

<210> SEQ ID NO 36
<211> LENGTH: 10
<212> TYPE: PRT
<213> ORGANISM: Artificial sequence
<220> FEATURE:
<223> OTHER INFORMATION: synthetic polypeptide

<400> SEQUENCE: 36

```
Gly Phe Thr Phe Ser Thr Tyr Pro Met Ser
 1               5                  10
```

<210> SEQ ID NO 37
<211> LENGTH: 14
<212> TYPE: PRT
<213> ORGANISM: Artificial sequence
<220> FEATURE:
<223> OTHER INFORMATION: synthetic polypeptide

<400> SEQUENCE: 37

Ser Ile Ser Asn Gly Gly Ser Thr Tyr Tyr Pro Asp Thr Val
1               5                   10

<210> SEQ ID NO 38
<211> LENGTH: 8
<212> TYPE: PRT
<213> ORGANISM: Artificial sequence
<220> FEATURE:
<223> OTHER INFORMATION: synthetic polypeptide

<400> SEQUENCE: 38

Gly Arg Asp Tyr His Phe Asp Phe
1               5

<210> SEQ ID NO 39
<211> LENGTH: 121
<212> TYPE: PRT
<213> ORGANISM: Artificial sequence
<220> FEATURE:
<223> OTHER INFORMATION: synthetic polypeptide

<400> SEQUENCE: 39

Asp Ile Val Leu Thr Gln Ser Pro Thr Ser Leu Ala Val Ser Leu Gly
1               5                   10                  15

Gln Arg Ala Thr Ile Ser Cys Arg Ala Ser Lys Ser Val Ser Thr Ser
            20                  25                  30

Asp Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Gly Gly Thr Lys Leu Glu Ile Lys Arg
            100                 105                 110

Ala Asp Ala Ala Pro Thr Val Ser Thr
        115                 120

<210> SEQ ID NO 40
<211> LENGTH: 128
<212> TYPE: PRT
<213> ORGANISM: Artificial sequence
<220> FEATURE:
<223> OTHER INFORMATION: synthetic polypeptide

<400> SEQUENCE: 40

Leu Pro Glu Val Gln Leu Glu Glu Ser Gly Gly Gly Leu Val Lys Pro
1               5                   10                  15

Gly Gly Ser Leu Lys Leu Ser Cys Ala Ala Ser Gly Phe Thr Phe Ser
            20                  25                  30

Thr Tyr Pro Met Ser Trp Val Arg Gln Thr Pro Glu Lys Arg Leu Glu
        35                  40                  45

Trp Val Ala Ser Ile Ser Asn Gly Gly Ser Thr Tyr Tyr Pro Asp Thr
    50                  55                  60

Val Lys Gly Arg Phe Thr Ile Ser Arg Asp Asn Ala Arg Asn Ile Leu
65                  70                  75                  80

Tyr Leu Gln Met Ser Ser Leu Arg Ser Glu Asp Thr Ala Met Tyr Tyr
                85                  90                  95

-continued

Cys Ala Arg Gly Arg Asp Tyr His Phe Asp Phe Trp Gly Gln Gly Thr
             100                 105                 110

Thr Leu Thr Val Ser Ser Ala Lys Thr Thr Pro Pro Ser Val Tyr Ser
        115                 120                 125

<210> SEQ ID NO 41
<211> LENGTH: 16
<212> TYPE: PRT
<213> ORGANISM: Artificial sequence
<220> FEATURE:
<223> OTHER INFORMATION: synthetic polypeptide

<400> SEQUENCE: 41

Lys Ser Ser Gln Ser Leu Leu Tyr Ser Asp Gly Lys Thr Phe Leu Asn
1               5                   10                  15

<210> SEQ ID NO 42
<211> LENGTH: 7
<212> TYPE: PRT
<213> ORGANISM: Artificial sequence
<220> FEATURE:
<223> OTHER INFORMATION: synthetic polypeptide

<400> SEQUENCE: 42

Leu Val Ser Lys Leu Gln Ser
1               5

<210> SEQ ID NO 43
<211> LENGTH: 9
<212> TYPE: PRT
<213> ORGANISM: Artificial sequence
<220> FEATURE:
<223> OTHER INFORMATION: synthetic polypeptide

<400> SEQUENCE: 43

Val Gln Gly Thr His Phe Pro Tyr Thr
1               5

<210> SEQ ID NO 44
<211> LENGTH: 10
<212> TYPE: PRT
<213> ORGANISM: Artificial sequence
<220> FEATURE:
<223> OTHER INFORMATION: synthetic polypeptide

<400> SEQUENCE: 44

Gly Tyr Thr Phe Thr Asn Tyr Trp Ile Asn
1               5                   10

<210> SEQ ID NO 45
<211> LENGTH: 16
<212> TYPE: PRT
<213> ORGANISM: Artificial sequence
<220> FEATURE:
<223> OTHER INFORMATION: synthetic polypeptide

<400> SEQUENCE: 45

Ile Tyr Pro Gly Ser Thr Arg Ala Asn Tyr Asn Glu Lys Phe Lys Ser
1               5                   10                  15

<210> SEQ ID NO 46
<211> LENGTH: 4
<212> TYPE: PRT
<213> ORGANISM: Artificial sequence
<220> FEATURE:
<223> OTHER INFORMATION: synthetic polypeptide

<400> SEQUENCE: 46

Thr His Ser Ile
1

<210> SEQ ID NO 47
<211> LENGTH: 122
<212> TYPE: PRT
<213> ORGANISM: Artificial sequence
<220> FEATURE:
<223> OTHER INFORMATION: synthetic polypeptide

<400> SEQUENCE: 47

Asp Ile Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Phe Leu Asn Trp Leu Leu Gln Ser Pro Gly Gln Ser
        35                  40                  45

Pro Arg Leu Leu Ile Tyr Leu Val Ser Lys Leu Gln Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110

Arg Ala Asp Ala Ala Pro Thr Val Ser Thr
        115                 120

<210> SEQ ID NO 48
<211> LENGTH: 125
<212> TYPE: PRT
<213> ORGANISM: Artificial sequence
<220> FEATURE:
<223> OTHER INFORMATION: synthetic polypeptide

<400> SEQUENCE: 48

Leu Pro Gln Val Gln Leu Glu Glu Ser Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Asn Tyr Trp Ile Asn Trp Val Lys Gln Arg Pro Gly Gln Gly Leu Glu
        35                  40                  45

Trp Ile Gly Asn Ile Tyr Pro Gly Ser Thr Arg Ala Asn Tyr Asn Glu
    50                  55                  60

Lys Phe Lys Ser Lys Ala Thr Leu Thr Val Asp Thr Ser Ser Ser Thr
65                  70                  75                  80

Ala Tyr Met Gln Val Ser Ser Leu Thr Ser Asp Asp Ser Ala Val Tyr
                85                  90                  95

Tyr Cys Thr Arg Thr His Ser Ile Trp Gly Gln Gly Thr Gln Val Thr
            100                 105                 110

Val Ser Ala Ala Lys Thr Thr Pro Pro Ser Val Tyr Ser
        115                 120                 125

<210> SEQ ID NO 49
<211> LENGTH: 16
<212> TYPE: PRT
<213> ORGANISM: Artificial sequence
<220> FEATURE:

<223> OTHER INFORMATION: synthetic polypeptide

<400> SEQUENCE: 49

Lys Ser Ser Gln Ser Leu Leu Tyr Ser Asp Gly Lys Thr Tyr Leu Asn
1               5                   10                  15

<210> SEQ ID NO 50
<211> LENGTH: 7
<212> TYPE: PRT
<213> ORGANISM: Artificial sequence
<220> FEATURE:
<223> OTHER INFORMATION: synthetic polypeptide

<400> SEQUENCE: 50

Gln Val Ser Lys Leu Asp Pro
1               5

<210> SEQ ID NO 51
<211> LENGTH: 9
<212> TYPE: PRT
<213> ORGANISM: Artificial sequence
<220> FEATURE:
<223> OTHER INFORMATION: synthetic polypeptide

<400> SEQUENCE: 51

Leu Gln Gly Thr Tyr Tyr Pro His Thr
1               5

<210> SEQ ID NO 52
<211> LENGTH: 10
<212> TYPE: PRT
<213> ORGANISM: Artificial sequence
<220> FEATURE:
<223> OTHER INFORMATION: synthetic polypeptide

<400> SEQUENCE: 52

Gly Tyr Thr Phe Ile Ser Asn Trp Met His
1               5                   10

<210> SEQ ID NO 53
<211> LENGTH: 16
<212> TYPE: PRT
<213> ORGANISM: Artificial sequence
<220> FEATURE:
<223> OTHER INFORMATION: synthetic polypeptide

<400> SEQUENCE: 53

Ile Asp Pro Ser Asp Ser Glu Thr His Tyr Asn Gln Lys Phe Lys Asp
1               5                   10                  15

<210> SEQ ID NO 54
<211> LENGTH: 10
<212> TYPE: PRT
<213> ORGANISM: Artificial sequence
<220> FEATURE:
<223> OTHER INFORMATION: synthetic polypeptide

<400> SEQUENCE: 54

Arg Asp Arg Asp Gly Tyr Tyr Phe Asp Tyr
1               5                   10

<210> SEQ ID NO 55
<211> LENGTH: 122
<212> TYPE: PRT
<213> ORGANISM: Artificial sequence
<220> FEATURE:
<223> OTHER INFORMATION: synthetic polypeptide

<400> SEQUENCE: 55

Asp Ile Val Met Thr Gln Ser Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Leu Gln Gln Arg Pro Gly Gln Ser
        35                  40                  45

Pro Lys Arg Leu Val Tyr Gln Val Ser Lys Leu Asp Pro Gly Ile Pro
    50                  55                  60

Asp Arg Phe Ser Gly Ser Gly Ser Glu Thr Asp Phe Thr Leu Lys Leu
65                  70                  75                  80

Ser Arg Val Glu Ala Glu Asp Leu Gly Val Tyr Tyr Cys Leu Gln Gly
                85                  90                  95

Thr Tyr Tyr Pro His Thr Phe Gly Gly Thr Lys Leu Glu Ile Lys
            100                 105                 110

Arg Ala Asp Ala Ala Pro Thr Val Ser Thr
        115                 120

<210> SEQ ID NO 56
<211> LENGTH: 131
<212> TYPE: PRT
<213> ORGANISM: Artificial sequence
<220> FEATURE:
<223> OTHER INFORMATION: synthetic polypeptide

<400> SEQUENCE: 56

Leu Pro Glu Val Lys Leu Glu Glu Ser Gly Ala Glu Leu Val Lys Pro
1               5                   10                  15

Gly Ala Ser Val Lys Leu Ser Cys Lys Ala Ser Gly Tyr Thr Phe Ile
            20                  25                  30

Ser Asn Trp Met His Trp Val Lys Gln Arg Pro Gly Gln Gly Leu Glu
        35                  40                  45

Trp Ile Gly Asn Ile Asp Pro Ser Asp Ser Glu Thr His Tyr Asn Gln
    50                  55                  60

Lys Phe Lys Asp Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Arg Asp Arg Asp Gly Tyr Tyr Phe Asp Tyr Trp Gly
            100                 105                 110

Gln Gly Thr Thr Leu Thr Val Ser Ser Ala Lys Thr Thr Pro Pro Ser
        115                 120                 125

Val Tyr Ser
    130

<210> SEQ ID NO 57
<211> LENGTH: 16
<212> TYPE: PRT
<213> ORGANISM: Artificial sequence
<220> FEATURE:
<223> OTHER INFORMATION: synthetic polypeptide

<400> SEQUENCE: 57

Lys Ser Ser Gln Ser Leu Leu Tyr Ser Asp Gly Lys Thr Tyr Leu Asn
1               5                   10                  15

<210> SEQ ID NO 58

```
<211> LENGTH: 7
<212> TYPE: PRT
<213> ORGANISM: Artificial sequence
<220> FEATURE:
<223> OTHER INFORMATION: synthetic polypeptide

<400> SEQUENCE: 58

Gln Val Ser Lys Leu Asp Pro
1               5

<210> SEQ ID NO 59
<211> LENGTH: 8
<212> TYPE: PRT
<213> ORGANISM: Artificial sequence
<220> FEATURE:
<223> OTHER INFORMATION: synthetic polypeptide

<400> SEQUENCE: 59

Leu Gln Gly Thr Tyr Tyr Pro His
1               5

<210> SEQ ID NO 60
<211> LENGTH: 10
<212> TYPE: PRT
<213> ORGANISM: Artificial sequence
<220> FEATURE:
<223> OTHER INFORMATION: synthetic polypeptide

<400> SEQUENCE: 60

Gly Tyr Thr Phe Thr Asn Tyr Trp Ile Asn
1               5                   10

<210> SEQ ID NO 61
<211> LENGTH: 15
<212> TYPE: PRT
<213> ORGANISM: Artificial sequence
<220> FEATURE:
<223> OTHER INFORMATION: synthetic polypeptide

<400> SEQUENCE: 61

Ile Tyr Pro Gly Ser Thr Arg Ala Asn Tyr Asn Glu Lys Phe Lys
1               5                   10                  15

<210> SEQ ID NO 62
<211> LENGTH: 4
<212> TYPE: PRT
<213> ORGANISM: Artificial sequence
<220> FEATURE:
<223> OTHER INFORMATION: synthetic polypeptide

<400> SEQUENCE: 62

Thr His Ser Ile
1

<210> SEQ ID NO 63
<211> LENGTH: 122
<212> TYPE: PRT
<213> ORGANISM: Artificial sequence
<220> FEATURE:
<223> OTHER INFORMATION: synthetic polypeptide

<400> SEQUENCE: 63

Asp Ile Val Ile Thr Gln Ser Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30
```

Asp Gly Lys Thr Tyr Leu Asn Trp Leu Gln Gln Arg Pro Gly Gln Ser
            35                  40                  45

Pro Lys Arg Leu Val Tyr Gln Val Ser Lys Leu Asp Pro Gly Ile Pro
        50                  55                  60

Asp Arg Phe Ser Gly Ser Gly Ser Glu Thr Asp Phe Thr Leu Lys Leu
65                  70                  75                  80

Ser Arg Val Glu Ala Glu Asp Leu Gly Val Tyr Tyr Cys Leu Gln Gly
                85                  90                  95

Thr Tyr Tyr Pro His Thr Phe Gly Gly Gly Thr Lys Leu Glu Ile Lys
            100                 105                 110

Arg Ala Asp Ala Ala Pro Thr Val Ser Thr
            115                 120

<210> SEQ ID NO 64
<211> LENGTH: 125
<212> TYPE: PRT
<213> ORGANISM: Artificial sequence
<220> FEATURE:
<223> OTHER INFORMATION: synthetic polypeptide

<400> SEQUENCE: 64

Leu Pro Glu Val Lys Leu Glu Gln Ser Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Asn Tyr Trp Ile Asn Trp Val Lys Gln Arg Pro Gly Gln Gly Leu Glu
            35                  40                  45

Trp Ile Gly Asn Ile Tyr Pro Gly Ser Thr Arg Ala Asn Tyr Asn Glu
        50                  55                  60

Lys Phe Lys Ser Lys Ala Thr Leu Thr Val Asp Thr Ser Ser Ser Thr
65                  70                  75                  80

Ala Tyr Met Gln Val Ser Ser Leu Thr Ser Asp Asp Ser Ala Val Tyr
                85                  90                  95

Tyr Cys Thr Arg Thr His Ser Ile Trp Gly Gln Gly Thr Gln Val Thr
            100                 105                 110

Val Ser Ala Ala Lys Thr Thr Pro Pro Ser Val Tyr Ser
            115                 120                 125

<210> SEQ ID NO 65
<211> LENGTH: 11
<212> TYPE: PRT
<213> ORGANISM: Artificial sequence
<220> FEATURE:
<223> OTHER INFORMATION: synthetic polypeptide

<400> SEQUENCE: 65

Lys Ala Ser Gln Asp Ile Asn Lys Tyr Ile Ala
1               5                   10

<210> SEQ ID NO 66
<211> LENGTH: 7
<212> TYPE: PRT
<213> ORGANISM: Artificial sequence
<220> FEATURE:
<223> OTHER INFORMATION: synthetic polypeptide

<400> SEQUENCE: 66

Tyr Thr Ser Thr Leu Gln Ser
1               5

<210> SEQ ID NO 67
<211> LENGTH: 8
<212> TYPE: PRT
<213> ORGANISM: Artificial sequence
<220> FEATURE:
<223> OTHER INFORMATION: synthetic polypeptide

<400> SEQUENCE: 67

Leu Gln Tyr Asp His Leu Leu Thr
1               5

<210> SEQ ID NO 68
<211> LENGTH: 10
<212> TYPE: PRT
<213> ORGANISM: Artificial sequence
<220> FEATURE:
<223> OTHER INFORMATION: synthetic polypeptide

<400> SEQUENCE: 68

Gly Tyr Thr Phe Ile Ser Asn Trp Met His
1               5                   10

<210> SEQ ID NO 69
<211> LENGTH: 17
<212> TYPE: PRT
<213> ORGANISM: Artificial sequence
<220> FEATURE:
<223> OTHER INFORMATION: synthetic polypeptide

<400> SEQUENCE: 69

Asn Ile Asp Pro Ser Asp Ser Glu Thr His Tyr Asn Gln Lys Phe Lys
1               5                   10                  15

Asp

<210> SEQ ID NO 70
<211> LENGTH: 10
<212> TYPE: PRT
<213> ORGANISM: Artificial sequence
<220> FEATURE:
<223> OTHER INFORMATION: synthetic polypeptide

<400> SEQUENCE: 70

Arg Asp Arg Asp Gly Tyr Tyr Phe Asp Tyr
1               5                   10

<210> SEQ ID NO 71
<211> LENGTH: 116
<212> TYPE: PRT
<213> ORGANISM: Artificial sequence
<220> FEATURE:
<223> OTHER INFORMATION: synthetic polypeptide

<400> SEQUENCE: 71

Asp Ile Val Leu Thr Gln Thr Pro Ser Ser Leu Ser Ala Ser Leu Gly
1               5                   10                  15

Gly Lys Val Thr Ile Thr Cys Lys Ala Ser Gln Asp Ile Asn Lys Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Ser Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp His Leu Leu Thr

```
                85                  90                  95
Phe Gly Ala Gly Thr Lys Leu Glu Leu Lys Arg Ala Asp Ala Ala Pro
                100                 105                 110

Thr Val Ser Thr
        115

<210> SEQ ID NO 72
<211> LENGTH: 131
<212> TYPE: PRT
<213> ORGANISM: Artificial sequence
<220> FEATURE:
<223> OTHER INFORMATION: synthetic polypeptide

<400> SEQUENCE: 72

Leu Pro Glu Val Gln Leu Glu Gln Ser Gly Ala Glu Leu Val Lys Pro
1               5                   10                  15

Gly Ala Ser Val Lys Leu Ser Cys Lys Ala Ser Gly Tyr Thr Phe Ile
                20                  25                  30

Ser Asn Trp Met His Trp Val Lys Gln Arg Pro Gly Gln Gly Leu Glu
            35                  40                  45

Trp Ile Gly Asn Ile Asp Pro Ser Asp Ser Glu Thr His Tyr Asn Gln
        50                  55                  60

Lys Phe Lys Asp Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Arg Asp Arg Asp Gly Tyr Tyr Phe Asp Tyr Trp Gly
                100                 105                 110

Gln Gly Thr Thr Leu Thr Val Ser Ser Ala Lys Thr Thr Pro Pro Ser
            115                 120                 125

Val Tyr Ser
        130

<210> SEQ ID NO 73
<211> LENGTH: 180
<212> TYPE: PRT
<213> ORGANISM: Homo sapiens

<400> SEQUENCE: 73

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
                100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
        130                 135                 140
```

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser
            180

<210> SEQ ID NO 74
<211> LENGTH: 9
<212> TYPE: PRT
<213> ORGANISM: Artificial sequence
<220> FEATURE:
<223> OTHER INFORMATION: synthetic polypeptide

<400> SEQUENCE: 74

Tyr Pro Tyr Asp Val Pro Asp Tyr Ala
1               5

<210> SEQ ID NO 75
<211> LENGTH: 8
<212> TYPE: PRT
<213> ORGANISM: Artificial sequence
<220> FEATURE:
<223> OTHER INFORMATION: synthetic polypeptide

<400> SEQUENCE: 75

Asp Tyr Lys Asp Asp Asp Asp Lys
1               5

<210> SEQ ID NO 76
<211> LENGTH: 10
<212> TYPE: PRT
<213> ORGANISM: Artificial sequence
<220> FEATURE:
<223> OTHER INFORMATION: synthetic polypeptide

<400> SEQUENCE: 76

Glu Gln Lys Leu Ile Ser Glu Glu Asp Leu
1               5                   10

<210> SEQ ID NO 77
<211> LENGTH: 11
<212> TYPE: PRT
<213> ORGANISM: Artificial sequence
<220> FEATURE:
<223> OTHER INFORMATION: synthetic polypeptide

<400> SEQUENCE: 77

Ser Leu Pro Thr Pro Pro Thr Arg Glu Pro Lys
1               5                   10

<210> SEQ ID NO 78
<211> LENGTH: 11
<212> TYPE: PRT
<213> ORGANISM: Artificial sequence
<220> FEATURE:
<223> OTHER INFORMATION: synthetic polypeptide

<400> SEQUENCE: 78

Arg Ile Pro Ala Lys Thr Pro Pro Ala Pro Lys
1               5                   10

<210> SEQ ID NO 79
<211> LENGTH: 12
<212> TYPE: PRT

```
<213> ORGANISM: Artificial sequence
<220> FEATURE:
<223> OTHER INFORMATION: synthetic polypeptide

<400> SEQUENCE: 79

Glu Asp Glu Ala Ala Gly His Val Thr Gln Ala Arg
1               5                   10

<210> SEQ ID NO 80
<211> LENGTH: 12
<212> TYPE: PRT
<213> ORGANISM: Artificial sequence
<220> FEATURE:
<223> OTHER INFORMATION: synthetic polypeptide

<400> SEQUENCE: 80

Ser Ser Pro Gly Ser Pro Gly Thr Pro Gly Ser Arg
1               5                   10

<210> SEQ ID NO 81
<211> LENGTH: 5
<212> TYPE: PRT
<213> ORGANISM: Artificial sequence
<220> FEATURE:
<223> OTHER INFORMATION: synthetic polypeptide

<400> SEQUENCE: 81

His His His His His
1               5

<210> SEQ ID NO 82
<211> LENGTH: 6
<212> TYPE: PRT
<213> ORGANISM: Artificial sequence
<220> FEATURE:
<223> OTHER INFORMATION: synthetic polypeptide

<400> SEQUENCE: 82

His His His His His His
1               5

<210> SEQ ID NO 83
<211> LENGTH: 8
<212> TYPE: PRT
<213> ORGANISM: Artificial sequence
<220> FEATURE:
<223> OTHER INFORMATION: synthetic polypeptide

<400> SEQUENCE: 83

Trp Ser His Pro Gln Phe Glu Lys
1               5

<210> SEQ ID NO 84
<211> LENGTH: 5
<212> TYPE: PRT
<213> ORGANISM: Artificial sequence
<220> FEATURE:
<223> OTHER INFORMATION: synthetic polypeptide

<400> SEQUENCE: 84

Arg Tyr Ile Arg Ser
1               5

<210> SEQ ID NO 85
<211> LENGTH: 4
<212> TYPE: PRT
<213> ORGANISM: Artificial sequence
```

<220> FEATURE:
<223> OTHER INFORMATION: synthetic polypeptide

<400> SEQUENCE: 85

Phe His His Thr
1

<210> SEQ ID NO 86
<211> LENGTH: 17
<212> TYPE: PRT
<213> ORGANISM: Artificial sequence
<220> FEATURE:
<223> OTHER INFORMATION: synthetic polypeptide

<400> SEQUENCE: 86

Trp Glu Ala Ala Ala Arg Glu Ala Cys Cys Arg Glu Cys Cys Ala Arg
1               5                   10                  15

Ala

<210> SEQ ID NO 87
<211> LENGTH: 4
<212> TYPE: PRT
<213> ORGANISM: Artificial sequence
<220> FEATURE:
<223> OTHER INFORMATION: synthetic polypeptide

<400> SEQUENCE: 87

Gly Gly Ser Gly
1

<210> SEQ ID NO 88
<211> LENGTH: 5
<212> TYPE: PRT
<213> ORGANISM: Artificial sequence
<220> FEATURE:
<223> OTHER INFORMATION: synthetic polypeptide

<400> SEQUENCE: 88

Gly Gly Ser Gly Gly
1               5

<210> SEQ ID NO 89
<211> LENGTH: 5
<212> TYPE: PRT
<213> ORGANISM: Artificial sequence
<220> FEATURE:
<223> OTHER INFORMATION: synthetic polypeptide

<400> SEQUENCE: 89

Gly Ser Gly Ser Gly
1               5

<210> SEQ ID NO 90
<211> LENGTH: 5
<212> TYPE: PRT
<213> ORGANISM: Artificial sequence
<220> FEATURE:
<223> OTHER INFORMATION: synthetic polypeptide

<400> SEQUENCE: 90

Gly Ser Gly Gly Gly
1               5

<210> SEQ ID NO 91
<211> LENGTH: 5
<212> TYPE: PRT

```
<213> ORGANISM: Artificial sequence
<220> FEATURE:
<223> OTHER INFORMATION: synthetic polypeptide

<400> SEQUENCE: 91

Gly Gly Gly Ser Gly
1               5

<210> SEQ ID NO 92
<211> LENGTH: 5
<212> TYPE: PRT
<213> ORGANISM: Artificial sequence
<220> FEATURE:
<223> OTHER INFORMATION: synthetic polypeptide

<400> SEQUENCE: 92

Gly Ser Ser Ser Gly
1               5

<210> SEQ ID NO 93
<211> LENGTH: 12
<212> TYPE: PRT
<213> ORGANISM: Artificial sequence
<220> FEATURE:
<223> OTHER INFORMATION: synthetic polypeptide

<400> SEQUENCE: 93

Cys Ser Leu Pro Thr Pro Pro Thr Arg Glu Pro Lys
1               5                   10

<210> SEQ ID NO 94
<211> LENGTH: 20
<212> TYPE: PRT
<213> ORGANISM: Artificial sequence
<220> FEATURE:
<223> OTHER INFORMATION: synthetic polypeptide

<400> SEQUENCE: 94

Cys Ser Leu Pro Thr Pro Pro Thr Arg Glu Pro Lys Lys Val Ala Val
1               5                   10                  15

Val Arg Thr Pro
            20

<210> SEQ ID NO 95
<211> LENGTH: 13
<212> TYPE: PRT
<213> ORGANISM: Artificial sequence
<220> FEATURE:
<223> OTHER INFORMATION: synthetic polypeptide

<400> SEQUENCE: 95

Cys Ser Ser Pro Gly Ser Pro Gly Thr Pro Gly Ser Arg
1               5                   10

<210> SEQ ID NO 96
<211> LENGTH: 19
<212> TYPE: PRT
<213> ORGANISM: Artificial sequence
<220> FEATURE:
<223> OTHER INFORMATION: synthetic polypeptide

<400> SEQUENCE: 96

Cys Ser Ser Pro Gly Ser Pro Gly Thr Pro Gly Ser Arg Ser Arg Thr
1               5                   10                  15

Pro Ser Leu
```

```
<210> SEQ ID NO 97
<211> LENGTH: 12
<212> TYPE: PRT
<213> ORGANISM: Artificial sequence
<220> FEATURE:
<223> OTHER INFORMATION: synthetic polypeptide

<400> SEQUENCE: 97

Cys Arg Ile Pro Ala Lys Thr Pro Pro Ala Pro Lys
1               5                   10

<210> SEQ ID NO 98
<211> LENGTH: 17
<212> TYPE: PRT
<213> ORGANISM: Artificial sequence
<220> FEATURE:
<223> OTHER INFORMATION: synthetic polypeptide

<400> SEQUENCE: 98

Cys Arg Ile Pro Ala Lys Thr Pro Pro Ala Pro Lys Thr Pro Pro Ser
1               5                   10                  15

Ser

<210> SEQ ID NO 99
<211> LENGTH: 13
<212> TYPE: PRT
<213> ORGANISM: Artificial sequence
<220> FEATURE:
<223> OTHER INFORMATION: synthetic polypeptide

<400> SEQUENCE: 99

Cys Glu Asp Glu Ala Ala Gly His Val Thr Gln Ala Arg
1               5                   10

<210> SEQ ID NO 100
<211> LENGTH: 18
<212> TYPE: PRT
<213> ORGANISM: Artificial sequence
<220> FEATURE:
<223> OTHER INFORMATION: synthetic polypeptide

<400> SEQUENCE: 100

Cys Glu Asp Glu Ala Ala Gly His Val Thr Gln Ala Arg Met Val Ser
1               5                   10                  15

Lys Ser
```

TAU PEPTIDES, ANTI-TAU ANTIBODIES, AND METHODS OF USE THEREOF

CROSS REFERENCE TO RELATED APPLICATIONS

This application is a 35 U.S.C. 371 national stage filing of International Application No. PCT/US2014/016597, filed on Feb. 14, 2014. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 8, 2016, is named MXI-605US_SL.txt and is 50355 bytes in size.

INTRODUCTION

The microtubule associated protein tau is abundant in the central nervous system and is produced primarily by neurons. The primary function of tau is to stabilize microtubules. Six tau isoforms exist in the adult human brain; tau isoforms are the products of alternative splicing of a single gene.

Tauopathies are a class of neurodegenerative diseases resulting from the pathological aggregation of tau protein in so-called neurofibrillary tangles (NFT) in the brain. Some examples of tauopathies include frontotemporal dementia (FTD), Alzheimer's disease, progressive supranuclear palsy, corticobasal degeneration, and frontotemporal lobar degeneration.

There is a need in the art for methods of detecting and treating tauopathies, and for reagents suitable for use in such methods.

SUMMARY

The present disclosure provides isolated tau peptides, and compositions comprising the peptides. The present disclosure provides antibodies specific for an isolated tau peptide. The antibodies find use in diagnostic and treatment methods, which are also provided.

Features

The present disclosure provides a pharmaceutical composition comprising: a) an isolated tau peptide, wherein the tau peptide comprises an amino acid sequence having at least about 95% amino acid sequence identity to the amino acid sequence set forth in any one of SEQ ID NOs:1-3, wherein the tau peptide has a length of from about 5 amino acids to about 175 amino acids; and b) a pharmaceutically acceptable excipient.

The present disclosure provides a pharmaceutical composition comprising: a) isolated tau peptide, wherein the tau peptide comprises an amino acid sequence having at least about 95% amino acid sequence identity to the amino acid sequence set forth in SEQ ID NO:4, wherein the tau peptide has a length of from about 5 amino acids to about 150 amino acids; and b) a pharmaceutically acceptable excipient.

The present disclosure provides a pharmaceutical composition comprising: a) isolated tau peptide, wherein the tau peptide comprises an amino acid sequence having at least about 95% amino acid sequence identity to the amino acid sequence set forth in SEQ ID NO:5, wherein the tau peptide has a length of from about 5 amino acids to about 121 amino acids; and b) a pharmaceutically acceptable excipient.

The present disclosure provides a pharmaceutical composition comprising: a) isolated tau peptide, wherein the tau peptide comprises an amino acid sequence having at least about 95% amino acid sequence identity to the amino acid sequence set forth in SEQ ID NO:5, wherein the tau peptide has a length of from about 5 amino acids to about 67 amino acids; and b) a pharmaceutically acceptable excipient.

In any of the pharmaceutical compositions described above or elsewhere herein, the tau peptide can at least one acetylated amino acid; for example, in some cases, the at least one acetylated amino acid is an acetylated N-terminal amino acid. In any of these pharmaceutical compositions, the tau peptide can comprise a phosphorylated serine residue and/or a phosphorylated threonine residue. In any of these pharmaceutical compositions, the tau peptide can comprise a non-peptide isosteric linkage and/or a non-natural amino acid; for example, the non-natural amino acid can be a D-amino acid. In any of these pharmaceutical compositions, the tau peptide can be hypophosphorylated compared to an intracellular tau peptide of the same amino acid sequence. In any of these pharmaceutical compositions, the tau peptide can be immobilized on a solid support; for example, the solid support can be a bead, a test strip, or a well of a multi-well plate. In any of these pharmaceutical compositions, the tau peptide can comprise a detectable label; for example, the detectable label can be a chemiluminescent agent, a particulate label, a colorimetric agent, an energy transfer agent, an enzyme, a fluorescent agent, a contrast agent, or a radioisotope. In any of these pharmaceutical compositions, the compositions can further include an adjuvant. The adjuvant can be one that is suitable for use in a human. In any of these pharmaceutical compositions, the composition can be sterile. In any of these pharmaceutical compositions, the composition can be endotoxin free.

The present disclosure provides a detectably labeled isolated tau peptide, wherein the tau peptide comprises: a) an amino acid sequence having at least about 95% amino acid sequence identity to the amino acid sequence set forth in any one of SEQ ID NOs:1-3, wherein the tau peptide has a length of from about 5 amino acids to about 175 amino acids; b) an amino acid sequence having at least about 95% amino acid sequence identity to the amino acid sequence set forth in SEQ ID NO:4, wherein the tau peptide has a length of from about 5 amino acids to about 150 amino acids; c) an amino acid sequence having at least about 95% amino acid sequence identity to the amino acid sequence set forth in SEQ ID NO:5, wherein the tau peptide has a length of from about 5 amino acids to about 121 amino acids; or d) an amino acid sequence having at least about 95% amino acid sequence identity to the amino acid sequence set forth in SEQ ID NO:5, wherein the tau peptide has a length of from about 5 amino acids to about 67 amino acids.

The present disclosure provides a method of generating an antibody specific for a tau peptide, the method comprising: a) administering the peptide to a non-human mammal, wherein the peptide comprises: i) an amino acid sequence having at least about 95% amino acid sequence identity to the amino acid sequence set forth in any one of SEQ ID NOs:1-3, wherein the tau peptide has a length of from about 5 amino acids to about 175 amino acids; ii) an amino acid sequence having at least about 95% amino acid sequence identity to the amino acid sequence set forth in SEQ ID NO:4, wherein the tau peptide has a length of from about 5 amino acids to about 150 amino acids; iii) an amino acid sequence having at least about 95% amino acid sequence identity to the amino acid sequence set forth in SEQ ID NO:5, wherein the tau peptide has a length of from about 5 amino acids to about 121 amino acids; or iv) an amino acid sequence having at least about 95% amino acid sequence identity to the amino acid sequence set forth in SEQ ID NO:5, wherein the tau peptide has a length of from about 5 amino acids to about 67 amino acids, wherein said administering induces production of antibody to the peptide; and b) isolating the antibody and/or a cell producing the antibody from the mammal.

The present disclosure provides a method of stimulating an immune response in an individual to a tau peptide, the method comprising administering a subject pharmaceutical composition comprising an eTau polypeptide (e.g., a pharmaceutical composition as described above or elsewhere herein) to the individual, wherein said administering stimulates an immune response to the peptide in the individual. In some cases, the immune response comprises production of antibody specific for tau. In some cases, the immune response results in a change in one or more of: a) the amount of free extracellular tau in brain tissue; b) the amount of free extracellular tau in interstitial fluid (ISF); c) the amount of free extracellular tau in cerebrospinal fluid (CSF); d) the neuron-to-neuron spread of tau; e) the amount of intraneuron tau aggregates; f) the degree of microglial and/or astrocyte activation; g) the amount of phosphorylated or hyperphosphorylated tau; h) the amount of total Tau or free tau in ISF or CSF; i) the amount of intracellular N-terminal tau fragments; j) neuronal hyperactivity; k) the amount of Aβ40 and/or Aβ42 in CSF; l) the Aβ plaque burden; m) secretion of Aβ40 and/or Aβ42 from a neuron; n) amyloid precursor protein (APP) promoter activity; o) APP mRNA and/or protein level; p) the activity of beta-secretase and/or gamma secretase; q) the activation state of an Aβ induced signaling pathway; r) the amount of intracellular total tau or free tau; s) the amount of anti-tau antibody-bound tau in ISF or CSF; and t) the amount of intracellular anti-Tau antibody-bound tau.

The present disclosure provides a recombinant expression vector comprising a nucleotide sequence encoding a tau peptide, wherein the tau peptide comprises: a) an amino acid sequence having at least about 95% amino acid sequence identity to the amino acid sequence set forth in any one of SEQ ID NOs:1-3, wherein the tau peptide has a length of from about 5 amino acids to about 175 amino acids; b) an amino acid sequence having at least about 95% amino acid sequence identity to the amino acid sequence set forth in SEQ ID NO:4, wherein the tau peptide has a length of from about 5 amino acids to about 150 amino acids; c) an amino acid sequence having at least about 95% amino acid sequence identity to the amino acid sequence set forth in SEQ ID NO:5, wherein the tau peptide has a length of from about 5 amino acids to about 121 amino acids; or d) an amino acid sequence having at least about 95% amino acid sequence identity to the amino acid sequence set forth in SEQ ID NO:5, wherein the tau peptide has a length of from about 5 amino acids to about 67 amino acids. In some cases, the nucleotide sequence is operably linked to a transcriptional control element. The present disclosure provides a genetically modified host cell comprising any of the above-listed recombinant vectors.

The present disclosure provides an isolated monoclonal antibody that specifically binds an epitope within an extracellular Tau (eTau) polypeptide. In some cases, the eTau polypeptide comprises: a) an amino acid sequence having at least about 95% amino acid sequence identity to the amino acid sequence set forth in any one of SEQ ID NOs:1-3, wherein the tau peptide has a length of from about 5 amino acids to about 175 amino acids; b) an amino acid sequence having at least about 95% amino acid sequence identity to the amino acid sequence set forth in SEQ ID NO:4, wherein the tau peptide has a length of from about 5 amino acids to about 150 amino acids; c) an amino acid sequence having at least about 95% amino acid sequence identity to the amino acid sequence set forth in SEQ ID NO:5, wherein the tau peptide has a length of from about 5 amino acids to about 121 amino acids; or d) an amino acid sequence having at least about 95% amino acid sequence identity to the amino acid sequence set forth in SEQ ID NO:5, wherein the tau peptide has a length of from about 5 amino acids to about 67 amino acids. In some cases, the epitope is a linear epitope. In some cases, the epitope is a neoepitope at the C-terminus of the peptide. In some cases, the epitope is in a C-terminal region of the peptide. In some cases, the antibody binds specifically to the epitope independently of phosphorylation of amino acids within the epitope. In some cases, the epitope does not comprise a phosphorylated amino acid. In some cases, the epitope comprises a phosphorylated amino acid, a nitrated amino acid, or both a phosphorylated amino acid and a nitrated amino acid. In some cases, the antibody is humanized. In some cases, the antibody comprises a humanized light chain framework. In some cases, the antibody comprises a humanized heavy chain framework. In some cases, the antibody comprises a humanized light chain framework and a humanized heavy chain framework.

In any of the antibodies described above or elsewhere herein, the antibody can comprise: a) a VL region comprising one or more complementarity determining regions (CDRs) selected from SEQ ID NO:9, SEQ ID NO:10, and SEQ ID NO:11; and/or b) a VH region comprising one or more complementarity determining regions (CDRs) selected from SEQ ID NO:12, SEQ ID NO:13, and SEQ ID NO:14. In any of the antibodies described above or elsewhere herein, the antibody can comprise: a) a VL region comprising one or more complementarity determining regions (CDRs) selected from SEQ ID NO:17, SEQ ID NO:18, and SEQ ID NO:19; and/or b) a VH region comprising one or more complementarity determining regions (CDRs) selected from SEQ ID NO:20, SEQ ID NO:21, and SEQ ID NO:22. In any of the antibodies described above or elsewhere herein, the antibody can comprise: a) a VL region comprising one or more complementarity determining regions (CDRs) selected from SEQ ID NO:65, SEQ ID NO:66, and SEQ ID NO:67; and/or b) a VH region comprising one or more complementarity determining regions (CDRs) selected from SEQ ID NO:68, SEQ ID NO:69, and SEQ ID NO:70. In any of the antibodies described above or elsewhere herein, the antibody can comprise: a) a VL region comprising one or more complementarity determining regions (CDRs) selected from SEQ ID NO:25, SEQ ID NO:26, and SEQ ID NO:27; and/or b) a VH region comprising one or more complementarity determining regions (CDRs) selected from SEQ ID NO:28, SEQ ID NO:29, and SEQ ID NO:30. In any of the antibodies described above or elsewhere herein, the antibody can comprise: a) a VL region comprising one or more complementarity determining regions (CDRs) selected from SEQ ID NO:33, SEQ ID NO:34, and SEQ ID NO:35; and/or b) a VH region comprising one or more complementarity determining regions (CDRs) selected from SEQ ID NO:36, SEQ ID NO:37, and SEQ ID NO:38. In any of the antibodies described above or elsewhere herein, the antibody can comprise: a) a VL region comprising one or more complementarity determining regions (CDRs) selected from SEQ ID NO:41, SEQ ID NO:42, and SEQ ID NO:43; and/or b) a VH region comprising one or more complementarity determining regions (CDRs) selected from SEQ ID NO:44, SEQ ID NO:45, and SEQ ID NO:46. In any of the antibodies described above or elsewhere herein, the antibody can comprise: a) a VL region comprising one or more complementarity determining regions (CDRs) selected from SEQ ID NO:49, SEQ ID NO:50, and SEQ ID NO:51; and/or b) a VH region comprising one or more complementarity determining regions (CDRs) selected from SEQ ID NO:52, SEQ ID NO:53, and SEQ ID NO:54. In any of the antibodies described above or elsewhere herein, the antibody can comprise: a) a VL region comprising one or more complementarity determining regions (CDRs) selected from SEQ ID NO:57, SEQ ID NO:58, and SEQ ID NO:59; and/or b) a VH region comprising one or more complementarity determining regions (CDRs) selected from SEQ ID NO:60, SEQ ID NO:61, and SEQ ID NO:62.

In any of the embodiments of a subject anti-Tau antibody, the light chain region and the heavy chain region can be present in separate polypeptides. In any of the embodiments of a subject anti-Tau antibody, the light chain region and the heavy chain region can be present in a single polypeptide. In any of the embodiments of a subject anti-Tau antibody, the antibody can comprise a heavy chain constant region, and wherein the heavy chain region is of the isotype IgG1, IgG2, IgG3, or IgG4. In any of the embodiments of a subject anti-Tau antibody, the antibody can be a Fv, scFv, Fab, F(ab')2, or Fab'. In any of the embodiments of a subject anti-Tau antibody, the antibody can comprise a covalently linked non-peptide synthetic polymer; for example, the synthetic polymer is a poly(ethylene glycol) polymer. In any of the embodiments of a subject anti-Tau antibody, the antibody can bind to an eTau polypeptide with a dissociation constant ($K_D$) of at least $10^{-7}$ M, $10^{-8}$ M, $10^{-9}$ M, $10^{-10}$ M, or $10^{-11}$ M. In any of the embodiments of a subject anti-Tau antibody, the antibody can be immobilized on an insoluble support. In any of the embodiments of a subject anti-Tau antibody, the antibody can comprise a detectable label; for example, the detectable label can be a chemiluminescent agent, a particulate label, a colorimetric agent, an energy transfer agent, an enzyme, a fluorescent agent, a contrast agent, or a radioisotope. In any of the embodiments of a subject anti-Tau antibody, in some cases, the epitope is not within amino acids 15-24, or within amino acids 5-20, or within amino acids 2-18, or within amino acids 19-46 of the Tau polypeptide.

The present disclosure provides a pharmaceutical formulation comprising: a) an antibody according to any one of the embodiments described above, or elsewhere herein; and b) a pharmaceutically acceptable excipient.

The present disclosure provides a recombinant expression vector comprising a nucleotide sequence encoding the antibody according to any one of the embodiments described above, or elsewhere herein, wherein the nucleotide sequence is operably linked to a transcriptional control element that is active in a eukaryotic cell. The present disclosure provides an in vitro host cell genetically modified with the recombinant expression vector.

The present disclosure provides a method of treating a tauopathy, characterized by an abnormal level of tau in a tissue or a fluid in an individual, the method comprising administering to the individual an antibody according to any one of the embodiments described above, or elsewhere herein, or the pharmaceutical composition according to any one of the embodiments described above, or elsewhere herein, wherein said administering treats the tauopathy. In some cases, the administering results in a change in one or more of: a) the amount of free extracellular tau in brain tissue; b) the amount of free extracellular tau in interstitial fluid (ISF); c) the amount of free extracellular tau in cerebrospinal fluid (CSF); d) the neuron-to-neuron spread of tau; e) the amount of intraneuron tau aggregates; f) the degree of microglial and/or astrocyte activation; g) the amount of phosphorylated or hyperphosphorylated tau; h) the amount of total Tau or free tau in ISF or CSF; i) the amount of intracellular N-terminal tau fragments; j) neuronal hyperactivity; k) the amount of Aβ40 and/or Aβ42 in CSF; l) the Aβ plaque burden; m) secretion of Aβ40 and/or Aβ42 from a neuron; n) amyloid precursor protein (APP) promoter activity; o) APP mRNA and/or protein level; p) the activity of beta-secretase and/or gamma secretase; q) the activation state of an Aβ induced signaling pathway; r) the amount of intracellular total tau or free tau; s) the amount of anti-tau antibody-bound tau in ISF or CSF; and t) the amount of intracellular anti-Tau antibody-bound tau. In some embodiments, the administering results in one or more of: a) an improvement in cognitive function in the individual; b) a reduction in the rate of decline in cognitive function in the individual; c) an improvement in motor function in the individual; and d) a reduction in the rate of decline in motor function in the individual. In some cases, the method further comprises administering at least one additional agent that treats the tauopathy. In some cases, administering an anti-Tau antibody is via an intravenous, intrathecal, intramuscular, or subcutaneous route of administration. In some cases, the anti-Tau antibody is formulated with an agent that facilitates crossing the blood-brain barrier. In some cases, the tauopathy is Alzheimer's disease.

The present disclosure provides a method of detecting an extracellular Tau (eTau) polypeptide in a biological sample obtained from an individual, the method comprising: a) contacting the sample with an antibody specific for the tau peptide; and b) detecting binding of the antibody to tau peptide present in the sample. In some cases, the eTau polypeptide comprises: a) an amino acid sequence having at least about 95% amino acid sequence identity to the amino acid sequence set forth in any one of SEQ ID NOs:1-3, wherein the tau peptide has a length of from about 5 amino acids to about 175 amino acids; b) an amino acid sequence having at least about 95% amino acid sequence identity to the amino acid sequence set forth in SEQ ID NO:4, wherein the tau peptide has a length of from about 5 amino acids to about 150 amino acids; c) an amino acid sequence having at least about 95% amino acid sequence identity to the amino acid sequence set forth in SEQ ID NO:5, wherein the tau peptide has a length of from about 5 amino acids to about 121 amino acids; or d) an amino acid sequence having at least about 95% amino acid sequence identity to the amino acid sequence set forth in SEQ ID NO:5, wherein the tau peptide has a length of from about 5 amino acids to about 67 amino acids. In some cases, the individual is suspected of having a tauopathy, has been diagnosed as having a tauopathy, or has a genetic predisposition to developing a tauopathy. In some cases, the tauopathy is Alzheimer's disease. In some cases, the biological sample is blood, serum, plasma, urine, saliva, or cerebrospinal fluid.

The present disclosure provides a method of detecting an extracellular Tau (eTau) polypeptide in a living individual in vivo, the method comprising administering to the individual an antibody according to any one of the embodiments described above or elsewhere herein; and detecting binding of the antibody to tau peptide in a brain tissue in the individual using an imaging method.

The present disclosure provides a kit comprising the isolated antibody according to any one of the embodiments described above or elsewhere herein. In some cases, the kit further comprises a reagent for use as a positive control; for example, the positive control can be a purified eTau polypeptide. In some cases, the antibody comprises a detectable label. In some cases, the antibody is immobilized on a solid support; for example, the solid support can be a test strip.

The present disclosure provides an assay device for use in detecting, in a liquid biological sample obtained from an individual, a extracellular Tau (eTau) polypeptide, the device comprising a matrix defining an axial flow path, the matrix comprising a sample receiving zone at an upstream end of the flow path that receives the liquid sample. In some cases, the eTau polypeptide comprises: a) an amino acid sequence having at least about 95% amino acid sequence identity to the amino acid sequence set forth in any one of SEQ ID NOs:1-3, wherein the tau peptide has a length of from about 5 amino acids to about 175 amino acids; b) an amino acid sequence having at least about 95% amino acid sequence identity to the amino acid sequence set forth in SEQ ID NO:4, wherein the tau peptide has a length of from about 5 amino acids to about 150 amino acids; c) an amino acid sequence having at least about 95% amino acid sequence identity to the amino acid sequence set forth in SEQ ID NO:5, wherein the tau peptide has a length of from about 5 amino acids to about 121 amino acids; or d) an amino acid sequence having at least about 95% amino acid sequence identity to the amino acid sequence set forth in SEQ ID NO:5, wherein the tau peptide has a length of from about 5 amino acids to about 67 amino acids. In some cases, the assay device further comprises: one or more test zones positioned within the flow path and downstream from the sample receiving zone, each of said one or more test zones comprising an antibody specific for tau peptide that is diagnostic of a tauopathy, wherein the antibody is immobilized in each of said test zones, wherein each of said immobilized antibodies is capable of binding different tau peptide present in said liquid sample, to form an immobilized antibody/tau peptide complex. In some cases, the assay device further comprises one or more control zones positioned within the flow path and downstream from the sample receiving zone. In some cases, the assay device is a test strip. In some cases, the device is a dipstick assay device. In some cases, the liquid sample is blood, serum, plasma, urine, saliva, or cerebrospinal fluid.

BRIEF DESCRIPTION OF THE DRAWINGS

FIGS. 1A and 1B depict amino acid sequences of eTau fragments, in alignment with a fetal tau amino acid sequence.

FIG. 2 depicts an amino acid sequence of full-length Tau.

FIGS. 5A-C depict: detection of Tau fragments in conditioned medium from induced pluripotent stem cell-derived cortical neurons (iPSC-CN) and human cortical cells (HCC), in interstitial fluid (ISF) from P301L tau mice, and in cerebrospinal fluid (CSF) from Progressive supranuclear palsy (PSP) and Alzheimer's disease (AD) patients (FIG. 5A); time course of eTau secretion (FIG. 5B); and the effect of Brefeldin A on eTau secretion (FIG. 5C).

FIGS. 8A-C depict induction of cortical neuron hyperactivity by an extracellular tau (eTau) fragment.

FIGS. 9A-E depict uptake of eTau by cortical neurons.

FIG. 14A depicts the amino acid sequence of eTau 2-166 (SEQ ID NO:3), compared to Tau 0N3R (SEQ ID NO:73). The C-terminal amino acids for eTau 2-172 and eTau 2-176 are depicted by arrows. FIG. 14B depicts a mass chromatogram of eTau present in conditioned medium of cortical neurons differentiated from iPSCs derived from a patient with AD ("endogenous eTau Prep19"). FIG. 14C provides a table showing the expected and observed molecular weights of eTau species present in endogenous eTau Prep19.

FIG. 16 depicts an enzyme-linked immunosorbent assay (ELISA) with anti-eTau antibodies to quantitate eTau fragments.

FIG. 17 provides Table 6, which provides amino acid sequences of VH and VL regions, and amino acid sequences of complementarity-determining regions (CDRs) of anti-Tau monoclonal antibodies (mAbs) 7295-M6 and 7295-M8.

FIG. 18 provides Table 7, which provides amino acid sequences of VH and VL regions, and amino acid sequences of CDRs of anti-Tau mAbs 7298-M1 and 7298-M2.

FIG. 19 provides Table 8, which provides amino acid sequences of VH and VL regions, and amino acid sequences of CDRs of anti-Tau mAbs 7299-M2, 7299-M5, and 7299-M9.

FIG. 20 provides Table 8, which provides amino acid sequences of VH and VL regions, and amino acid sequences of CDRs of anti-Tau mAb 7297-2M1.

DEFINITIONS

Figure 3:
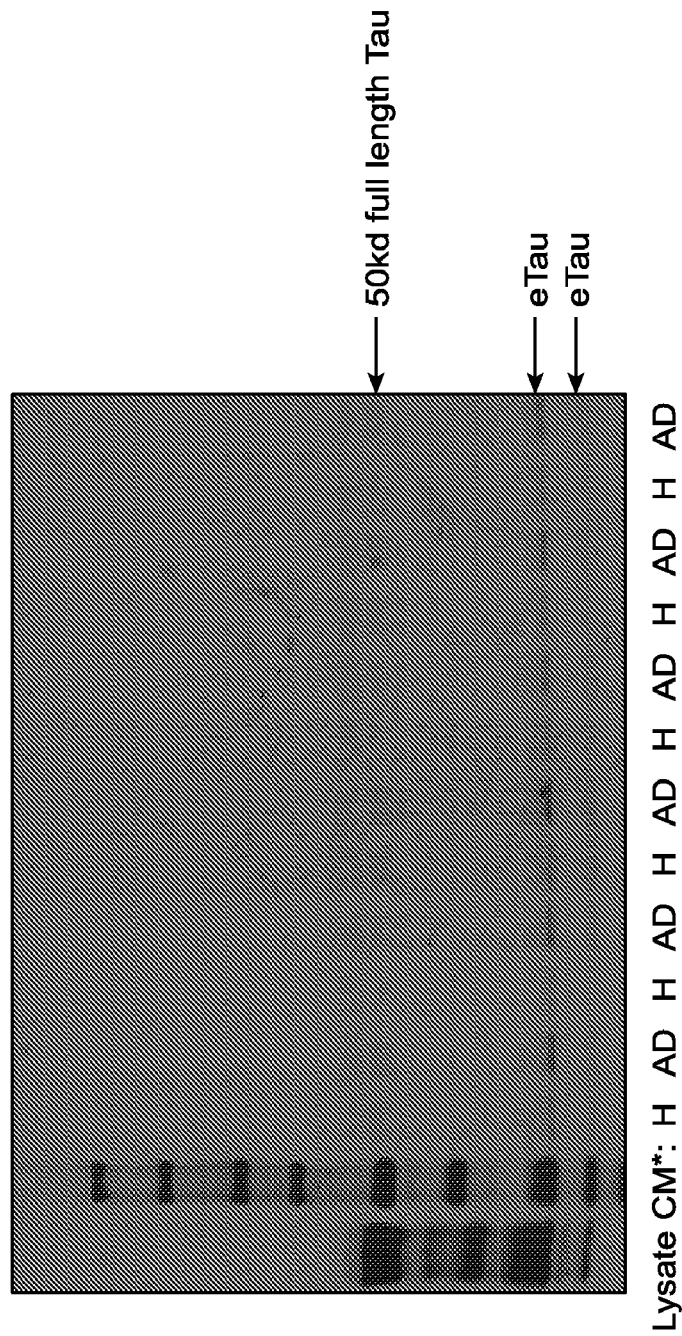
FIG. 3 is a Western blot showing the levels of extracellular Tau (eTau) in conditioned medium from various cell lines.

The terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

"Isolated" refers to a peptide of interest that, if naturally occurring, is in an environment different from that in which it may naturally occur. "Isolated" is meant to include peptides that are within samples that are substantially enriched for the peptide of interest and/or in which the peptide of interest is partially or substantially purified. Where the peptide is not naturally occurring, "isolated" indicates the peptide has been separated from an environment in which it was made by either synthetic or recombinant means. In some cases, an isolated peptide is purified ("substantially pure").

"Substantially pure" indicates that an entity (e.g., a tau peptide) makes up greater than about 50% of the total content of the composition (e.g., total protein of the composition), or greater than about 80% of the total protein content. For example, a "substantially pure" peptide refers to compositions in which at least 80%, at least 85%, at least 90% or more of the total composition is the peptide (e.g. 95%, 98%, 99%, greater than 99% of the total protein). The peptide can make up greater than about 90%, or greater than about 95% of the total protein in the composition.

The terms "nucleic acid" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

An "anti-tau antibody" refers to an antibody that binds a tau peptide, specifically binds a tau polypeptide with a $K_D$ less than about $10^{-7}$, less than about $10^{-8}$, less than about $10^{-9}$, less than about $10^{-10}$, less than about $10^{-11}$, or less than about $10^{-12}$ or less.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, bi-specific antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

The terms "humanized immunoglobulin" and "humanized antibody," as used herein, refers to an immunoglobulin comprising portions of immunoglobulins of different origin, wherein at least one portion comprises amino acid sequences of human origin. For example, the humanized antibody can comprise portions derived from an immunoglobulin of non-human origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120, 694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946, 778; Huston, U.S. Pat. No. 5,476,786; and Bird, R. E. et al., Science, 242: 423-426 (1988)), regarding single chain antibodies.

For example, humanized antibodies can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444-6448.

As used herein, the term "affinity" refers to the equilibrium constant for the reversible binding of two agents (e.g., an antibody and an antigen) and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A subject anti-Tau antibody binds specifically to an epitope within a Tau polypeptide. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

By "treatment" is meant that at least an amelioration of the symptoms associated with the condition afflicting the host is achieved, where amelioration refers to at least a reduction in the magnitude of a parameter, e.g. symptom, associated with the condition being treated. As such, treatment includes situations where the condition, or at least symptoms associated therewith, are reduced or avoided. Thus treatment includes: (i) prevention, that is, reducing the risk of development of clinical symptoms, including causing the clinical symptoms not to develop, e.g., preventing disease progression to a harmful or otherwise undesired state; (ii) inhibition, that is, arresting the development or further development of clinical symptoms, e.g., mitigating or completely inhibiting an active disease.

The term "effective amount" or "therapeutically effective amount" means a dosage sufficient to provide for treatment for the disease state being treated or to otherwise provide the desired effect (e.g., induction of an effective immune response, reduction of one or more pathological features of a tauopathy, etc.). The precise dosage can vary according to a variety of factors, such as subject-dependent variables (e.g., weight, age, etc.), the disease, and the treatment being effected.

The terms "individual," "host," "subject," and "patient," used interchangeably herein, refer to a mammal, including, but not limited to, murines (e.g., rats, mice), lagomorphs, non-human primates, humans, etc. In some embodiments, an individual is a human. In some embodiments, an individual is a rodent (e.g., a mouse, a rat, etc.) or a lagomorph (e.g., a rabbit).

The term "biological sample," as used herein, refers to a composition containing matter obtained directly from a subject (e.g., a human patient, or human control subject). The term "biological sample" encompasses liquid samples of biological origin, solid tissue samples such as a biopsy specimen or tissue cultures or cells derived therefrom and the progeny thereof. Examples of biological samples include, but are not limited to samples of: cerebrospinal fluid (CSF), interstitial fluid (ISF), whole blood, serum, plasma, sputum, urine, pleural fluid, lacrimal fluid, bronchioalveolar lavage fluid, saliva, feces, hair, and tissues. The definition also includes samples that have been manipulated in any way after their procurement, such as by treatment with reagents, solubilization, or enrichment for certain components. The term "biological sample" encompasses a clinical sample, and also includes cells in culture, cell supernatants, cell lysates, serum, plasma, biological fluid, and tissue samples. In some cases, a biological sample is a liquid sample.

The term "induced pluripotent stem cell," (iPSC) as used herein, refers to a pluripotent stem cell derived from a postnatal somatic cell by any combination of forced expression of reprogramming factors alone or in combination with one or more reprogramming agents.

The term "cellular reprogramming," as used herein, refers to any of a number of known methods for converting cells of one cell type (e.g., fibroblasts) into cells of another cell type (e.g., neurons). Such methods include "direct conversion" methods in which a starting cell type is converted into a desired cell type without an intermediate cell type step. Cellular reprogramming also includes conversion of starting cell types (e.g., fibroblasts or white blood cells) into pluripotent stem cells (referred to as "induced pluripotent stem cells"; iPSCs) followed by directed differentiation in vitro to become cell types of interest, e.g., cortical neurons, motor neurons, or astrocytes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a tau peptide" includes a plurality of such peptides and reference to "the composition" includes reference to one or more compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides isolated tau peptides, and compositions comprising the peptides. The present disclosure provides antibodies specific for an isolated tau peptide, as well as kits and assay devices comprising the antibodies. The antibodies find use in diagnostic and treatment methods, which are also provided.

Tau Peptides

The present disclosure provides isolated tau peptides, and compositions comprising the peptides. In some cases, a subject Tau peptide is an extracellular Tau ("eTau") polypeptide. "Extracellular tau" ("eTau"), as used herein, encompasses any Tau polypeptide that can be detected in cerebrospinal fluid (CSF) or interstitial fluid (ISF).

(eTau1)

A tau peptide (e.g., an eTau polypeptide; e.g., an eTau1 polypeptide) of the present disclosure can comprise an amino acid sequence having at least about 80%, at least about 85%, at least about 90%, at least about 95%, at least about 98%, at least about 99%, or 100%, amino acid sequence identity to a contiguous stretch of from about 5 amino acids to 175 amino acids (e.g., a contiguous stretch of from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 125 aa, from about 125 aa to about 150 aa, or from about 150 aa to about 175 aa) of the Tau peptide amino acid sequence depicted in FIG. 1A and set forth in SEQ ID NO:1. In some cases, the N-terminal alanine is acetylated.

In some cases, e.g., where a subject tau peptide has a length of 175 amino acids, the C-terminal amino acid of the tau peptide is lysine, which may be referred to as "K176," the "176" referring to the numbering based on human fetal tau (SEQ ID NO:7 as depicted in FIGS. 1A and 1B).

A subject tau peptide can have a length of from about 5 amino acids to about 175 amino acids, e.g., from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 125 aa, from about 125 aa to about 150 aa, or from about 150 aa to about 175 aa.

A tau peptide of the present disclosure can comprise an amino acid sequence having at least about 80%, at least about 85%, at least about 90%, at least about 95%, at least about 98%, at least about 99%, or 100%, amino acid sequence identity to a contiguous stretch of from about 5 amino acids to 171 amino acids (e.g., a contiguous stretch of from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 125 aa, from about 125 aa to about 150 aa, or from about 150 aa to about 171 aa) of the Tau peptide amino acid sequence depicted in FIG. 1A and set forth in SEQ ID NO:2. In some cases, the N-terminal alanine is acetylated.

In some cases, e.g., where a subject tau peptide has a length of 171 amino acids, the C-terminal amino acid of the tau peptide is arginine, which may be referred to as "R172," the "172" referring to the numbering based on human fetal tau (SEQ ID NO:7 as depicted in FIGS. 1A and 1B).

A subject tau peptide can have a length of from about 5 amino acids to about 171 amino acids, e.g., from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 125 aa, from about 125 aa to about 150 aa, or from about 150 aa to about 171 aa.

(eTau2)

A tau peptide (e.g., an eTau polypeptide; e.g., an eTau2 polypeptide) of the present disclosure can comprise an amino acid sequence having at least about 80%, at least about 85%, at least about 90%, at least about 95%, at least about 98%, at least about 99%, or 100%, amino acid sequence identity to a contiguous stretch of from about 5 amino acids to 150 amino acids (e.g., a contiguous stretch of from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 125 aa, or from about 125 aa to about 150 aa) of the Tau peptide amino acid sequence depicted in FIG. 1A and set forth in SEQ ID NO:4.

In some cases, e.g., where a subject tau peptide has a length of 150 amino acids, the C-terminal amino acid of the tau peptide is arginine, which may be referred to as "R151," the "151" referring to the numbering based on human fetal tau (SEQ ID NO:7 as depicted in FIGS. 1A and 1B).

A subject tau peptide can have a length of from about 5 amino acids to about 150 amino acids, e.g., from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 125 aa, or from about 125 aa to about 150 aa.

(eTau3)

A tau peptide (e.g., an eTau polypeptide; e.g., an eTau3 polypeptide) of the present disclosure can comprise an amino acid sequence having at least about 80%, at least about 85%, at least about 90%, at least about 95%, at least about 98%, at least about 99%, or 100%, amino acid sequence identity to a contiguous stretch of from about 10 amino acids to 121 amino acids (e.g., a contiguous stretch of from about 10 amino acids (aa) to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, or from about 100 aa to about 121 aa) of the Tau peptide amino acid sequence depicted in FIG. 1A and set forth in SEQ ID NO:5.

In some cases, e.g., where a subject tau peptide has a length of 121 amino acids, the C-terminal amino acid of the tau peptide is lysine, which may be referred to as "K122," the "122" referring to the numbering based on human fetal tau (SEQ ID NO:7 as depicted in FIGS. 1A and 1B).

A subject tau peptide can have a length of from about 5 amino acids to about 121 amino acids, e.g., from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, or from about 100 aa to about 121 aa. (eTau4)

A tau peptide (e.g., an eTau polypeptide; e.g., an eTau4 polypeptide) of the present disclosure can comprise an amino acid sequence having at least about 80%, at least about 85%, at least about 90%, at least about 95%, at least about 98%, at least about 99%, or 100%, amino acid sequence identity to a contiguous stretch of from about 10 amino acids to 67 amino acids (e.g., a contiguous stretch of from about 10 amino acids (aa) to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, or from about 50 aa to about 67 aa) of the Tau peptide amino acid sequence depicted in FIG. 1A and set forth in SEQ ID NO:6.

In some cases, e.g., where a subject tau peptide has a length of 67 amino acids, the C-terminal amino acid of the tau peptide is arginine, which may be referred to as "R68," the "68" referring to the numbering based on human fetal tau (SEQ ID NO:7 as depicted in FIGS. 1A and 1B).

A subject tau peptide can have a length of from about 5 amino acids to about 67 amino acids, e.g., from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, or from about 50 aa to about 67 aa.

In some cases, a tau peptide (e.g., and extracellular Tau peptide) of the present disclosure comprises one or more acetylated amino acids. In some instances, only the N-terminal amino acid residue of a subject acetylated tau peptide is acetylated. In some instances, only the N-terminal amino acid residue of a subject acetylated tau peptide is acetylated; and the tau peptide does not include any other amino acid modifications (e.g., the peptide is not phosphorylated). In other cases, the N-terminal amino acid residue of a subject acetylated tau peptide is acetylated; and the tau peptide comprises one or more additional acetylated amino acid residues. In still other cases, only the N-terminal amino acid residue of a subject acetylated tau peptide is acetylated; and one or more amino acid residues (other than the N-terminal amino acid residue) is phosphorylated.

For example, in some cases, the N-terminal amino acid residue of a subject acetylated tau peptide is acetylated; and Thr-122 (corresponding to Thr-123 of fetal tau) is phosphorylated. In some instances, the N-terminal amino acid residue of a subject acetylated tau peptide is acetylated; and Ser-143 (corresponding to Ser-144 of fetal tau) is phosphorylated. In still other cases, the N-terminal amino acid residue of a subject acetylated tau peptide is acetylated; Thr-122 (corresponding to Thr-123 of fetal tau) is phosphorylated; and Ser-143 (corresponding to Ser-144 of fetal tau) is phosphorylated.

A tau peptide of the present disclosure can be hypophosphorylated relative to intracellular tau; e.g., the tau peptide can have fewer phosphorylated amino acids than an intracellular tau peptide having the same amino acid sequence. For example, where an intracellular tau peptide may have 3 or more phosphorylated amino acid residues, a subject tau peptide can have fewer than 3 phosphorylated amino acid residues, e.g., 2 phosphorylated amino acid residues, 1 phosphorylated amino acid residue, or no phosphorylated amino acid residues.

In some instances, in a population of tau peptides of the present disclosure that are homogeneous with respect to the sequence of amino acid residues (e.g., residues without post-translational modification), from about 2% to about 100% of the population can include an amino acid residue having a phosphorylated side chain. For example, from about 2% to about 5%, from about 5% to about 10%, from about 10% to about 15%, from about 15% to about 20%, from about 20% to about 25%, from about 25% to about 30%, from about 30% to about 40%, from about 40% to about 50%, from about 50% to about 60%, from about 60% to about 70%, from about 70% to about 80%, from about 80% to about 90%, or from about 90% to about 100%, of the tau peptides in a population of tau peptides of the present disclosure that are homogeneous with respect to amino acid sequence can include one, two, three, or more than three, phosphorylated amino acid residues (e.g., phosphorylated serine; phosphorylated threonine).

As one non-limiting example, in some cases, a subject tau peptide comprises an acetylated N-terminal amino acid (e.g., $Ala^{Ac}$) and may or may not include one or more additional amino acid modifications, e.g., a modification of an amino acid other than the N-terminal Ala.

A subject tau peptide can comprise 1, 2, 3, 4, 5, 6, 7, 8, 9, 10, or more than 10, amino acid substitutions (e.g., conservative amino acid substitutions), relative to the amino acid sequence set forth in any one of SEQ ID NOs:1-6, as depicted in FIG. 1A.

By "conservative amino acid substitution" generally refers to substitution of amino acid residues within the following groups:
1) L, I, M, V, F;
2) R, K;
3) F, Y, H, W, R;
4) G, A, T, S;
5) Q, N; and
6) D, E.

Conservative amino acid substitutions in the context of a subject tau peptide are selected so as to preserve a biological activity of the peptide. Such presentation may be preserved by substituting with an amino acid with a side chain of similar acidity, basicity, charge, polarity, or size to the side chain of the amino acid being replaced. Guidance for substitutions, insertion, or deletion may be based on alignments of amino acid sequences of different variant proteins or proteins from different species. For example, at certain residue positions that are fully conserved, substitution, deletion or insertion may not be allowed while at other positions where one or more residues are not conserved, an amino acid change can be tolerated. Residues that are semi-conserved may tolerate changes that preserve charge, polarity, and/or size.

Detectable Labels

A tau peptide of the present disclosure can include a detectable label. Suitable detectable labels include any moiety detectable by spectroscopic, photochemical, biochemical, immunochemical, electrical, optical or chemical means. Suitable detectable labels include, but are not limited to, magnetic beads (e.g. Dynabeads™); fluorescent proteins (e.g., a green fluorescent protein, a red fluorescent protein, a yellow fluorescent protein, and the like); fluorescent dyes (e.g., fluorescein isothiocyanate, texas red, rhodamine or a rhodamine derivative (e.g., rhodamine B; TAMRA), 7-Amino-4-methyl-coumarin (AMC), 5-((2-Aminoethyl)

amino)napthalene-1-sulfonic acid (EDANS), 7-Nitrobenz-2-oxa-1,3-diazole (NBD), etc.); a fluorescence quencher (e.g., Dabcyl, Dansyl, 2,4-Dinitrophenol, etc.); p-Nitroaniline; radiolabels (e.g., $^3$H, $^{125}$I, $^{35}$S, $^{14}$C, $^{14}$N, $^{13}$C, $^{15}$N, or $^{32}$P); enzymes (e.g., horse radish peroxidase, alkaline phosphatase, luciferase, and others commonly used in an enzyme-linked immunosorbent assay (ELISA)); colorimetric labels such as colloidal gold or colored glass or plastic (e.g. polystyrene, polypropylene, latex, etc.) beads; and the like.

Solid Supports

A tau peptide of the present disclosure can be attached, directly or via a linker, to a solid support. Suitable supports are well known in the art and include, inter alia, commercially available column materials, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject tau peptide onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

Modifications

In some cases, a tau peptide of the present disclosure comprises one or more modifications. For example, a subject tau peptide can be cyclized. As another example, a subject tau peptide can have one or more amino acid modifications. A subject tau peptide can include one or more D-amino acids.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are peptides that have phosphorylated amino acid residues, e.g. phosphotyrosine, phosphoserine, or phosphothreonine. In some instances, a subject peptide comprises one or more phosphorylated amino acids. In some instances, a tau peptide of the present disclosure comprises a phosphothreonine residue and/or a phosphoserine residue.

The present disclosure also provides tau peptides that have been modified using ordinary molecular biological techniques and synthetic chemistry so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids.

The following are non-limiting examples of amino acid modifications that can be made to a subject tau peptide:

a) substitution of alkyl-substituted hydrophobic amino acids: including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids: including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains: including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residues: including asparagine, glutamine, and alkyl or aromatic substituted derivatives of asparagine or glutamine; and f) substitution of hydroxyl containing amino acids: including serine, threonine, homoserine, 2,3-diaminopropionic acid, and alkyl or aromatic substituted derivatives of serine or threonine.

In some cases, a subject tau peptide comprises one or more naturally occurring non-genetically encoded L-amino acids, synthetic L-amino acids or D-enantiomers of an amino acid. For example, a tau peptide of the present disclosure can comprise only D-amino acids. For example, a tau peptide of the present disclosure can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, s-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

In some cases, a subject tau peptide includes one or more linkages other than peptide bonds, e.g., at least two adjacent amino acids are joined via a linkage other than an amide bond. For example, to reduce or eliminate undesired proteolysis or other degradation pathways and/or to increase serum stability and/or to restrict or increase conformational flexibility, one or more amide bonds within the backbone of a tau peptide of the present disclosure can be substituted.

For example, one or more amide linkages (—CO—NH—) in a subject tau peptide can be replaced with another linkage which is an isostere such as: —$CH_2NH$—, —$CH_2S$—, —$CH_2CH_2$—, —CH=CH-(cis and trans), —$COCH_2$—, —$CH(OH)CH_2$— and —$CH_2SO$—. This replacement can be made by methods known in the art.

As another example, one or more amide linkages in a tau peptide of the present disclosure can be replaced with a reduced isostere pseudopeptide bond. Couder et al. (1993) *Int. J. Peptide Protein Res.* 41:181-184.

A tau peptide may be joined to a wide variety of other peptides or proteins for a variety of purposes. By providing for expression of a subject peptide, various post-translational modifications may be achieved. For example, by employing the appropriate coding sequences, one may provide farnesylation or prenylation. In this situation, the peptide will be bound to a lipid group at a terminus, so as to be able to be bound to a lipid membrane, such as a liposome.

A cysteine residue or a cysteine analog can be introduced into a subject tau peptide to provide for linkage to another peptide via a disulfide linkage or to provide for cyclization of a subject tau peptide. Methods of introducing a cysteine or cysteine analog are known in the art; see, e.g., U.S. Pat. No. 8,067,532.

A tau peptide of the present disclosure can be cyclized. One or more cysteine or cysteine analogs can be introduced into a subject tau peptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moiety) that can form a cyclizing bond can be used and/or introduced. A cyclizing bond can be generated with any combination of amino acids (or with amino acid and —$(CH_2)_n$—CO— or —$(CH_2)_n$—$C_6H_4$—CO—) with functional groups which allow for the introduction of a bridge. Some examples are disulfides, disulfide mimetics such as the —$(CH_2)_n$— carba bridge, thioacetal, thioether bridges (cystathionine or lanthionine) and bridges containing esters and ethers.

Other modifications include, for example, an N-alkyl (or aryl) substitution (ψ[CONR]), or backbone crosslinking to construct lactams and other cyclic structures. Other derivatives of the modulator compounds of the invention include C-terminal hydroxymethyl derivatives, 0-modified derivatives (e.g., C-terminal hydroxymethyl benzyl ether), N-terminally modified derivatives including substituted amides such as alkylamides and hydrazides.

In some cases, one or more L-amino acids in a tau peptide of the present disclosure is replaced with a D-amino acid.

In some cases, a subject tau peptide is a retroinverso analog. Sela and Zisman (1997) *FASEB J.* 11:449. Retroinverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids. See, e.g., Jameson et al. (1994) *Nature* 368:744; and Brady et al. (1994) *Nature* 368:692.

The carboxyl group $COR_3$ of the amino acid at the C-terminus of a subject tau peptide can be present in a free form ($R_3$=OH) or in the form of a physiologically tolerated alkaline or alkaline earth salt such as e.g. a sodium, potassium or calcium salt. The carboxyl group can also be esterified with primary, secondary or tertiary alcohols such as e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched $C_1$-$C_6$-alkylamines or $C_1$-$C_6$ di-alkylamines, e.g., methylamine or dimethylamine.

The amino group of the amino acid $NR_1R_2$ at the N-terminus of a tau peptide of the present disclosure can be present in a free form ($R_1$=H and $R_2$=H) or in the form of a physiologically tolerated salt such as e.g., a chloride or acetate. The amino group can also be acetylated with acids so that $R_1$=H and $R_2$=acetyl, trifluoroacetyl, or adamantyl. The amino group can be present in a form protected by conventional amino protecting groups of peptide chemistry such as e.g., Fmoc, Z, Boc, or Alloc. The amino group can be N-alkylated in which $R_1$ and/or $R_2$=$C_1$-$C_6$ alkyl or $C_2$-$C_8$ alkenyl or $C_7$-$C_9$ aralkyl.

Alkyl residues can be straight-chained, branched or optionally cyclic alkyl residues, e.g., methyl, ethyl, isopropyl and cyclohexyl.

One way to modify a subject tau peptide is to conjugate (e g link) one or more additional elements at the N- and/or C-terminus of the peptide, such as another protein (e.g. having an amino acid sequence heterologous to the subject peptide) and/or a carrier molecule. Thus, an exemplary protein is a fusion protein comprising a peptide(s) derived from a tau peptide of the present disclosure.

Modifications that can enhance serum half-life of a subject tau peptide are of interest. A subject tau peptide may be "PEGylated", as containing one or more poly(ethylene glycol) (PEG) moieties. Methods and reagents suitable for PEGylation of a protein are well known in the art and may be found in U.S. Pat. No. 5,849,860, disclosure of which is incorporated herein by reference. PEG suitable for conjugation to a protein is generally soluble in water at room temperature, and has the general formula R(O—$CH_2$—$CH_2)_n$ O—R, where R is hydrogen or a protective group such as an alkyl or an alkanol group, and where n is an integer from 1 to 1000. Where R is a protective group, it generally has from 1 to 8 carbons.

The PEG conjugated to a subject tau peptide can be linear. The PEG conjugated to the subject tau peptide may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

Where a tau peptide of the present disclosure is to be incorporated into a liposome, carbohydrate, lipid moiety, including N-fatty acyl groups such as N-lauroyl, N-oleoyl, fatty amines such as dodecyl amine, oleoyl amine, and the like (e.g., see U.S. Pat. No. 6,638,513) may also be used to modify the subject tau peptide.

Additional Modifications

A subject tau peptide can be modified to comprise one or more covalently linked moieties. Suitable modifications include, e.g., biotin; lipids (e.g., farnesyl, formyl, myristoyl, palmitoyl and stearyl groups); poly(ethylene glycol); ((His)$_n$, e.g., 6His; an epitope tag, e.g., glutathione-S-transferase (GST), hemagglutinin (HA; e.g., YPYDVPDYA; SEQ ID NO:74), FLAG (e.g., DYKDDDDK; SEQ ID NO:75), c-myc (e.g., EQKLISEEDL; SEQ ID NO:76)); a carrier (e.g., for immunization); and the like.

Carriers

A tau peptide of the present disclosure can be linked to a carrier. The term "linked," as used herein interchangeably with the term "coupled," refers to proximately associated, e.g., the tau peptide and the carrier are in close spatial proximity. In some cases, the linkage is a covalent linkage. In other cases, the linkage is a non-covalent linkage. The tau peptide can be linked directly to the carrier. Alternatively, the tau peptide can be linked to a carrier indirectly, e.g., via a linker molecule.

Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactivated virus particles; inactivated bacterial toxins such as toxoid from diphtheria, tetanus, cholera, leukotoxin molecules; liposomes; inactivated bacteria; dendritic cells; and the like. Carriers are described in further detail below.

Suitable carriers are well known in the art, and include, e.g., thyroglobulin, albumins such as human serum albumin, tetanus toxoid; Diphtheria toxoid; polyamino acids such as poly(D-lysine:D-glutamic acid); VP6 polypeptides of rotaviruses; influenza virus hemagglutinin, influenza virus nucleoprotein; hepatitis B virus core protein, hepatitis B virus surface antigen; purified protein derivative (PPD) of tuberculin from *Mycobacterium tuberculosis*; inactivated *Pseudomonas aeruginosa* exotoxin A (toxin A); Keyhole Limpet Hemocyanin (KLH); filamentous hemagglutinin (FHA) of *Bordetella pertussis*; T helper cell (Th) epitopes of tetanus toxoid (TT) and Bacillus Calmette-Guerin (BCG) cell wall; recombinant 10 kDa, 19 kDa and 30-32 kDa proteins from *M. leprae* or from *M. tuberculosis*, or any combination of these proteins; and the like. See, e.g., U.S. Pat. No. 6,447,778 for a discussion of carriers, and for methods of conjugating peptides to carriers.

*Pseudomonas aeruginosa* exotoxin A (toxin A) has been used effectively as a carrier in conjugate vaccines. *Pseudomonas aeruginosa* exotoxin A may be purified from the supernatant of fermentor-grown cultures of *Pseudomonas aeruginosa* PA 103. Toxin A has been classified as a superantigen based upon results in animals. Toxin A can be completely and irreversibly detoxified by covalent coupling to adipic acid dihydrazide (ADH), a 4 carbon spacer molecule. This step destroys the ADPR-transferase activity of the toxin molecule, hence rendering it nontoxic. The non-reacted hydrazide group can be used to covalently couple a polypeptide to toxin A. Toxin A may also be coupled to a polypeptide using a carbodiimide reagent.

Tau-peptide conjugates are conveniently prepared with glutaraldehyde as coupling agent. See, e.g., Rubinstein et al. (1995) *AIDS* 9:243-51.

The methods by which a subject polypeptide is conjugated with a carrier include disulfide linkages through a C terminal peptide cysteine linkage, coupling with glutaraldehyde solution for two hours, coupling with tyrosine, or coupling with water soluble carbodiimide.

In some embodiments, a subject tau peptide is lipidated. The lipid residue, such as palmitic acid or the like, is attached to the amino terminus of the peptide. The lipid can be attached directly to the peptide, or, indirectly via a linkage, such as a Ser-Ser, Gly, Gly-Gly, Ser linkage or the like. As another example, *E. coli* lipoprotein, such as tripalmitoyl-S-glycerylcysteinyl-seryl-serine ($P_3$ CSS), can be used to prime specific CTL when covalently attached to the peptide. See, Deres et al., *Nature* 342:561-564 (1989). A subject tau peptide can be conjugated with uncharged fatty acid residues of different chain lengths and degrees of unsaturation, ranging from acetic to stearic acid as well as to negatively charged succinyl residues via the appropriate carboxylic acid anhydrides. See, e.g., U.S. Pat. No. 6,419,931.

A subject tau peptide may be conjugated directly or indirectly, e.g., via a linker molecule, to a carrier. A wide variety of linker molecules are known in the art and can be used in the conjugates. The linkage from the peptide to the carrier may be through a peptide reactive side chain, or the N- or C-terminus of the peptide. A linker may be an organic, inorganic, or semi-organic molecule, and may be a polymer of an organic molecule, an inorganic molecule, or a copolymer comprising both inorganic and organic molecules.

If present, the linker molecules are generally of sufficient length to permit the tau peptide and a linked carrier to allow some flexible movement between the tau peptide and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Methods of Making a Tau Peptide

A subject tau peptide can be isolated and purified in accordance with conventional methods of recombinant synthesis. A lysate can be prepared of an expression host cell that produces a subject tau peptide, or the culture medium from an expression host cell that produces a subject tau peptide can be harvested, and a tau peptide can be purified from the lysate or culture medium using high performance liquid chromatography (HPLC), exclusion chromatography, gel electrophoresis, affinity chromatography, or other purification technique. In some cases, a composition comprising a subject tau peptide will comprise at least 80% by weight of the desired product, at least about 85% by weight, at least about 95% by weight, or at least about 99.5% by weight, in relation to contaminants related to the method of preparation of the tau peptide product and its purification. The percentages can be based upon total protein.

In some cases, a tau peptide of the present disclosure will be purified from the culture medium of a cell that produces the tau peptide. For example, a host cell can be genetically modified with a nucleic acid comprising a nucleotide sequence encoding a subject tau peptide, such that the genetically modified host cell produces the tau peptide and secretes it into the culture medium.

A subject tau peptide can also be prepared by in vitro chemical synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like. For example, solid-phase peptide synthesis (SPPS) allows the incorporation of unnatural amino acids and/or peptide/protein backbone modification. Various forms of SPPS, such as Fmoc and Boc, are available for synthesizing a subject peptide. Details of the chemical synthesis are known in the art (e.g., Ganesan A. 2006 *Mini Rev. Med Chem.* 6:3-10 and Camarero J A et al. 2005 *Protein Pept Lett.* 12:723-8).

If desired, various groups may be introduced into the peptide during synthesis or during expression. For example, a tau peptide can be acetylated and/or phosphorylated during synthesis. As noted above, SPPS allows the incorporation of unnatural amino acids and/or peptide/protein backbone modification. Methods for acetylating an amino acid, methods for phosphorylating an amino acid (e.g., incorporating a phosphorylated amino acid) are known in the art. See, e.g., "Amino Acid and Peptide Synthesis" (2002) John Jones, Oxford University Press, $2^{nd}$ Ed; "Fmoc Solid Phase Peptide Synthesis: A Practical Approach" (2000) W. C. Chan and Peter D. White, eds., Oxford University Press, $1^{st}$ Ed.

Alternatively, a group can be introduced into a tau peptide, which group can provide for linking to other molecules or to a surface. Thus, e.g., cysteines can be used to make thioethers, histidines for linking to a metal ion complex, carboxyl groups for forming amides or esters, amino groups for forming amides, and the like.

The peptide generated by chemical synthesis can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

As another example, a tau peptide can be purified from the culture medium of a neuronal cell (e.g., a cortical neuron; a motor neuron) that has been derived from an induced pluripotent stem (iPS) cell. For example, a fibroblast or other somatic cell obtained from an individual can be used to generate an iPS cell; and the iPS cell so generated can be induced in in vitro cell culture to differentiate into a cortical neuron or a motor neuron, using methods known in the art. See, e.g., Dimos et al. (2008) *Science* 321:1218-1221; Chambers et al. (2009) *Nat. Biotechnol.* 27:275; Cooper et al. (2010) *Mol. Cell. Neurosci.* 45:258; and Hu et al. (2010) *Proc. Natl. Acad. Sci. USA* 107:4335. A tau peptide secreted into the culture medium by the in vitro differentiated neuron can be purified from the culture medium.

In some cases, the neuron is produced by differentiating in vitro an iPS cell generated from a somatic cell (e.g., a fibroblast) obtained from an individual having a tauopathy. Methods of making iPS cells from a somatic cell, such as a fibroblast, are known in the art. See, e.g., Takahashi and Yamanaka (2006) Cell 126:663-676; Yamanaka et al. (2007) Nature 448:313-7; Wernig et al. (2007) Nature 448:318-24; Maherali (2007) Cell Stem Cell 1:55-70; Maherali and Hochedlinger (2008) Cell Stem Cell 3:595-605; Park et al. (2008) Cell 134:1-10; Dimos et al. (2008) Science 321:1218-1221; Blelloch et al. (2007) Cell Stem Cell 1:245-247; Stadtfeld et al. (2008) Science 322:945-949; Stadtfeld et al. (2008) 2:230-240; Okita et al. (2008) Science 322:949-953; Yu et al. (2009) *Science* 324:797; Soldner et al. (2009) Cell 136:964; and Kaji et al. (2009) Nature 458:771.

An iPS cell can be generated from a variety of cells, including, but not limited to: fibroblasts, skin fibroblasts, dermal fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, epithelial cells, gastric epithelial cells, lung epithelial cells, synovial cells, kidney cells, skin epithelial cells, pancreatic beta cells, and osteoblasts. Cells used to generate iPS cells can originate from a variety of types of tissue including but not limited to: bone marrow, skin (e.g., dermis, epidermis), muscle, adipose tissue, peripheral blood, foreskin, skeletal muscle, and smooth muscle.

Cells used to generate an iPS cell can be obtained from a human (e.g., an adult human) who has a tauopathy. For example, cells used to generate an iPS cell can be obtained from a human (e.g., an adult human) who has Alzheimer's disease.

iPS cells produce and express on their cell surface one or more of the following cell surface antigens: SSEA-3, SSEA-4, TRA-1-60, TRA-1-81, TRA-2-49/6E (alkaline phosphatase), and Nanog. For example, iPS cells can express on their cell surface SSEA-3, SSEA-4, TRA1-60, TRA1-81, and Nanog.

Generation of an iPS cell from a somatic cell can involve forcing expression of a set of factors in a somatic cell in order to promote increased potency of the cell or de-differentiation of the cell. Forcing expression can include introducing expression vectors encoding exogenous polypeptides into cells, where exogenous polypeptides include, e.g., one, two, three, four, or more of: Oct3/4, Klf4, c-Myc, Sox2, Nanog, Lin28, Esrrb, SV40 Large T antigen, and hTERT. For example, an iPS cell can be generated from an adult somatic cell by introducing into the somatic cell one or more expression vectors comprising nucleotide sequences encoding Oct3/4, Klf4, c-Myc, Sox2, Nanog, and Lin28. As another example, an iPS cell can be generated from an adult somatic cell by introducing into the somatic cell one or more expression vectors comprising nucleotide sequences encoding Oct3/4, Klf4, c-Myc, and Sox2.

An iPS cell can be generated from a somatic cell without the use of vectors or transgene sequences. See, e.g., Yu et al. (2009) *Science* 324:797; Soldner et al. (2009) *Cell* 136:964; and Kaji et al. (2009) *Nature* 458:771.

An iPS can be induced to differentiate into a neuron in vitro. Methods of inducing an iPS cell to differentiate into a neuron in vitro are known in the art. See, e.g., Dimos et al. (2008) Science 321:1218-1221; Chambers et al. (2009) *Nat. Biotechnol.* 27:275; Cooper et al. (2010) *Mol. Cell. Neurosci.* 45:258; and Hu et al. (2010) *Proc. Natl. Acad. Sci. USA* 107:4335. An iPS cell can be maintained in vitro in a culture medium, such that embryoid bodies (EBs) spontaneously form. EBs can be maintained in vitro in a culture medium comprising an agonist of the sonic hedgehog (SHH) signaling pathway and retinoic acid (RA), then plated on laminin-coated surface; under these conditions, EBs differentiate into neurons; see, e.g., Dimos (2008) supra.

Neurons may be identified by expression of one or more neuronal markers such as: Tuj1 (β-III-tubulin); MAP-2 (microtubule associated protein 2, other MAP genes such as MAP-1 or -5 may also be used); anti-axonal growth clones; ChAT (choline acetyltransferase); CgA (anti-chromagranin A); DARRP (dopamine and cAMP-regulated phosphoprotein); DAT (dopamine transporter); GAD (glutamic acid decarboxylase); GAP (growth associated protein); anti-HuC protein; anti-HuD protein; α-internexin; NeuN (neuron-specific nuclear protein); NF (neurofilament); NGF (nerve growth factor); γ-SE (neuron specific enolase); peripherin; PH8; PGP (protein gene product); SERT (serotonin transporter); synapsin; Tau (neurofibrillary tangle protein); anti- Thy-1; TRK (tyrosine kinase receptor); TRH (tryptophan hydroxylase); anti-TUC protein; TH (tyrosine hydroxylase); VRL (vanilloid receptor like protein); VGAT (vesicular GABA transporter); and VGLUT (vesicular glutamate transporter).

Nucleic Acids and Host Cells

The present disclosure provides isolated nucleic acids, where a nucleic acid of the present disclosure comprises a nucleotide sequence encoding a subject tau peptide. A nucleotide sequence encoding a tau peptide of the present disclosure can be operably linked to one or more regulatory elements, such as a promoter and/or an enhancer, that allow expression of the nucleotide sequence in the intended target cells (e.g., a cell that is genetically modified to synthesize the encoded tau peptide). In some embodiments, a subject nucleic acid is a recombinant expression vector.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and the like.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter, a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction.* Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a tau peptide of the present disclosure can be present in an expression vector and/or a cloning vector. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

The present disclosure provides isolated genetically modified host cells (e.g., in vitro cells) that are genetically modified with a subject nucleic acid. In some embodiments, a subject isolated genetically modified host cell can produce a tau peptide of the present disclosure.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302.

In some cases, a subject genetically modified host cell is a mammalian cell. Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some cases, a subject genetically modified host cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

Where a subject genetically modified host cell is a neuron, a nucleotide sequence encoding subject tau peptide can be operably linked to a neuron-specific control sequence (e.g., a neuron-specific promoter).

Suitable neuron-specific control sequences include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) *Cell* 51:7-19; and Llewellyn, et al. (2010) *Nat. Med.* 16(10):1161-1166); a serotonin receptor promoter (see, e.g., GenBank S62283); a tyrosine hydroxylase promoter (TH) (see, e.g., Oh et al. (2009) *Gene Ther* 16:437; Sasaoka et al. (1992) *Mol. Brain Res.* 16:274; Boundy et al. (1998) *J. Neurosci.* 18:9989; and Kaneda et al. (1991) *Neuron* 6:583-594); a GnRH promoter (see, e.g., Radovick et al. (1991) *Proc. Natl. Acad. Sci. USA* 88:3402-3406); an L7 promoter (see, e.g., Oberdick et al. (1990) *Science* 248:223-226); a DNMT promoter (see, e.g., Bartge et al. (1988) *Proc. Natl. Acad. Sci. USA* 85:3648-3652); an enkephalin promoter (see, e.g., Comb et al. (1988) *EMBO J.* 17:3793-3805); a myelin basic protein (MBP) promoter; a $Ca^{2+}$-calmodulin-dependent protein kinase II-alpha (CamKIIα) promoter (see, e.g., Mayford et al. (1996) *Proc. Natl. Acad. Sci. USA* 93:13250; and Casanova et al. (2001) *Genesis* 31:37); and a CMV enhancer/platelet-derived growth factor-β promoter (see, e.g., Liu et al. (2004) *Gene Therapy* 11:52-60).

In some instances, a neuronal cell that produces a subject tau peptide is differentiated in vitro from an induced pluripotent (iPS) cell generated from a somatic cell of an individual, e.g., an individual having a tauopathy. Methods of making such neurons are known in the art and are described below.

Tau Peptide Compositions

The present disclosure provides compositions ("tau peptide compositions"), including pharmaceutical compositions, comprising a subject tau peptide. In some cases, a subject tau peptide composition is an immunogenic composition.

A subject tau peptide composition can comprise, in addition to a subject tau peptide, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

In some instances, the tau peptides in a composition of tau peptides of the present disclosure are homogeneous with respect to amino acid sequence (e.g., sequence of amino acid residues without post-translational modification); and homogenous with respect to phosphorylation. In other cases, the tau peptides in a composition of tau peptides of the present disclosure are homogeneous with respect to amino acid sequence; and heterogeneous with respect to phosphorylation. For example, from about 2% to about 100% of the population can include at least one phosphorylated amino acid residue. For example, from about 2% to about 5%, from about 5% to about 10%, from about 10% to about 15%, from about 15% to about 20%, from about 20% to about 25%, from about 25% to about 30%, from about 30% to about 40%, from about 40% to about 50%, from about 50% to about 60%, from about 60% to about 70%, from about 70% to about 80%, from about 80% to about 90%, or from about 90% to 100%, of the tau peptides in a population of tau peptides of the present disclosure that are homogeneous with respect to amino acid sequence can include one, two, three, or more than three, phosphorylated amino acid residues (e.g., phosphorylated serine; phosphorylated threonine).

In some cases, a tau composition of the present disclosure is a pharmaceutical composition comprising: a) a tau peptide of the present disclosure; and b) a pharmaceutically acceptable excipient. A pharmaceutical composition of the present disclosure that comprises: a) a tau peptide of the present disclosure; and b) a pharmaceutically acceptable excipient can be a sterile composition. A pharmaceutical composition of the present disclosure that comprises: a) a tau peptide of the present disclosure; and b) a pharmaceutically acceptable excipient can be a composition that is suitable for use in humans. A pharmaceutical composition of the present disclosure that comprises: a) a tau peptide of the present disclosure; and b) a pharmaceutically acceptable excipient can be endotoxin free.

In some instances, a tau peptide composition comprising tau peptide of the present disclosure can comprise a pharmaceutically acceptable excipient, a variety of which are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds. $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Pharmaceutically acceptable carriers suitable for use with a subject tau peptide can include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a subject tau peptide can also be lyophilized using means well known in the art, for subsequent reconstitution and use according to the present disclosure.

A subject tau peptide can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, inhalants, and aerosols.

For oral preparations, a subject tau peptide can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject tau peptide can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject tau peptide are prepared by mixing the tau peptide having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-Methylglucosamine, galactosamine, and neuraminic acid; and/or non-ionic surfactants such as Tween, Brij Pluronics, Triton-X or polyethylene glycol (PEG).

A subject tau peptide pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

The concentration of a subject tau peptide in a pharmaceutical composition can range from about 0.5 mg/mL to about 1 mg/mL, from about 1 mg/mL to about 200 mg/ml, from about 50 mg/mL to about 200 mg/mL, or from about 150 mg/mL to about 200 mg/mL.

An aqueous formulation of a subject tau peptide may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the tau peptide formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the tau peptide formulation to reduce aggregation of the formulated peptide and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject tau peptide, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

A subject tau peptide can be utilized in aerosol formulation to be administered via inhalation. A subject tau peptide can be formulated into pressurized acceptable propellants such as dichlorodifluoromethane, propane, nitrogen and the like.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject tau peptide in a composition as a solution in sterile water, normal saline or another pharmaceutically acceptable carrier.

The term "unit dosage form," as used herein, refers to physically discrete units suitable as unitary dosages for human subjects and non-human animal subjects, each unit containing a predetermined quantity of a subject tau peptide, calculated in an amount sufficient to produce the desired effect in association with a pharmaceutically acceptable diluent, carrier or vehicle.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of the subject tau peptide by the nasal mucosa.

A subject tau peptide can be administered as an injectable formulation. Typically, injectable compositions are prepared as liquid solutions or suspensions; solid forms suitable for solution in, or suspension in, liquid vehicles prior to injection may also be prepared. The preparation may also be emulsified, or the peptide may be encapsulated in liposome vehicles.

In some cases, a subject tau peptide is formulated in a controlled release formulation. Sustained-release preparations may be prepared using methods well known in the art. Suitable examples of sustained-release preparations include semipermeable matrices of solid hydrophobic polymers containing the tau peptide in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid.

Liposomes can be used as a delivery vehicle. The lipids may be any useful combination of known liposome forming lipids, including cationic or zwitterionic lipids, such as phosphatidylcholine. The remaining lipid will normally include neutral or acidic lipids, such as cholesterol, phosphatidyl serine, phosphatidyl glycerol, and the like.

For preparing the liposomes, the procedure described by Kato et al (1991) J. Biol. Chem. 266:3361 may be used. Briefly, lipids and composition containing a subject peptide are combined in an appropriate aqueous medium, conveniently a saline medium where the total solids will be in the range of about 1-10 weight percent. After intense agitation for short periods of time, from about 5-60 seconds, the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Immunogenic Compositions

As noted above, in some cases, a subject tau peptide composition is an immunogenic composition. A subject immunogenic composition comprises: a) a subject tau peptide in an immunologically effective amount; and b) a pharmaceutically acceptable excipient. Immunogenic compositions can be provided in a pharmaceutically acceptable excipient, which can be a solution such as a sterile aqueous solution, e.g., a saline solution. Such excipients can be substantially inert, if desired. Suitable excipients include those listed above.

By "immunologically effective amount" is meant that the administration of that amount to an individual, either in a single dose, as part of a series of the same or different immunogenic compositions, is effective to elicit an immune response (e.g., a specific antibody response) to a subject tau peptide in the individual.

In some cases, a tau peptide in a subject immunogenic composition can be bound, covalently or non-covalently, to a carrier, as described above.

An immunogenic composition comprising a subject tau peptide can include an adjuvant. Suitable adjuvants include those suitable for use in humans. Examples of known suitable adjuvants that can be used in humans include, but are not necessarily limited to, alum, aluminum phosphate, aluminum hydroxide, MF59 (4.3% w/v squalene, 0.5% w/v polysorbate 80 (Tween 80), 0.5% w/v sorbitan trioleate (Span 85)), a CpG-containing nucleic acid (where the cytosine is unmethylated), QS21 (saponin adjuvant), MPL (Monophosphoryl Lipid A), 3DMPL (3-O-deacylated MPL), extracts from Aquilla, ISCOMS (see, e.g., Sjölander et al. (1998) J. Leukocyte Biol. 64:713), LT/CT mutants, poly(D,L-lactide-co-glycolide) (PLG) microparticles, Quil A, interleukins, and the like.

For veterinary applications including but not limited to animal experimentation, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in Vaccine design: the subunit and adjuvant approach, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), other TNF superfamily molecules (e.g., CH40L, OX40L, and the like), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg *Vaccine* 2000, 19, 618-622), e.g., containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IM2 (optionally+a sterol) e.g. WO98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. In some instances, the adjuvant is one that is suitable for use in humans.

An immunogenic composition comprising a tau peptide of the present disclosure may contain other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

Methods of Generating an Immune Response

The present disclosure provides methods of generating an immune response in an individual to a subject tau peptide. The methods generally involve administering to an individual an amount of a subject tau peptide that is effective to stimulate an immune response in the individual to the peptide. Generating an immune response in an individual to a subject tau peptide can result in one or more of: reduction in the amount of free extracellular tau peptide in brain tissue; reduction in the cell-to-cell spread (e.g., neuron-to-neuron spread) of tau peptides; reduction in the amount of tau aggregates (e.g., intracellular (e.g., intraneuronal) tau aggregates); and reduction in the amount of neurofibrillary tangles in brain tissue. Generating an immune response in an individual to a subject tau peptide can in some cases improve cognitive function in the individual, or at least reduce the rate of decline of cognitive function in the individual.

In some cases, a method of generating an immune response in an individual to a subject tau peptide reduces the amount of free extracellular tau peptide (e.g., the amount of free extracellular tau peptide in a brain tissue) by at least about 10%, at least about 20%, at least about 25%, at least about 50%, or more than 50%, compared to the amount of free extracellular tau peptide in the individual before administration with a subject tau peptide.

In some cases, a method of generating an immune response in an individual to a subject tau peptide reduces the cell-to-cell (e.g., neuron-to-neuron) spread of a tau peptide (e.g., a pathological tau peptide) by at least about 10%, at least about 20%, at least about 25%, at least about 50%, or more than 50%, compared to the cell-to-cell spread before administration with a subject tau peptide.

In some cases, a method of generating an immune response in an individual to a subject tau peptide reduces the amount of tau aggregates (e.g., intracellular (e.g., intraneuronal) tau aggregates) by at least about 10%, at least about 20%, at least about 25%, at least about 50%, or more than 50%, compared to the amount of tau aggregates before administration with a subject tau peptide.

In some cases, a method of generating an immune response in an individual to a subject tau peptide reduces neurotoxicity in an individual; and/or reduces neuroinflammation in an individual; and/or reduces activation of astrocytes and microglia; and/or reduces induction of pathological electrophysiological effects; and/or reduces the amount of tau in exosomes.

A tau peptide of the present disclosure can be administered to an individual in a formulation comprising the peptide and a pharmaceutically acceptable excipient. Pharmaceutical formulations comprising a subject tau peptide are described above and are suitable for use in a subject method of generating an immune response. For example, in some cases, an immunogenic composition comprising a subject tau peptide, as described above, is administered to an individual.

A tau peptide-containing immunogenic composition is generally administered in an amount effective to elicit an immune response, e.g., a humoral immune response, e.g., specific antibody response, in the host. Amounts for immunization will vary, and can range from about 1 µg to 100 µg per 70 kg patient, e.g., from 5 µg/70 kg to 50 µg/70 kg. Substantially higher dosages (e.g. 10 mg to 100 mg or more) may be suitable in oral, nasal, or topical administration routes. The initial administration can be followed by one or more booster immunizations of the same or different tau-containing immunogenic composition. Vaccination can involve at least one booster, or two or more boosters.

In general immunization can be accomplished by administration by any suitable route, including administration of the composition orally, nasally, nasopharyngeally, parenterally, enterically, gastrically, topically, transdermally, subcutaneously, intramuscularly, locally or systemically, where the immunogenic composition is in tablet, solid, powdered, liquid, aerosol form, with or without added excipients, and with or without an adjuvant. Actual methods for preparing enterally and parenterally administrable compositions are known to those skilled in the art and are described in more detail in such publications as Remington's Pharmaceutical Science, 15th ed., Mack Publishing Company, Easton, Pa. (1980).

An anti-tau immune response (e.g., an antibody response specific for a subject tau peptide) can be assessed by known methods (e.g. by obtaining serum from the individual before and after the initial immunization, and demonstrating a change in the individual's immune status, for example an immunoprecipitation assay, an enzyme-linked immunosorbent assay (ELISA), a Western blot, a flow cytometric assay, and the like).

Individuals in whom an immune response to a subject tau peptide may be desirable include individuals who have been diagnosed as having a tauopathy; individuals at greater risk than the general population for developing a tauopathy (e.g., individuals having a genetic predisposition to developing a tauopathy); and the like. In some cases, the individual is an adult human. In some cases, the adult human is 40 years of age or older, 50 years of age or older, 60 years of age or older, 70 years of age or older, or 80 years of age or older. For example, the adult human can be from 40 years old to 50 years old, from 50 years old to 60 years old, from 60 years old to 70 years old, or older than 70 years.

Antibodies

The present disclosure provides antibodies, e.g., isolated antibodies, specific for an eTau polypeptide, e.g., an eTau polypeptide of the present disclosure. An antibody of the present disclosure is also referred to as an "anti-tau antibody" or an "anti-eTau antibody." A subject anti-tau antibody finds use in various applications, including detection methods, diagnostic methods, and therapeutic methods. An anti-Tau antibody of the present disclosure binds extracellular tau. "Extracellular tau" ("eTau"), as used herein, encompasses any Tau polypeptide that can be detected in cerebrospinal fluid (CSF) or interstitial fluid (ISF).

In some cases, an anti-Tau antibody of the present disclosure binds soluble Tau polypeptide (e.g., a soluble eTau polypeptide of the present disclosure). In some cases, an anti-Tau antibody of the present disclosure binds soluble Tau polypeptide (e.g., a soluble eTau polypeptide of the present disclosure); and does not substantially bind aggregated Tau polypeptide. In some cases, an anti-Tau antibody of the present disclosure binds a linear epitope on a soluble Tau polypeptide (e.g., a soluble eTau polypeptide of the present disclosure). In some cases, an anti-Tau antibody of the present disclosure binds a neoepitope; for example, in some cases, the epitope recognized and bound by a subject anti-Tau antibody is not present in full-length Tau, but is generated upon cleavage of a Tau polypeptide to produce an extracellular Tau polypeptide. The neoepitope can be in a C-terminal region of the Tau polypeptide, or in an N-terminal region of the Tau polypeptide.

The present disclosure provides an isolated antibody that specifically binds an epitope within an eTau polypeptide of the present disclosure. The present disclosure provides an isolated monoclonal antibody that specifically binds an epitope within an eTau polypeptide of the present disclosure. The present disclosure provides an isolated humanized monoclonal antibody that specifically binds an epitope within an eTau polypeptide of the present disclosure.

The present disclosure provides an isolated antibody that specifically binds an epitope within an eTau-1 polypeptide of the present disclosure. An "eTau-1 polypeptide" includes, e.g., an eTau 2-166 polypeptide as depicted in FIG. 1A; an eTau 2-172 polypeptide as depicted in FIG. 1A; and an eTau 2-176 polypeptide as depicted in FIG. 1A. The present disclosure provides an isolated monoclonal antibody that specifically binds an epitope within an eTau-1 polypeptide of the present disclosure. The present disclosure provides an isolated humanized monoclonal antibody that specifically binds an epitope within an eTau-1 polypeptide of the present disclosure. In some cases, an isolated antibody of the present disclosure binds an eTau-1 polypeptide; and does not bind an eTau-2 polypeptide, an eTau-3 polypeptide, or an eTau-4 polypeptide. In some cases, an isolated antibody of the present disclosure binds an eTau-1 polypeptide, an eTau-2 polypeptide, an eTau-3 polypeptide, and an eTau-4 polypeptide.

The present disclosure provides an isolated antibody that specifically binds an epitope within an eTau-2 polypeptide of the present disclosure. The present disclosure provides an isolated monoclonal antibody that specifically binds an epitope within an eTau-2 polypeptide of the present disclosure. The present disclosure provides an isolated humanized monoclonal antibody that specifically binds an epitope within an eTau-2 polypeptide of the present disclosure. In some cases, an isolated antibody of the present disclosure binds an eTau-2 polypeptide; and does not bind an eTau-1 polypeptide, an eTau-3 polypeptide, or an eTau-4 polypeptide. In some cases, an isolated antibody of the present disclosure binds an eTau-1 polypeptide, an eTau-2 polypeptide, an eTau-3 polypeptide, and an eTau-4 polypeptide.

The present disclosure provides an isolated antibody that specifically binds an epitope within an eTau-3 polypeptide of the present disclosure. The present disclosure provides an isolated monoclonal antibody that specifically binds an epitope within an eTau-3 polypeptide of the present disclosure. The present disclosure provides an isolated humanized monoclonal antibody that specifically binds an epitope within an eTau-3 polypeptide of the present disclosure. In some cases, an isolated antibody of the present disclosure binds an eTau-3 polypeptide; and does not bind an eTau-1 polypeptide, an eTau-2 polypeptide, or an eTau-4 polypeptide. In some cases, an isolated antibody of the present disclosure binds an eTau-1 polypeptide, an eTau-2 polypeptide, an eTau-3 polypeptide, and an eTau-4 polypeptide.

The present disclosure provides an isolated antibody that specifically binds an epitope within an eTau-4 polypeptide of the present disclosure. The present disclosure provides an isolated monoclonal antibody that specifically binds an epitope within an eTau-4 polypeptide of the present disclosure. The present disclosure provides an isolated humanized monoclonal antibody that specifically binds an epitope within an eTau-4 polypeptide of the present disclosure. In some cases, an isolated antibody of the present disclosure binds an eTau-4 polypeptide; and does not bind an eTau-1 polypeptide, an eTau-2 polypeptide, or an eTau-3 polypeptide. In some cases, an isolated antibody of the present disclosure binds an eTau-1 polypeptide, an eTau-2 polypeptide, an eTau-3 polypeptide, and an eTau-4 polypeptide.

In some cases, an antibody specific for a subject tau peptide specifically binds an acetylated form of the tau peptide and does not substantially bind an unacetylated form of the peptide. In other cases, an antibody specific for a subject tau peptide specifically binds an unacetylated form of the peptide.

A subject anti-tau antibody can recognize a linear epitope in a tau peptide of the present disclosure, or can recognize a conformational epitope. In some cases, the epitope recognized by a subject anti-tau antibody is a linear epitope.

In some cases, a subject anti-tau antibody is a monoclonal antibody. In some cases, a subject anti-tau antibody is an antibody fragment, e.g., an Fab, an Fab', an F(ab')$_2$, a Fv fragment, a diabody, a linear antibody, a single-chain antibody, or other fragment capable of binding a subject tau peptide.

In some cases, an antibody that binds an epitope within amino acids 2-18 is specifically excluded. In some embodiments, an antibody that binds an epitope within 15-24 is specifically excluded. In some embodiments, an antibody that binds an epitope within amino acids 5-20 is specifically excluded. In some embodiments, an antibody that binds an epitope within amino acids 19-46 is specifically excluded. The amino acid numbering is based on the numbering of fetal Tau and of the eTau fragments depicted in FIGS. 1A and 1B.

In some cases, a Tau12 antibody (Ghoshal et al. (2002) *Exp. Neurobiol.* 177:475) is specifically excluded. In some cases, a Tau13 antibody (Garcia-Sierra et al. (2003) *J. Alz. Dis.* 5:65) is specifically excluded. In some cases, a TNT1 antibody (Kanaan et al. (2011) *J. Neurosci.* 31:9859) is specifically excluded. In some cases, a 5A6 antibody (Johnson et al. (1997). *J. Neurochemistry* 68(1):430-433) is specifically excluded. In some cases, a HJ9.4 antibody (Yanamandra et al. (2013) *Neuron* 80:402) is specifically excluded. In some embodiments, an HT7 antibody is specifically excluded. In some embodiments, a 6C10 antibody (US 2012/0183599) is specifically excluded.

The term "competes for binding" refers to the ability of a first antibody to inhibit binding of a second antibody to an epitope of an antigen. Where a first antibody does not compete with a second antibody for binding to an epitope, it can be considered that the first antibody does not bind the same epitope as the second antibody. Where a first antibody competes with a second antibody for binding to an epitope, it can be considered that the first antibody binds the same, or an overlapping, epitope as the second antibody. In some cases, where a first antibody competes with a second antibody for binding to an epitope, the second antibody does not bind to the epitope at a detectable level in the presence of the first antibody.

Assays for competitive binding are known in the art. For example, a competitive inhibition ELISA can be used. As an example, an antigen that includes an epitope that is recognized by a first antibody is immobilized on wells of a multi-well plate; the first antibody, which comprises a first detectable label, is allowed to bind the immobilized antigen, forming an immobilized antigen-first antibody complex; and a second antibody, which comprises a second detectable label (which second detectable label is distinguishable from the first detectable label), is contacted with the immobilized antigen-first antibody complex. Whether the second antibody competitively inhibits binding of the first antibody to the epitope recognized by the first antibody can be determined by detecting binding of the second antibody to the immobilized antigen (detected by the second detectable label), and reduction of binding of the first antibody (detected by reduction of the first detectable label).

[7295-M6]

The present disclosure provides an isolated antibody that binds an epitope in a Tau polypeptide (e.g., an eTau polypeptide of the present disclosure) wherein the antibody competes for binding to the epitope with an antibody that comprises light chain CDRs of an antibody light chain variable region comprising amino acid sequence SEQ ID NO:15 and heavy chain CDRs of an antibody heavy chain variable region comprising amino acid sequence SEQ ID NO:16. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

The present disclosure provides an isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:15. The present disclosure provides an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising amino acid sequence SEQ ID NO:16. The present disclosure provides an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:15 and heavy chain CDRs of an antibody heavy chain variable region comprising amino acid sequence SEQ ID NO:16. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

The present disclosure provides an isolated antibody that competes for binding to an epitope in a Tau polypeptide (e.g., an eTau polypeptide of the present disclosure) with an antibody that comprises: a) a light chain region comprising: i) a V$_L$ CDR1 comprising an amino acid sequence of SEQ ID NO:9; (ii) a V$_L$ CDR2 comprising an amino acid sequence of SEQ ID NO:10; and (iii) a V$_L$ CDR3 comprising an amino acid sequence of SEQ ID NO:11; and b) a heavy chain region comprising: (i) a V$_H$ CDR1 comprising an amino acid sequence of SEQ ID NO:12; (ii) a V$_H$ CDR2 comprising an amino acid sequence of SEQ ID NO:13; and (iii) a V$_H$ CDR3 comprising an amino acid sequence of SEQ ID NO:14. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

The present disclosure provides an isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:9; (ii) a $V_L$ CDR2 comprising an amino acid sequence of SEQ ID NO:10; (iii) a $V_L$ CDR3 comprising an amino acid sequence of SEQ ID NO:11; (iv) a $V_H$ CDR1 comprising an amino acid sequence of SEQ ID NO:12; (v) a $V_H$ CDR2 comprising an amino acid sequence of SEQ ID NO:13; and (vi) a $V_H$ CDR3 comprising an amino acid sequence of SEQ ID NO:14. In some cases, the antibody comprises: i) a $V_L$ CDR1 comprising an amino acid sequence of SEQ ID NO:9; (ii) a $V_L$ CDR2 comprising an amino acid sequence of SEQ ID NO:10; and (iii) a $V_L$ CDR3 comprising an amino acid sequence of SEQ ID NO:11. In some cases, the antibody comprises: (iv) a $V_H$ CDR1 comprising an amino acid sequence of SEQ ID NO:12; (v) a $V_H$ CDR2 comprising an amino acid sequence of SEQ ID NO:13; and (vi) a $V_H$ CDR3 comprising an amino acid sequence of SEQ ID NO:14. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

The present disclosure provides an isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:9; (ii) a $V_L$ CDR2 comprising an amino acid sequence of SEQ ID NO:10; and (iii) a $V_L$ CDR3 comprising an amino acid sequence of SEQ ID NO:11; and b) a heavy chain region comprising: (i) a $V_H$ CDR1 comprising an amino acid sequence of SEQ ID NO:12; (ii) a $V_H$ CDR2 comprising an amino acid sequence of SEQ ID NO:13; and (iii) a $V_H$ CDR3 comprising an amino acid sequence of SEQ ID NO:14. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77). [7295-M8]

The present disclosure provides an isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:23 and heavy chain CDRs of an antibody heavy chain variable region comprising amino acid sequence SEQ ID NO:24. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

The present disclosure provides an isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:23. The present disclosure provides an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising amino acid sequence SEQ ID NO:24. The present disclosure provides an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:23 and heavy chain CDRs of an antibody heavy chain variable region comprising amino acid sequence SEQ ID NO:24. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

The present disclosure provides an isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:17; (ii) a $V_L$ CDR2 comprising an amino acid sequence of SEQ ID NO:18; and (iii) a $V_L$ CDR3 comprising an amino acid sequence of SEQ ID NO:19; and b) a heavy chain region comprising: (i) a $V_H$ CDR1 comprising an amino acid sequence of SEQ ID NO:20; (ii) a $V_H$ CDR2 comprising an amino acid sequence of SEQ ID NO:21; and (iii) a $V_H$ CDR3 comprising an amino acid sequence of SEQ ID NO:22. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) Mol. Immunol. 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

The present disclosure provides an isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:17; (ii) a $V_L$ CDR2 comprising an amino acid sequence of SEQ ID NO:18; (iii) a $V_L$ CDR3 comprising an amino acid sequence of SEQ ID NO:19; (iv) a $V_H$ CDR1 comprising an amino acid sequence of SEQ ID NO:20; (v) a $V_H$ CDR2 comprising an amino acid sequence of SEQ ID NO:21; and (vi) a $V_H$ CDR3 comprising an amino acid sequence of SEQ ID NO:22. In some cases, the antibody comprises: i) a $V_L$ CDR1 comprising an amino acid sequence of SEQ ID NO:17; (ii) a $V_L$ CDR2 comprising an amino acid sequence of SEQ ID NO:18; and (iii) a $V_L$ CDR3 comprising an amino acid sequence of SEQ ID NO:19. In some cases, the antibody comprises: (iv) a $V_H$ CDR1 comprising an amino acid sequence of SEQ ID NO:20; (v) a $V_H$ CDR2 comprising an amino acid sequence of SEQ ID NO:21; and (vi) a $V_H$ CDR3 comprising an amino acid sequence of SEQ ID NO:22. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) Mol. Immunol. 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

The present disclosure provides an isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:17; (ii) a $V_L$ CDR2 comprising an amino acid sequence of SEQ ID NO:18; and (iii) a $V_L$ CDR3 comprising an amino acid sequence of SEQ ID NO:19; and b) a heavy chain region comprising: (i) a $V_H$ CDR1 comprising an amino acid sequence of SEQ ID NO:20; (ii) a $V_H$ CDR2 comprising an amino acid sequence of SEQ ID NO:21; and (iii) a $V_H$ CDR3 comprising an amino acid sequence of SEQ ID NO:22. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) Mol. Immunol. 30:105. In some cases, the antibody is a Fv, scFv, Fab, F(ab')2, or Fab'. In some cases, the antibody comprises a covalently linked non-peptide synthetic polymer, e.g., a poly(ethylene glycol)

polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77). [7298-M1]

The present disclosure provides an isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:31 and heavy chain CDRs of an antibody heavy chain variable region comprising amino acid sequence SEQ ID NO:32. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a $F(ab')_2$ fragment, a scFv, or a Fv. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

The present disclosure provides an isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:31. The present disclosure provides an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising amino acid sequence SEQ ID NO:32. The present disclosure provides an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:31 and heavy chain CDRs of an antibody heavy chain variable region comprising amino acid sequence SEQ ID NO:32. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a $F(ab')_2$ fragment, a scFv, or a Fv. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

The present disclosure provides an isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:25; (ii) a $V_L$ CDR2 comprising an amino acid sequence of SEQ ID NO:26; and (iii) a $V_L$ CDR3 comprising an amino acid sequence of SEQ ID NO:27; and b) a heavy chain region comprising: (i) a $V_H$ CDR1 comprising an amino acid sequence of SEQ ID NO:28; (ii) a $V_H$ CDR2 comprising an amino acid sequence of SEQ ID NO:29; and (iii) a $V_H$ CDR3 comprising an amino acid sequence of SEQ ID NO:30. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

The present disclosure provides an isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:25; (ii) a $V_L$ CDR2 comprising an amino acid sequence of SEQ ID NO:26; (iii) a $V_L$ CDR3 comprising an amino acid sequence of SEQ ID NO:27; (iv) a $V_H$ CDR1 comprising an amino acid sequence of SEQ ID NO:28; (v) a $V_H$ CDR2 comprising an amino acid sequence of SEQ ID NO:29; and (vi) a $V_H$ CDR3 comprising an amino acid sequence of SEQ ID NO:30. In some cases, the antibody comprises: i) a $V_L$ CDR1 comprising an amino acid sequence of SEQ ID NO:25; (ii) a $V_L$ CDR2 comprising an amino acid sequence of SEQ ID NO:26; and (iii) a $V_L$ CDR3 comprising an amino acid sequence of SEQ ID NO:27. In some cases, the antibody comprises: (iv) a $V_H$ CDR1 comprising an amino acid sequence of SEQ ID NO:28; (v) a $V_H$ CDR2 comprising an amino acid sequence of SEQ ID NO:29; and (vi) a $V_H$ CDR3 comprising an amino acid sequence of SEQ ID NO:30. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

The present disclosure provides an isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:25; (ii) a $V_L$CDR2 comprising an amino acid sequence of SEQ ID NO:26; and (iii) a $V_L$ CDR3 comprising an amino acid sequence of SEQ ID NO:27; and b) a heavy chain region comprising: (i) a $V_H$ CDR1 comprising an amino acid sequence of SEQ ID NO:28; (ii) a $V_H$ CDR2 comprising an amino acid sequence of SEQ ID NO:29; and (iii) a $V_H$ CDR3 comprising an amino acid sequence of SEQ ID NO:30. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

[7298-M2]

The present disclosure provides an isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:39 and heavy chain CDRs of an antibody heavy chain variable region comprising amino acid sequence SEQ ID NO:40. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

The present disclosure provides an isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:39. The present disclosure provides an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising amino acid sequence SEQ ID NO:40. The present disclosure provides an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:39 and heavy chain CDRs of an antibody heavy chain variable region comprising amino acid sequence SEQ ID NO:40. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

The present disclosure provides an isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:33; (ii) a $V_L$ CDR2 comprising an amino acid sequence of SEQ ID NO:34; and (iii) a $V_L$ CDR3 comprising an amino acid sequence of SEQ ID NO:35; and b) a heavy chain region comprising: (i) a $V_H$ CDR1 comprising an amino acid sequence of SEQ ID NO:36; (ii) a $V_H$ CDR2 comprising an amino acid sequence of SEQ ID NO:37; and (iii) a $V_H$ CDR3 comprising an amino acid sequence of SEQ ID NO:38. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

The present disclosure provides an isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:33; (ii) a $V_L$ CDR2 comprising an amino acid sequence of SEQ ID NO:34; (iii) a $V_L$ CDR3 comprising an amino acid sequence of SEQ ID NO:35; (iv) a $V_H$ CDR1 comprising an amino acid sequence of SEQ ID NO:36; (v) a $V_H$ CDR2 comprising an amino acid sequence of SEQ ID NO:37; and (vi) a $V_H$ CDR3 comprising an amino acid sequence of SEQ ID NO:38. In some cases, the antibody comprises: i) a $V_L$ CDR1 comprising an amino acid sequence of SEQ ID NO:33; (ii) a $V_L$ CDR2 comprising an amino acid sequence of SEQ ID NO:34; and (iii) a $V_L$ CDR3 comprising an amino acid sequence of SEQ ID NO:35. In some cases, the antibody comprises: (iv) a $V_H$ CDR1 comprising an amino acid sequence of SEQ ID NO:36; (v) a $V_H$ CDR2 comprising an amino acid sequence of SEQ ID NO:37; and (vi) a $V_H$ CDR3 comprising an amino acid sequence of SEQ ID NO:38. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

The present disclosure provides an isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:33; (ii) a $V_L$ CDR2 comprising an amino acid sequence of SEQ ID NO:34; and (iii) a $V_L$ CDR3 comprising an amino acid sequence of SEQ ID NO:35; and b) a heavy chain region comprising: (i) a $V_H$ CDR1 comprising an amino acid sequence of SEQ ID NO:36; (ii) a $V_H$ CDR2 comprising an amino acid sequence of SEQ ID NO:37; and (iii) a $V_H$ CDR3 comprising an amino acid sequence of SEQ ID NO:38. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

[7299-M2]

The present disclosure provides an isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:47 and heavy chain CDRs of an antibody heavy chain variable region comprising amino acid sequence SEQ ID NO:48. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

The present disclosure provides an isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:47. The present disclosure provides an isolated antibody that binds an epitope in a Tau polypeptide (e.g., an eTau polypeptide of the present disclosure)

wherein the antibody comprises a heavy chain comprising heavy chain CDRs of an antibody heavy chain variable region comprising amino acid sequence SEQ ID NO:48. The present disclosure provides an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:47 and heavy chain CDRs of an antibody heavy chain variable region comprising amino acid sequence SEQ ID NO:48. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

The present disclosure provides an isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:41; (ii) a $V_L$ CDR2 comprising an amino acid sequence of SEQ ID NO:42; and (iii) a $V_L$ CDR3 comprising an amino acid sequence of SEQ ID NO:43; and b) a heavy chain region comprising: (i) a $V_H$ CDR1 comprising an amino acid sequence of SEQ ID NO:44; (ii) a $V_H$ CDR2 comprising an amino acid sequence of SEQ ID NO:45; and (iii) a $V_H$ CDR3 comprising an amino acid sequence of SEQ ID NO:46. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

The present disclosure provides an isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:41; (ii) a $V_L$ CDR2 comprising an amino acid sequence of SEQ ID NO:42; (iii) a $V_L$ CDR3 comprising an amino acid sequence of SEQ ID NO:43; (iv) a $V_H$ CDR1 comprising an amino acid sequence of SEQ ID NO:44; (v) a $V_H$ CDR2 comprising an amino acid sequence of SEQ ID NO:45; and (vi) a $V_H$ CDR3 comprising an amino acid sequence of SEQ ID NO:46. In some cases, the antibody comprises: i) a $V_L$ CDR1 comprising an amino acid sequence of SEQ ID NO:41; (ii) a $V_L$ CDR2 comprising an amino acid sequence of SEQ ID NO:42; and (iii) a $V_L$ CDR3 comprising an amino acid sequence of SEQ ID NO:43. In some cases, the antibody comprises: (iv) a $V_H$ CDR1 comprising an amino acid sequence of SEQ ID NO:44; (v) a $V_H$ CDR2 comprising an amino acid sequence of SEQ ID NO:45; and (vi) a $V_H$ CDR3 comprising an amino acid sequence of SEQ ID NO:46. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

The present disclosure provides an isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:41; (ii) a $V_L$ CDR2 comprising an amino acid sequence of SEQ ID NO:42; and (iii) a $V_L$ CDR3 comprising an amino acid sequence of SEQ ID NO:43; and b) a heavy chain region comprising: (i) a $V_H$ CDR1 comprising an amino acid sequence of SEQ ID NO:44; (ii) a $V_H$ CDR2 comprising an amino acid sequence of SEQ ID NO:45; and (iii) a $V_H$ CDR3 comprising an amino acid sequence of SEQ ID NO:46. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

[7299-M5]

The present disclosure provides an isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:55 and heavy chain CDRs of an antibody heavy chain variable region comprising amino acid sequence SEQ ID NO:56. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

The present disclosure provides an isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:55. The present disclosure provides an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising amino acid sequence SEQ ID NO:56. The present disclosure provides an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:55 and heavy chain CDRs of an antibody heavy chain variable region comprising amino acid sequence SEQ ID NO:56. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

The present disclosure provides an isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:49; (ii) a $V_L$ CDR2 comprising an amino acid sequence of SEQ ID NO:50; and (iii) a $V_L$ CDR3 comprising an amino acid sequence of SEQ ID NO:51; and b) a heavy chain region comprising: (i) a $V_H$ CDR1 comprising an amino acid sequence of SEQ ID NO:52; (ii) a $V_H$ CDR2 comprising an amino acid sequence of SEQ ID NO:53 and (iii) a $V_H$ CDR3 comprising an amino acid sequence of SEQ ID NO:54. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

The present disclosure provides an isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:49; (ii) a $V_L$ CDR2 comprising an amino acid sequence of SEQ ID NO:50; (iii) a $V_L$ CDR3 comprising an amino acid sequence of SEQ ID NO:51; (iv) a $V_H$ CDR1 comprising an amino acid sequence of SEQ ID NO:52; (v) a $V_H$ CDR2 comprising an amino acid sequence of SEQ ID NO:53; and (vi) a $V_H$ CDR3 comprising an amino acid sequence of SEQ ID NO:54. In some cases, the antibody comprises: i) a $V_L$ CDR1 comprising an amino acid sequence of SEQ ID NO:49; (ii) a $V_L$ CDR2 comprising an amino acid sequence of SEQ ID NO:50; and (iii) a $V_L$ CDR3 comprising an amino acid sequence of SEQ ID NO:51. In some cases, the antibody comprises: (iv) a $V_H$ CDR1 comprising an amino acid sequence of SEQ ID NO:52; (v) a V$_H$ CDR2 comprising an amino acid sequence of SEQ ID NO:53; and (vi) a V$_H$ CDR3 comprising an amino acid sequence of SEQ ID NO:54. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant (K$_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

The present disclosure provides an isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a V$_L$ CDR1 comprising an amino acid sequence of SEQ ID NO:49; (ii) a V$_L$ CDR2 comprising an amino acid sequence of SEQ ID NO:50; and (iii) a V$_L$ CDR3 comprising an amino acid sequence of SEQ ID NO:51; and b) a heavy chain region comprising: (i) a V$_H$ CDR1 comprising an amino acid sequence of SEQ ID NO:52; (ii) a V$_H$ CDR2 comprising an amino acid sequence of SEQ ID NO:53; and (iii) a V$_H$ CDR3 comprising an amino acid sequence of SEQ ID NO:54. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant (K$_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

[7299-M9]

The present disclosure provides an isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:63 and heavy chain CDRs of an antibody heavy chain variable region comprising amino acid sequence SEQ ID NO:64. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

The present disclosure provides an isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:63. The present disclosure provides an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:64. The present disclosure provides an isolated antibody that binds an epitope in a Tau polypeptide (e.g., an eTau polypeptide of the present disclosure) wherein the antibody comprises light chain CDRs of an antibody light chain variable region comprising the amino acid sequence SEQ ID NO:63 and heavy chain CDRs of an antibody heavy chain variable region comprising the amino acid sequence SEQ ID NO:64. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

The present disclosure provides an isolated antibody that competes for binding to an epitope in a Tau polypeptide (e.g., an eTau polypeptide of the present disclosure) with an antibody that comprises: a) a light chain region comprising: i) a V$_L$ CDR1 comprising an amino acid sequence of SEQ ID NO:57; (ii) a V$_L$ CDR2 comprising an amino acid sequence of SEQ ID NO:58; and (iii) a V$_L$ CDR3 comprising an amino acid sequence of SEQ ID NO:59; and b) a heavy chain region comprising: (i) a V$_H$ CDR1 comprising an amino acid sequence of SEQ ID NO:60; (ii) a V$_H$ CDR2 comprising an amino acid sequence of SEQ ID NO:61; and (iii) a V$_H$ CDR3 comprising an amino acid sequence of SEQ ID NO:62. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

The present disclosure provides an isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:57; (ii) a $V_L$ CDR2 comprising an amino acid sequence of SEQ ID NO:58; (iii) a $V_L$ CDR3 comprising an amino acid sequence of SEQ ID NO:59; (iv) a $V_H$ CDR1 comprising an amino acid sequence of SEQ ID NO:60; (v) a $V_H$ CDR2 comprising an amino acid sequence of SEQ ID NO:61; and (vi) a $V_H$ CDR3 comprising an amino acid sequence of SEQ ID NO:62. In some cases, the antibody comprises: i) a $V_L$ CDR1 comprising an amino acid sequence of SEQ ID NO:57; (ii) a $V_L$ CDR2 comprising an amino acid sequence of SEQ ID NO:58; and (iii) a $V_L$ CDR3 comprising an amino acid sequence of SEQ ID NO:59. In some cases, the antibody comprises: (iv) a $V_H$ CDR1 comprising an amino acid sequence of SEQ ID NO:60; (v) a $V_H$ CDR2 comprising an amino acid sequence of SEQ ID NO:61; and (vi) a $V_H$ CDR3 comprising an amino acid sequence of SEQ ID NO:62. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

The present disclosure provides an isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:57; (ii) a $V_L$ CDR2 comprising an amino acid sequence of SEQ ID NO:58; and (iii) a $V_L$ CDR3 comprising an amino acid sequence of SEQ ID NO:59; and b) a heavy chain region comprising: (i) a $V_H$ CDR1 comprising an amino acid sequence of SEQ ID NO:60; (ii) a $V_H$ CDR2 comprising an amino acid sequence of SEQ ID NO:61; and (iii) a $V_H$ CDR3 comprising an amino acid sequence of SEQ ID NO:62. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

[7297-2M1]

The present disclosure provides an isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:71 and heavy chain CDRs of an antibody heavy chain variable region comprising amino acid sequence SEQ ID NO:72. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

The present disclosure provides an isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:71. The present disclosure provides an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:72. The present disclosure provides an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:71 and heavy chain CDRs of an antibody heavy chain variable region comprising amino acid sequence SEQ ID NO:72. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

The present disclosure provides an isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:65; (ii) a $V_L$ CDR2 comprising an amino acid sequence of SEQ ID NO:66; and (iii) a $V_L$ CDR3 comprising an amino acid sequence of SEQ ID NO:67; and b) a heavy chain region comprising: (i) a $V_H$ CDR1 comprising an amino acid sequence of SEQ ID NO:68; (ii) a $V_H$ CDR2 comprising an amino acid sequence of SEQ ID NO:69; and (iii) a $V_H$ CDR3 comprising an amino acid sequence of SEQ ID NO:70. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

The present disclosure provides an isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:65; (ii) a $V_L$ CDR2 comprising an amino acid sequence of SEQ ID NO:66; (iii) a $V_L$ CDR3 comprising an amino acid sequence of SEQ ID NO:67; (iv) a $V_H$ CDR1 comprising an amino acid sequence of SEQ ID NO:68; (v) a $V_H$ CDR2 comprising an amino acid sequence of SEQ ID NO:69; and (vi) a $V_H$ CDR3 comprising an amino acid sequence of SEQ ID NO:70. In some cases, the antibody comprises: i) a $V_L$ CDR1 comprising an amino acid sequence of SEQ ID NO:65; (ii) a $V_L$ CDR2 comprising an amino acid sequence of SEQ ID NO:66; and (iii) a $V_L$ CDR3 comprising an amino acid sequence of SEQ ID NO:67. In some cases, the antibody comprises: (iv) a $V_H$ CDR1 comprising an amino acid sequence of SEQ ID NO:68; (v) a $V_H$ CDR2 comprising an amino acid sequence of SEQ ID NO:69; and (vi) a $V_H$ CDR3 comprising an amino acid sequence of SEQ ID NO:70. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

The present disclosure provides an isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:65; (ii) a $V_L$ CDR2 comprising an amino acid sequence of SEQ ID NO:66; and (iii) a $V_L$ CDR3 comprising an amino acid sequence of SEQ ID NO:67; and b) a heavy chain region comprising: (i) a $V_H$ CDR1 comprising an amino acid sequence of SEQ ID NO:68; (ii) a $V_H$ CDR2 comprising an amino acid sequence of SEQ ID NO:69; and (iii) a $V_H$ CDR3 comprising an amino acid sequence of SEQ ID NO:70. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

Recombinant Antibody

A subject anti-tau antibody can be recombinant. The antibody can contain a light and/or heavy chain. Methods for producing recombinant antibodies are known in the art. For example, the nucleic acids encoding the antibody, or at least a complementary determining region (CDR) of a heavy chain polypeptide or at least a CDR of a light chain polypeptide, are introduced directly into a host cell, and the cell incubated under conditions sufficient to induce expression of the encoded antibody. The recombinant antibody may be glycosylated by an endogenous glycosylase in the host cells; the recombinant antibody may be unglycosylated; or the recombinant antibody may have an altered glycosylation pattern.

Where the antibody is recombinant, the antibody may be chimeric. Chimeric antibodies are immunoglobulin molecules comprising human and non-human portions. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody can have the antigen binding specificity of the non-human antibody molecule and the effector function conferred by the human antibody molecule. A large number of methods of generating chimeric antibodies are well known to those of skill in the art. An alternative approach is the generation of humanized antibodies by linking the CDR regions of non-human antibodies to human constant regions by recombinant DNA techniques.

A recombinant fusion antibody that is specific for a subject tau peptide is contemplated, in which the antibody is modified to include a heterologous protein. For example, a heavy chain polypeptide and/or light chain polypeptide may be joined to a reporter protein or to a protein having a desired therapeutic effect. The reporter protein may be a fluorescent protein. The antibody may also be conjugated to a second antibody (or at least an antigen-binding portion thereof). Methods for producing a fusion protein of interest when provided a nucleic acid sequence are well known in the art.

Humanized and Human Antibodies

Humanization of a framework region(s) reduces the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of the therapy. The HAMA response is measured, for example, by detecting antibodies to the humanized therapeutic reagent, in serum samples from the patient using a method known to one in the art, including surface plasmon resonance technology (BIA-CORE) and/or solid-phase enzyme-linked immunosorbent assay (ELISA) analysis. In many cases, a subject humanized anti-Tau antibody does not substantially elicit a HAMA response in a human subject. In some cases, a subject humanized anti-Tau antibody has reduced immunogenic potential, as determined by an EpiScreen™ assay performed using CD8⁺-depleted peripheral blood mononuclear cells. In some cases, a subject humanized anti-Tau antibody exhibits a Stimulation Index of less than 2.0.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, e.g., those sharing at least 60%, 70%, 80%, 90%, or more than 90%, sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

A subject anti-tau antibody will in some embodiments be humanized. Amino acids may be substituted in the framework regions of a parent non-human (e.g., mouse monoclonal) antibody to produce a modified antibody that is less immunogenic in a human than the parent non-human antibody. Antibodies can be humanized using a variety of techniques known in the art. Framework substitutions are identified by modeling of the interactions of the CDR and framework residues to identify framework residues important for antigen binding and sequence comparison to identify unusual framework residues at particular positions.

The antibody may also be a fully human antibody. Human antibodies are primarily composed of characteristically human polypeptide sequences. A subject human antibody can be produced by a wide variety of methods. For example, human antibodies can be produced initially in trioma cells (descended from three cells, two human and one mouse). Genes encoding the antibodies are then cloned and expressed in other cells, particularly non-human mammalian cells. The general approach for producing human antibodies by trioma technology has been described in the art.

Accordingly, the present disclosure contemplates a DNA molecule comprising a nucleic acid sequence encoding an antibody that binds to a tau peptide of the present disclosure. The disclosure further contemplates recombinant host cells containing an exogenous polynucleotide encoding at least a CDR of a heavy chain polypeptide or at least a CDR of a light chain polypeptide of the subject antibody.

scFv

In some embodiments, a subject antibody comprises anti-tau antibody heavy chain CDRs and anti-tau antibody light chain CDRs in a single polypeptide chain, e.g., in some embodiments, a subject antibody is a scFv. In some embodiments, a subject antibody comprises, in order from N-terminus to C-terminus: a first amino acid sequence of from about 5 amino acids to about 25 amino acids in length; a heavy chain CDR1 of an anti-tau antibody; a second amino acid sequence of from about 5 amino acids to about 25 amino acids in length; a heavy chain CDR2 of an anti-tau antibody; a third amino acid sequence of from about 5 amino acids to about 25 amino acids in length; a heavy chain CDR3 of an anti-tau antibody; a fourth amino acid sequence of from about 5 amino acids to about 25 amino acids in length; a light chain CDR1 of an anti-tau antibody; a fifth amino acid sequence of from about 5 amino acids to about 25 amino acids in length; a light chain CDR2 an anti-tau antibody; a sixth amino acid sequence of from about 5 amino acids to about 25 amino acids in length; a light chain CDR3 an anti-tau antibody; and a seventh amino acid sequence of from about 5 amino acids to about 25 amino acids in length.

In some embodiments, a subject anti-tau antibody comprises scFv multimers. For example, in some embodiments, a subject anti-tau antibody is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFV multimer is humanized, as described above.

Antibody Modifications

A subject anti-tau antibody can comprise one or more modifications.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to a subject antibody that comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers.

Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., poly(ethylene oxide)-poly(lactic acid) (PEO/PLA) copolymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and may be found in, e.g., U.S. Pat. No. 5,849,860. PEG suitable for conjugation to a protein is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., the antibody can comprise a covalently linked carbohydrate or polysaccharide moiety. Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidohexane (BMH), 1,5-difluoro-2,4-dinitrobenzene (DFDNB), and 1,4-di-(3',2'-pyridyldithio) propionamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

Immobilization

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

Detectable Labels

A subject antibody will in some embodiments comprise a detectable label. Suitable detectable labels include any composition detectable by spectroscopic, photochemical, biochemical, immunochemical, electrical, optical or chemical means. Suitable detectable labels include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-diphenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from Aequoria victoria or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) Nature Biotechnol. 17:969-973; and the like.

Fusion Partners

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., glutathione-S-transferase (GST), hemagglutinin (HA; e.g., YPYDVPDYA; SEQ ID NO:74), FLAG (e.g., DYKDDDDK; SEQ ID NO:75), c-myc (e.g., EQKLISEEDL; SEQ ID NO:76), and the like; provide a detectable signal, e.g., an enzyme that generates a detectable product (e.g., β-galactosidase, luciferase, horse radish peroxidase, alkaline phosphatase, and the like), or a protein that is itself detectable, e.g., a green fluorescent protein, a red fluorescent protein, a yellow fluorescent protein, etc.; provides for multimerization; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include (His)$_5$ (HHHHH) (SEQ ID NO:81), (His)$_6$ (HHHHHH) (SEQ ID NO:82), C-myc (EQKLISEEDL) (SEQ ID NO:76), Flag (DYKDDDDK) (SEQ ID NO:75), StrepTag (WSHPQFEK) (SEQ ID NO:83), hemagglutinin, e.g., HA Tag (YPYDVPDYA; SEQ ID NO:74), glutathinone-S-transferase (GST), thioredoxin, cellulose binding domain, RYIRS (SEQ ID NO:84), Phe-His-His-Thr (SEQ ID NO:85), chitin binding domain, S-peptide, T7 peptide, SH2 domain, C-end RNA tag, WEAAAREACCRECCARA (SEQ ID NO:86), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

Additional Modifications

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated into a liposome.

A subject anti-tau antibody can be modified to include a moiety that modifies cellular uptake relative to unconjugated material. The modified antibody may exhibit increased cellular uptake relative to unconjugated material. In alternative embodiments, the modified antibody exhibits decreased cellular uptake relative to unmodified antibody. In this aspect, the efficiency of cellular uptake can be increased or decreased by linking to peptides or proteins that facilitate endocytosis. For example, a given antibody can be linked to a ligand for a target receptor or large molecule that is more easily engulfed by endocytotic mechanisms, such as another antibody. The antibody or other ligand can then be internalized by endocytosis and the payload released by acid hydrolysis or enzymatic activity when the endocytotic vesicle fuses with lysosomes. As such, the conjugate may be one that increases endocytosis relative to unconjugated antibody. To decrease cellular uptake, the modified antibody can include a ligand that retains the antibody on the surface of a cell, which can be useful as a control for cellular uptake, or in some instances decrease uptake in one cell type while increasing it in others.

A subject anti-tau antibody can comprise one or more moieties, which moieties may be linked (e.g., covalently or non-covalently linked) to the anti-tau antibody, either directly or via a linker, e.g. a flexible linker. For example, where a subject anti-tau antibody is a fusion protein comprising an anti-tau antibody and a heterologous fusion partner polypeptide, the heterologous fusion partner can be linked to the anti-tau antibody via a linker.

Linkers suitable for use in attaching a moiety to a subject anti-tau antibody include "flexible linkers". If present, the linker molecules are generally of sufficient length to permit the anti-tau antibody and a linked carrier to allow some flexible movement between the anti-tau antibody and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a variety of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers, where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited GGSG (SEQ ID NO:87), GGSGG (SEQ ID NO:88), GSGSG (SEQ ID NO:89), GSGGG (SEQ ID NO:90), GGGSG (SEQ ID NO:91), GSSSG (SEQ ID NO:92), and the like. The ordinarily skilled artisan will recognize that design of a peptide conjugated to any elements described above can include linkers that are all or partially flexible, such that the linker can include a flexible linker as well as one or more portions that confer less flexible structure.

Methods of Generating Anti-Tau Antibody

A subject antibody can be produced by any known method, e.g., conventional synthetic methods for protein synthesis; recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce an anti-tau antibody of the present disclosure (e.g., polynucleotides encoding a subject anti-Tau antibody). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Nucleic Acids Encoding an Anti-Tau Antibody

The present disclosure provides nucleic acids comprising nucleotide sequences encoding a subject anti-Tau antibody. The present disclosure provides a recombinant expression vector comprising a nucleotide sequence encoding an anti-Tau antibody of the present disclosure, wherein the nucleotide sequence is operably linked to a transcriptional control element that is active in a eukaryotic cell. The present disclosure provides an in vitro host cell (e.g., a bacterial cell; a eukaryotic cell, such as a yeast cell or a mammalian cell line) genetically modified with a recombinant expression vector of the present disclosure.

A nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL1 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No.

20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject antibody can be present in an expression vector and/or a cloning vector. Where a subject antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, a subject nucleic acid comprises a nucleotide sequence encoding a subject antibody. A subject nucleic acid can comprise a nucleotide sequence encoding heavy-chain CDRs and/or light-chain CDRs of a subject antibody. In some embodiments, a subject nucleic acid comprises a nucleotide sequence encoding heavy-chain CDRs and/or light-chain CDRs of a subject antibody, where the CDR-encoding sequences are interspersed with FR-encoding nucleotide sequences. In some embodiments, the FR-encoding nucleotide sequences are human FR-encoding nucleotide sequences.

Host Cells

The present disclosure provides isolated genetically modified host cells (e.g., in vitro cells) that are genetically modified with a subject nucleic acid. In some embodiments, a subject isolated genetically modified host cell can produce a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. In some cases, the cells are HEK cells. In some cases, the cells are CHO cells, e.g., CHO-K1 cells (ATCC No. CCL-61), CHO-M cells, CHO-DG44 cells (ATCC No. PTA-3356), and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli*, *Lactobacillus* sp., and the like. See, e.g., Carrier et al. (1992) *J. Immunol.* 148:1176-1181; U.S. Pat. No. 6,447,784; and Sizemore et al. (1995) *Science* 270:299-302. Typically, the laboratory strain is one that is non-pathogenic. Non-limiting examples of other suitable bacteria include, but are not limited to, *Bacillus subtilis*, and the like. In some embodiments, the host cell is *Escherichia coli*.

Pharmaceutical Formulations

The present disclosure provides compositions, including pharmaceutical compositions, comprising a subject antibody. In general, a formulation comprises an effective amount of a subject antibody. An "effective amount" means a dosage sufficient to produce a desired result, e.g., reduction in an adverse symptom associated with a tauopathy, amelioration of a symptom of a tauopathy, slowing progression of a tauopathy, etc. Generally, the desired result is at least a reduction in a symptom of a tauopathy, as compared to a control. A subject antibody can be delivered in such a manner as to avoid the blood-brain barrier, as described in more detail below. A subject antibody can be formulated and/or modified to enable the antibody to cross the blood-brain barrier. A suitable pharmaceutically acceptable excipient is in some embodiments suitable for administration to a human; e.g., suitable pharmaceutically acceptable excipient can be free of endotoxins.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlorm-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM Sucrose; and has a pH of 5.5; or 4) 75 mg/mL of a subject antibody; 0.04% Tween 20 w/v; 20 mM L-histidine; and 250 mM trehalose; and has a pH of 5.5; or 6) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.022% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an anti-Tau antibody of the present disclosure, calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

Other modes of administration will also find use with a method of the present disclosure. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of the subject antibody by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(-)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of the present disclosure can be taken to mean any one of a number of extended release dosage forms. The following terms may be considered to be substantially equivalent to controlled release, for the purposes of the present disclosure: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Treatment Methods

The present disclosure provides a method of treating a tauopathy in an individual. The method generally involves administering to an individual having a tauopathy an effective amount of an antibody that specifically binds an eTau polypeptide. For example, in some embodiments, the method generally involves administering to an individual having a tauopathy an effective amount of a subject anti-eTau antibody. In some cases, administration of an anti-eTau antibody, e.g., a subject anti-eTau antibody, reduces the level of a pathological tau peptide in a tissue of an individual, and treats the tauopathy.

In some embodiments of a method of the present disclosure, an anti-Tau antibody that is administered to an individual is encapsulated in a liposome. In some cases, the antibody is formulated with an agent that facilitates crossing the blood-brain barrier. In some cases, the antibody is fused, directly or via a linker, to a carrier molecule, a peptide or a protein that promotes the crossing of the blood-brain barrier. In some cases, the antibody is a Fv, scFv, Fab, F(ab')2, or Fab'. In some cases, the administering is intravenous. In some cases, the administering is intrathecal. In some cases, the administering is subcutaneous.

A method of the present disclosure for treating a tauopathy can comprise administering to an individual in need thereof an anti-Tau antibody, where suitable anti-Tau antibodies include:

1) An isolated antibody that binds an epitope in a Tau polypeptide (e.g., an eTau polypeptide of the present disclosure) wherein the antibody competes for binding to the epitope with an antibody that comprises light chain CDRs of an antibody light chain variable region comprising amino acid sequence SEQ ID NO:15 and heavy chain CDRs of an antibody heavy chain variable region comprising amino acid sequence SEQ ID NO:16. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

2) An isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:15; an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:16; or an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:15 and heavy chain CDRs of an antibody heavy chain variable region comprising amino acid sequence SEQ ID NO:16. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

3) An isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:9; (ii) a $V_L$ CDR2 comprising an amino acid sequence of SEQ ID NO:10; and (iii) a $V_L$ CDR3 comprising an amino acid sequence of SEQ ID NO:11; and b) a heavy chain region comprising: (i) a $V_H$ CDR1 comprising an amino acid sequence of SEQ ID NO:12; (ii) a $V_H$ CDR2 comprising an amino acid sequence of SEQ ID NO:13; and (iii) a $V_H$ CDR3 comprising an amino acid sequence of SEQ ID NO:14. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) Mol. Immunol. 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

4) An isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:9; (ii) a $V_L$ CDR2 comprising an amino acid sequence of SEQ ID NO:10; (iii) a $V_L$ CDR3 comprising an amino acid sequence of SEQ ID NO:11; (iv) a $V_H$ CDR1 comprising an amino acid sequence of SEQ ID NO:12; (v) a $V_H$ CDR2 comprising an amino acid sequence of SEQ ID NO:13; and (vi) a $V_H$ CDR3 comprising an amino acid sequence of SEQ ID NO:14. In some cases, the antibody comprises: i) a $V_L$ CDR1 comprising an amino acid sequence of SEQ ID NO:9; (ii) a $V_L$ CDR2 comprising an amino acid sequence of SEQ ID NO:10; and (iii) a $V_L$ CDR3 comprising an amino acid sequence of SEQ ID NO:11. In some cases, the antibody comprises: (iv) a $V_H$ CDR1 comprising an amino acid sequence of SEQ ID NO:12; (v) a $V_H$ CDR2 comprising an amino acid sequence of SEQ ID NO:13; and (vi) a $V_H$ CDR3 comprising an amino acid sequence of SEQ ID NO:14. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

5) An isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:9; (ii) a $V_L$ CDR2 comprising an amino acid sequence of SEQ ID NO:10; and (iii) a $V_L$ CDR3 comprising an amino acid sequence of SEQ ID NO:11; and b) a heavy chain region comprising: (i) a $V_H$ CDR1 comprising an amino acid sequence of SEQ ID NO:12; (ii) a $V_H$ CDR2 comprising an amino acid sequence of SEQ ID NO:13; and (iii) a $V_H$ CDR3 comprising an amino acid sequence of SEQ ID NO:14. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

6) An isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:23 and heavy chain CDRs of an antibody heavy chain variable region comprising amino acid sequence SEQ ID NO:24. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

7) An isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:23; an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:24; or an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:23 and heavy chain CDRs of an antibody heavy chain variable region comprising amino acid sequence SEQ ID NO:24. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

8) An isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:17; (ii) a $V_L$ CDR2 comprising an amino acid sequence of SEQ ID NO:18; and (iii) a $V_L$ CDR3 comprising an amino acid sequence of SEQ ID NO:19; and b) a heavy chain region comprising: (i) a $V_H$ CDR1 comprising an amino acid sequence of SEQ ID NO:20; (ii) a $V_H$ CDR2 comprising an amino acid sequence of SEQ ID NO:21; and (iii) a $V_H$ CDR3 comprising an amino acid sequence of SEQ ID NO:22. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

9) An isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:17; (ii) a $V_L$ CDR2 comprising an amino acid sequence of SEQ ID NO:18; (iii) a $V_L$ CDR3 comprising an amino acid sequence of SEQ ID NO:19; (iv) a $V_H$ CDR1 comprising an amino acid sequence of SEQ ID NO:20; (v) a $V_H$ CDR2 comprising an amino acid sequence of SEQ ID NO:21; and (vi) a $V_H$ CDR3 comprising an amino acid sequence of SEQ ID NO:22. In some cases, the antibody comprises: i) a $V_L$ CDR1 comprising an amino acid sequence of SEQ ID NO:17; (ii) a $V_L$ CDR2 comprising an amino acid sequence of SEQ ID NO:18; and (iii) a $V_L$ CDR3 comprising an amino acid sequence of SEQ ID NO:19. In some cases, the antibody comprises: (iv) a $V_H$ CDR1 comprising an amino acid sequence of SEQ ID NO:20; (v) a $V_H$ CDR2 comprising an amino acid sequence of SEQ ID NO:21; and (vi) a $V_H$ CDR3 comprising an amino acid sequence of SEQ ID NO:22. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

10) An isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:17; (ii) a $V_L$ CDR2 comprising an amino acid sequence of SEQ ID NO:18; and (iii) a $V_L$ CDR3 comprising an amino acid sequence of SEQ ID NO:19; and b) a heavy chain region comprising: (i) a $V_H$ CDR1 comprising an amino acid sequence of SEQ ID NO:20; (ii) a $V_H$ CDR2 comprising an amino acid sequence of SEQ ID NO:21; and (iii) a $V_H$ CDR3 comprising an amino acid sequence of SEQ ID NO:22. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, and does not bind an eTau2, an eTau3, or an eTau4 polypeptide. In some cases, the antibody binds an epitope within the amino acid sequence SLPTPPTREPK (SEQ ID NO:77).

11) An isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:31 and heavy chain CDRs of an antibody heavy chain variable region comprising amino acid sequence SEQ ID NO:32. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

12) An isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:31; an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:32; or an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:31 and heavy chain CDRs of an antibody heavy chain variable region comprising amino acid sequence SEQ ID NO:32. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

13) An isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:25; (ii) a $V_L$ CDR2 comprising an amino acid sequence of SEQ ID NO:26; and (iii) a $V_L$ CDR3 comprising an amino acid sequence of SEQ ID NO:27; and b) a heavy chain region comprising: (i) a $V_H$ CDR1 comprising an amino acid sequence of SEQ ID NO:28; (ii) a $V_H$ CDR2 comprising an amino acid sequence of SEQ ID NO:29; and (iii) a $V_H$ CDR3 comprising an amino acid sequence of SEQ ID NO:30. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

14) An isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:25; (ii) a $V_L$ CDR2 comprising an amino acid sequence of SEQ ID NO:26; (iii) a $V_L$ CDR3 comprising an amino acid sequence of SEQ ID NO:27; (iv) a $V_H$ CDR1 comprising an amino acid sequence of SEQ ID NO:28; (v) a $V_H$ CDR2 comprising an amino acid sequence of SEQ ID NO:29; and (vi) a $V_H$ CDR3 comprising an amino acid sequence of SEQ ID NO:30. In some cases, the antibody comprises: i) a $V_L$ CDR1 comprising an amino acid sequence of SEQ ID NO:25; (ii) a $V_L$ CDR2 comprising an amino acid sequence of SEQ ID NO:26; and (iii) a $V_L$ CDR3 comprising an amino acid sequence of SEQ ID NO:27. In some cases, the antibody comprises: (iv) a $V_H$ CDR1 comprising an amino acid sequence of SEQ ID NO:28; (v) a $V_H$ CDR2 comprising an amino acid sequence of SEQ ID NO:29; and (vi) a $V_H$ CDR3 comprising an amino acid sequence of SEQ ID NO:30. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

15) An isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:25; (ii) a $V_L$ CDR2 comprising an amino acid sequence of SEQ ID NO:26; and (iii) a $V_L$ CDR3 comprising an amino acid sequence of SEQ ID NO:27; and b) a heavy chain region comprising: (i) a $V_H$ CDR1 comprising an amino acid sequence of SEQ ID NO:28; (ii) a $V_H$ CDR2 comprising an amino acid sequence of SEQ ID NO:29; and (iii) a $V_H$ CDR3 comprising an amino acid sequence of SEQ ID NO:30. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

16) An isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:39 and heavy chain CDRs of an antibody heavy chain variable region comprising amino acid sequence SEQ ID NO:40. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

17) An isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:39; an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:40; or an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:39 and heavy chain CDRs of an antibody heavy chain variable region comprising amino acid sequence SEQ ID NO:40. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

18) An isolated antibody that competes for binding to an epitope in a Tau polypeptide (e.g., an eTau polypeptide of the present disclosure) with an antibody that comprises: a) a light chain region comprising: i) a V$_L$ CDR1 comprising an amino acid sequence of SEQ ID NO:33; (ii) a V$_L$ CDR2 comprising an amino acid sequence of SEQ ID NO:34; and (iii) a V$_L$ CDR3 comprising an amino acid sequence of SEQ ID NO:35; and b) a heavy chain region comprising: (i) a V$_H$ CDR1 comprising an amino acid sequence of SEQ ID NO:36; (ii) a V$_H$ CDR2 comprising an amino acid sequence of SEQ ID NO:37; and (iii) a V$_H$ CDR3 comprising an amino acid sequence of SEQ ID NO:38. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant (K$_D$) of 10$^{-7}$ M, 10$^{-8}$ M, 10$^{-9}$ M, 10$^{-10}$ M, or 10$^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

19) An isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a V$_L$ CDR1 comprising an amino acid sequence of SEQ ID NO:33; (ii) a V$_L$ CDR2 comprising an amino acid sequence of SEQ ID NO:34; (iii) a V$_L$ CDR3 comprising an amino acid sequence of SEQ ID NO:35; (iv) a V$_H$ CDR1 comprising an amino acid sequence of SEQ ID NO:36; (v) a V$_H$ CDR2 comprising an amino acid sequence of SEQ ID NO:37; and (vi) a V$_H$ CDR3 comprising an amino acid sequence of SEQ ID NO:38. In some cases, the antibody comprises: i) a V$_L$ CDR1 comprising an amino acid sequence of SEQ ID NO:33; (ii) a V$_L$ CDR2 comprising an amino acid sequence of SEQ ID NO:34; and (iii) a V$_L$ CDR3 comprising an amino acid sequence of SEQ ID NO:35. In some cases, the antibody comprises: (iv) a V$_H$ CDR1 comprising an amino acid sequence of SEQ ID NO:36; (v) a V$_H$ CDR2 comprising an amino acid sequence of SEQ ID NO:37; and (vi) a V$_H$ CDR3 comprising an amino acid sequence of SEQ ID NO:38. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKT-PPAPK (SEQ ID NO:78).

20) An isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:33; (ii) a $V_L$ CDR2 comprising an amino acid sequence of SEQ ID NO:34; and (iii) a $V_L$ CDR3 comprising an amino acid sequence of SEQ ID NO:35; and b) a heavy chain region comprising: (i) a $V_H$ CDR1 comprising an amino acid sequence of SEQ ID NO:36; (ii) a $V_H$ CDR2 comprising an amino acid sequence of SEQ ID NO:37; and (iii) a $V_H$ CDR3 comprising an amino acid sequence of SEQ ID NO:38. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some instances, the antibody binds an eTau1 polypeptide, an eTau2 polypeptide, and an eTau3 polypeptide, and does not bind an eTau4 polypeptide. In some cases, the antibody binds an epitope within the amino acid sequence RIPAKTPPAPK (SEQ ID NO:78).

21) An isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:47 and heavy chain CDRs of an antibody heavy chain variable region comprising amino acid sequence SEQ ID NO:48. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

22) An isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:47; an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:48; or an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:47 and heavy chain CDRs of an antibody heavy chain variable region comprising amino acid sequence SEQ ID NO:48. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

23) An isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:41; (ii) a $V_L$ CDR2 comprising an amino acid sequence of SEQ ID NO:42; and (iii) a $V_L$ CDR3 comprising an amino acid sequence of SEQ ID NO:43; and b) a heavy chain region comprising: (i) a $V_H$ CDR1 comprising an amino acid sequence of SEQ ID NO:44; (ii) a $V_H$ CDR2 comprising an amino acid sequence of SEQ ID NO:45; and (iii) a $V_H$ CDR3 comprising an amino acid sequence of SEQ ID NO:46. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

24) An isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:41; (ii) a $V_L$ CDR2 comprising an amino acid sequence of SEQ ID NO:42; (iii) a $V_L$ CDR3 comprising an amino acid sequence of SEQ ID NO:43; (iv) a $V_H$ CDR1 comprising an amino acid sequence of SEQ ID NO:44; (v) a $V_H$ CDR2 comprising an amino acid sequence of SEQ ID NO:45; and (vi) a $V_H$ CDR3 comprising an amino acid sequence of SEQ ID NO:46. In some cases, the antibody comprises: i) a $V_L$ CDR1 comprising an amino acid sequence of SEQ ID NO:41; (ii) a $V_L$ CDR2 comprising an amino acid sequence of SEQ ID NO:42; and (iii) a $V_L$ CDR3 comprising an amino acid sequence of SEQ ID NO:43. In some cases, the antibody comprises: (iv) a $V_H$ CDR1 comprising an amino acid sequence of SEQ ID NO:44; (v) a $V_H$ CDR2 comprising an amino acid sequence of SEQ ID NO:45; and (vi) a $V_H$ CDR3 comprising an amino acid sequence of SEQ ID NO:46. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

25) An isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:41; (ii) a $V_L$ CDR2 comprising an amino acid sequence of SEQ ID NO:42; and (iii) a $V_L$ CDR3 comprising an amino acid sequence of SEQ ID NO:43; and b) a heavy chain region comprising: (i) a $V_H$ CDR1 comprising an amino acid sequence of SEQ ID NO:44; (ii) a $V_H$ CDR2 comprising an amino acid sequence of SEQ ID NO:45; and (iii) a $V_H$ CDR3 comprising an amino acid sequence of SEQ ID NO:46. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, and does not bind an eTau1 polypeptide, an eTau2 polypeptide, or an eTau3 polypeptide. In some instances, the antibody binds an epitope within the amino acid sequence EDEAAGHVTQAR (SEQ ID NO:79). In some cases, the antibody binds a neoepitope in an eTau4 polypeptide.

26) An isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:55 and heavy chain CDRs of an antibody heavy chain variable region comprising amino acid sequence SEQ ID NO:56. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

27) An isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:55; an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:56; or an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:55 and heavy chain CDRs of an antibody heavy chain variable region comprising amino acid sequence SEQ ID NO:56. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

28) An isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:49; (ii) a $V_L$ CDR2 comprising an amino acid sequence of SEQ ID NO:50; and (iii) a $V_L$ CDR3 comprising an amino acid sequence of SEQ ID NO:51; and b) a heavy chain region comprising: (i) a $V_H$ CDR1 comprising an amino acid sequence of SEQ ID NO:52; (ii) a $V_H$ CDR2 comprising an amino acid sequence of SEQ ID NO:53 and (iii) a $V_H$ CDR3 comprising an amino acid sequence of SEQ ID NO:54. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

29) An isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:49; (ii) a $V_L$ CDR2 comprising an amino acid sequence of SEQ ID NO:50; (iii) a $V_L$ CDR3 comprising an amino acid sequence of SEQ ID NO:51; (iv) a $V_H$ CDR1 comprising an amino acid sequence of SEQ ID NO:52; (v) a $V_H$ CDR2 comprising an amino acid sequence of SEQ ID NO:53; and (vi) a $V_H$ CDR3 comprising an amino acid sequence of SEQ ID NO:54. In some cases, the antibody comprises: i) a $V_L$ CDR1 comprising an amino acid sequence of SEQ ID NO:49; (ii) a $V_L$ CDR2 comprising an amino acid sequence of SEQ ID NO:50; and (iii) a $V_L$ CDR3 comprising an amino acid sequence of SEQ ID NO:51. In some cases, the antibody comprises: (iv) a $V_H$ CDR1 comprising an amino acid sequence of SEQ ID NO:52; (v) a $V_H$ CDR2 comprising an amino acid sequence of SEQ ID NO:53; and (vi) a $V_H$ CDR3 comprising an amino acid sequence of SEQ ID NO:54. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

30) An isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:49; (ii) a $V_L$ CDR2 comprising an amino acid sequence of SEQ ID NO:50; and (iii) a $V_L$ CDR3 comprising an amino acid sequence of SEQ ID NO:51; and b) a heavy chain region comprising: (i) a $V_H$ CDR1 comprising an amino acid sequence of SEQ ID NO:52; (ii) a $V_H$ CDR2 comprising an amino acid sequence of SEQ ID NO:53; and (iii) a $V_H$ CDR3 comprising an amino acid sequence of SEQ ID NO:54. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

31) An isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:63 and heavy chain CDRs of an antibody heavy chain variable region comprising amino acid sequence SEQ ID NO:64. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

32) An isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:63; an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:64; or an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:63 and heavy chain CDRs of an antibody heavy chain variable region comprising amino acid sequence SEQ ID NO:64. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

33) An isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:57; (ii) a $V_L$ CDR2 comprising an amino acid sequence of SEQ ID NO:58; and (iii) a $V_L$ CDR3 comprising an amino acid sequence of SEQ ID NO:59; and b) a heavy chain region comprising: (i) a $V_H$ CDR1 comprising an amino acid sequence of SEQ ID NO:60; (ii) a $V_H$ CDR2 comprising an amino acid sequence of SEQ ID NO:61; and (iii) a $V_H$ CDR3 comprising an amino acid sequence of SEQ ID NO:62. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

34) An isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:57; (ii) a $V_L$ CDR2 comprising an amino acid sequence of SEQ ID NO:58; (iii) a $V_L$ CDR3 comprising an amino acid sequence of SEQ ID NO:59; (iv) a $V_H$ CDR1 comprising an amino acid sequence of SEQ ID NO:60; (v) a $V_H$ CDR2 comprising an amino acid sequence of SEQ ID NO:61; and (vi) a $V_H$ CDR3 comprising an amino acid sequence of SEQ ID NO:62. In some cases, the antibody comprises: i) a $V_L$ CDR1 comprising an amino acid sequence of SEQ ID NO:57; (ii) a $V_L$ CDR2 comprising an amino acid sequence of SEQ ID NO:58; and (iii) a $V_L$ CDR3 comprising an amino acid sequence of SEQ ID NO:59. In some cases, the antibody comprises: (iv) a $V_H$ CDR1 comprising an amino acid sequence of SEQ ID NO:60; (v) a $V_H$ CDR2 comprising an amino acid sequence of SEQ ID NO:61; and (vi) a $V_H$ CDR3 comprising an amino acid sequence of SEQ ID NO:62. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

35) An isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:57; (ii) a $V_L$ CDR2 comprising an amino acid sequence of SEQ ID NO:58; and (iii) a $V_L$ CDR3 comprising an amino acid sequence of SEQ ID NO:59; and b) a heavy chain region comprising: (i) a $V_H$ CDR1 comprising an amino acid sequence of SEQ ID NO:60; (ii) a $V_H$ CDR2 comprising an amino acid sequence of SEQ ID NO:61; and (iii) a $V_H$ CDR3 comprising an amino acid sequence of SEQ ID NO:62. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau4 polypeptide, an eTau1 polypeptide, an eTau2 polypeptide, and an eTau3 polypeptide. In some instances, the antibody binds an epitope within the amino acid sequence EDEAAGHVTQAR (SEQ ID NO:79).

36) An isolated antibody that binds an epitope in a Tau polypeptide (e.g., an eTau polypeptide of the present disclosure) wherein the antibody competes for binding the epitope with an antibody that comprises light chain CDRs of an antibody light chain variable region comprising amino acid sequence SEQ ID NO:71 and heavy chain CDRs of an antibody heavy chain variable region comprising amino acid sequence SEQ ID NO:72. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

37) An isolated antibody that binds an epitope in a Tau polypeptide (e.g., an eTau polypeptide of the present disclosure) wherein the antibody comprises a light chain comprising light chain CDRs of an antibody light chain variable region comprising amino acid sequence SEQ ID NO:71; an isolated antibody that binds an epitope in a Tau polypeptide (e.g., an eTau polypeptide of the present disclosure) wherein the antibody comprises a heavy chain comprising heavy chain CDRs of an antibody heavy chain variable region comprising the amino acid sequence SEQ ID NO:72; or an isolated antibody that binds an epitope in a Tau polypeptide (e.g., an eTau polypeptide of the present disclosure) wherein the antibody comprises light chain CDRs of an antibody light chain variable region comprising amino acid sequence SEQ ID NO:71 and heavy chain CDRs of an antibody heavy chain variable region comprising amino acid sequence SEQ ID NO:72. In some cases, the antibody is humanized. For example, in some cases, a humanized light chain framework region. In some instances, the antibody comprises a humanized heavy chain framework region. In some cases, the antibody comprises a humanized light chain framework region and a humanized heavy chain framework region. In some cases, the antibody comprises a heavy chain constant region of the isotype IgG1, IgG2, IgG3, or IgG4. In some cases, the antibody is an antibody fragment, e.g., a Fab fragment, a F(ab')$_2$ fragment, a scFv, or a Fv. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

38) An isolated antibody that competes for binding to an epitope in a Tau polypeptide (e.g., an eTau polypeptide of the present disclosure) with an antibody that comprises: a) a light chain region comprising: i) a $V_L$ CDR1 comprising an amino acid sequence of SEQ ID NO:65; (ii) a $V_L$ CDR2 comprising an amino acid sequence of SEQ ID NO:66; and (iii) a $V_L$ CDR3 comprising an amino acid sequence of SEQ ID NO:67; and b) a heavy chain region comprising: (i) a $V_H$ CDR1 comprising an amino acid sequence of SEQ ID NO:68; (ii) a $V_H$ CDR2 comprising an amino acid sequence of SEQ ID NO:69; and (iii) a $V_H$ CDR3 comprising an amino acid sequence of SEQ ID NO:70. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

39) An isolated monoclonal antibody that specifically binds a Tau polypeptide (e.g., an eTau polypeptide of the present disclosure), wherein the isolated antibody comprises 1, 2, 3, 4, 5, or 6 of the following CDRs: i) a $V_L$ CDR1 comprising an amino acid sequence of SEQ ID NO:65; (ii) a $V_L$ CDR2 comprising an amino acid sequence of SEQ ID NO:66; (iii) a $V_L$ CDR3 comprising an amino acid sequence of SEQ ID NO:67; (iv) a $V_H$ CDR1 comprising an amino acid sequence of SEQ ID NO:68; (v) a $V_H$ CDR2 comprising an amino acid sequence of SEQ ID NO:69; and (vi) a $V_H$ CDR3 comprising an amino acid sequence of SEQ ID NO:70. In some cases, the antibody comprises: i) a $V_L$ CDR1 comprising an amino acid sequence of SEQ ID NO:65; (ii) a $V_L$ CDR2 comprising an amino acid sequence of SEQ ID NO:66; and (iii) a $V_L$ CDR3 comprising an amino acid sequence of SEQ ID NO:67. In some cases, the antibody comprises: (iv) a $V_H$ CDR1 comprising an amino acid sequence of SEQ ID NO:68; (v) a $V_H$ CDR2 comprising an amino acid sequence of SEQ ID NO:69; and (vi) a $V_H$ CDR3 comprising an amino acid sequence of SEQ ID NO:70. In some cases, the antibody is humanized. For example, in some cases, the antibody comprises a humanized light chain framework region. In some instances, the antibody comprises a humanized heavy chain framework region. In some cases, the antibody comprises a humanized light chain framework region and a humanized heavy chain framework region. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

40) An isolated humanized monoclonal antibody comprising a humanized light chain framework region; and a humanized heavy chain framework region, wherein the isolated antibody specifically binds a Tau polypeptide (e.g., an eTau polypeptide of the present disclosure), and wherein the isolated antibody comprises: a) a light chain region comprising: i) a $V_L$ CDR1 comprising an amino acid sequence of SEQ ID NO:65; (ii) a $V_L$ CDR2 comprising an amino acid sequence of SEQ ID NO:66; and (iii) a $V_L$ CDR3 comprising an amino acid sequence of SEQ ID NO:67; and b) a heavy chain region comprising: (i) a $V_H$ CDR1 comprising an amino acid sequence of SEQ ID NO:68; (ii) a $V_H$ CDR2 comprising an amino acid sequence of SEQ ID NO:69; and (iii) a $V_H$ CDR3 comprising an amino acid sequence of SEQ ID NO:70. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the isolated antibody binds a Tau polypeptide with a dissociation constant ($K_D$) of $10^{-7}$ M, $10^{-8}$ M, $10^{-9}$ M, $10^{-10}$ M, or $10^{-11}$ M. In some cases, the antibody binds an eTau2 polypeptide, an eTau1 polypeptide, an eTau3 polypeptide, and an eTau4 polypeptide. In some cases, the antibody binds an eTau2 polypeptide, and an eTau1 polypeptide, but does not bind an eTau3 polypeptide or an eTau4 polypeptide. In some instances, the antibody binds an epitope within the amino acid sequence SSPGSPGTPGSR (SEQ ID NO:80).

A tauopathy is a disorder characterized by an abnormal level of tau in a tissue or fluid in an individual. In some cases, a tauopathy is characterized by the presence in a tissue or a fluid of elevated (higher than normal) levels of tau or tau peptides and/or pathological forms of tau. For example, in some cases, a tauopathy is characterized by the presence in brain tissue and/or cerebrospinal fluid of elevated levels of tau or tau peptides and/or pathological forms of tau. A "higher than normal" level of tau in a tissue or a fluid indicates that the level of tau in the tissue or fluid is higher than a normal, control level, e.g., higher than a normal, control level for an individual or population of individuals of the same age group. See, e.g., Blomberg et al. (2001) "Cerebrospinal fluid tau levels increase with age in healthy individuals" *Dement. Geriatr. Cogn. Disord.* 12:127. In some cases, an individual having a tauopathy exhibits one or more additional symptoms of a tauopathy (e.g., cognitive decline).

In other cases, a tauopathy is characterized by the presence in a tissue or a fluid of lower than normal levels of tau. A "lower than normal" level of tau in a tissue or a fluid indicates that the level of tau in the tissue or fluid is lower than a normal, control level, e.g., lower than a normal, control level for an individual or population of individuals of the same age group.

Alzheimer's disease and certain forms of Frontotemporal dementia (Pick's disease, sporadic Frontotemporal dementia and Frontotemporal dementia with Parkinsonism linked to chromosome 17) are the most common forms of tauopathy. In accordance, the present invention relates to any method as described above, wherein the tauopathy is Alzheimer's, Pick's disease, sporadic Frontotemporal dementia and Frontotemporal dementia with Parkinsonism linked to chromosome 17. Other tauopathies include but are not limited to Progressive supranuclear palsy (PSP), Corticobasal degeneration (CBD) and Subacute sclerosing panencephalitis.

A neurodegenerative tauopathy includes Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, ischemic stroke, chronic traumatic encephalopathy (CTE), traumatic brain injury (TBI), and stroke.

The present disclosure also provides methods of treating a synucleinopathy, e.g., Parkinson's disease (PD); dementia with Lewy Bodies (DLB); multiple system atrophy (MSA); etc. For example, PD with dementia (PDD) can be treated with a subject method.

In one embodiment, an anti-tau antibody of the present disclosure prevents or delays the onset of at least one symptom of a neurodegenerative tauopathy in a subject. In one embodiment, a subject anti-tau antibody reduces or eliminates at least one symptom of a neurodegenerative tauopathy in a subject. The symptom may be the formation of one or more of pathological tau deposits; extracellular soluble Tau and/or Tau fragments; hyperphosphorylated tau deposits; insoluble tau deposits; neurofibrillary tangles; neurofibrillary fibers; pre-tangle phospho-tau aggregates; intraneuronal neurofibrillary tangles; neuronal hyperactivity; and extraneuronal neurofibrillary tangles in the brain or spinal cord of a subject. The symptom may be a neurological symptom, for example, impaired cognitive function, memory impairment, loss of motor function, etc. In some cases, an anti-tau antibody of the present disclosure can improve cognitive function. In some cases, an anti-tau antibody of the present disclosure can reduce the rate of decline in cognitive function. In some cases, an anti-tau antibody of the present disclosure can improve motor function. In some cases, an anti-tau antibody of the present disclosure can reduce the rate of decline in motor function.

The symptom can also be the level of a subject tau peptide in the CSF of the individual. For example, in some embodiments, a subject anti-tau antibody, when administered in one or more doses as monotherapy or in combination therapy to an individual having a tauopathy, reduces the level of a tau peptide of the present disclosure in the CSF of the individual by at least about 10%, at least about 15%, at least about 20%, at least about 25%, at least about 30%, at least about 40%, at least about 50%, or more than 50%, compared to the level of the tau peptide in the CSF of the individual before treatment with the anti-tau antibody.

Administration of a subject anti-tau antibody to an individual can result in one or more of: reduction in the amount of free extracellular Tau in brain tissue; reduction in the cell-to-cell spread (e.g., neuron-to-neuron spread) of Tau (e.g., Tau fragments); reduction in the amount of tau aggregates (e.g., intracellular (e.g., intraneuronal) tau aggregates); reduction in the amount of neurofibrillary tangles in brain tissue; reduction in the level of microglial activation and/or astrocyte activation; reduction in the amount of phosphorylated tau; reduction in the amount of hyperphosphorylated tau; reduction in total Tau (e.g., total intracellular Tau; and/or total extracellular Tau); reduction in free Tau (e.g., Tau that is not bound to a subject anti-Tau antibody); reduction in neuronal hyperactivity; and reduction in the amount of N-terminal Tau fragments. "Total Tau" can include the sum total of full-length Tau of any isoform; and any N-terminal Tau fragments that are present and that display the epitope recognized by a subject anti-Tau antibody. Reduction in phosphorylated Tau can be determined using any known method, e.g., an immunological method using an anti-phospho-Tau antibody.

In some cases, administration of a subject anti-Tau antibody results in a change in one or more of: a) the amount of free extracellular tau in brain tissue; b) the amount of free extracellular tau in interstitial fluid (ISF); c) the amount of free extracellular tau in cerebrospinal fluid (CSF); d) the neuron-to-neuron spread of tau; e) the amount of intraneuron tau aggregates; f) the degree of microglial and/or astrocyte activation; g) the amount of phosphorylated or hyperphosphorylated tau; h) the amount of total Tau or free tau in ISF or CSF; i) the amount of intracellular N-terminal tau fragments; j) neuronal hyperactivity; k) the amount of Aβ40 and/or Aβ42 in CSF; l) the Aβ plaque burden; m) secretion of Aβ40 and/or Aβ42 from a neuron; n) amyloid precursor protein (APP) promoter activity; o) APP mRNA and/or protein level; p) the activity of beta-secretase and/or gamma secretase; q) the activation state of an Aβ induced signaling pathway; r) the amount of intracellular total tau or free tau; s) the amount of anti-tau antibody-bound tau in ISF or CSF; and t) the amount of intracellular anti-Tau antibody-bound tau.

Administration of a subject anti-tau antibody to an individual can result in one or more of: reduction in the amount of free extracellular tau peptide in brain tissue; reduction in the cell-to-cell spread (e.g., neuron-to-neuron spread) of tau peptides; reduction in the amount of tau aggregates (e.g., intracellular (e.g., intraneuronal) tau aggregates); and reduction in the amount of neurofibrillary tangles in brain tissue. Administration of a subject anti-tau antibody to an individual can in some cases improve cognitive function in the individual, or at least reduce the rate of decline of cognitive function in the individual.

In some cases, administration of a subject anti-tau antibody to an individual reduces the amount of free extracellular tau peptide (e.g., the amount of free extracellular tau peptide in a brain tissue) by at least about 10%, at least about 20%, at least about 25%, at least about 50%, or more than 50%, compared to the amount of free extracellular tau peptide in the individual before administration with the anti-tau antibody.

In some cases, administration of a subject anti-tau antibody to an individual reduces the cell-to-cell (e.g., neuron-to-neuron) spread of a tau peptide (e.g., a pathological tau peptide) by at least about 10%, at least about 20%, at least about 25%, at least about 50%, or more than 50%, compared to the cell-to-cell spread before administration with a subject anti-tau antibody.

In some cases, administration of a subject anti-tau antibody to an individual reduces the amount of tau aggregates (e.g., intracellular (e.g., intraneuronal) tau aggregates) by at least about 10%, at least about 20%, at least about 25%, at least about 50%, or more than 50%, compared to the amount of tau aggregates before administration with the anti-tau antibody.

In some cases, administration of a subject anti-tau antibody to an individual reduces neurotoxicity in an individual; and/or reduces neuroinflammation in an individual; and/or reduces activation of astrocytes and microglia; and/or reduces induction of pathological electrophysiological effects; and/or reduces the amount of tau in exosomes.

In some cases, an antibody for use in a method disclosed herein is other than a Tau12 antibody, a Tau13 antibody, a TNT1 antibody, a 5A6 antibody, an HJ9.4 antibody, an HT7 antibody, or a 6C10 antibody.

An anti-tau antibody of the present disclosure can be present in a pharmaceutical composition. Thus, the present disclosure provides a pharmaceutical composition comprising: a) an anti-tau antibody of the present disclosure; and b) a pharmaceutically acceptable carrier. A subject anti-tau antibody can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose.

Administration of the suitable compositions may be effected by different ways, e.g., by intravenous, intrathecal, intraperitoneal, subcutaneous, intracranial, intraarterial (e.g., via the carotid artery), intramuscular, intranasal, topical or intradermal administration or spinal or brain delivery. Aerosol formulations such as nasal spray formulations include purified aqueous or other solutions of the active agent with preservative agents and isotonic agents. Such formulations are adjusted to a pH and isotonic state compatible with the nasal mucous membranes.

In some cases, a subject anti-tau antibody is modified, or formulated, in such a manner as to provide the ability of the antibody to cross the blood-brain barrier. Such an antibody or antibody composition can be administered to an individual having a tauopathy by various enteral and parenteral routes of administration including oral, intravenous, etc.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as dopamine or psychopharmacologic drugs, depending on the intended use of the pharmaceutical composition.

The dosage regimen will be determined by the attending physician or other medical personnel, based on various clinical factors. As is well known in the medical arts, dosages for any one patient depends upon various factors, including the patient's size, body surface area, age, the particular compound to be administered, sex, time and route of administration, general health, and other drugs being administered concurrently. A dose of a subject anti-tau antibody can be, for example, in the range of 0.001 µg to 1000 µg; however, doses below or above this exemplary range are envisioned, especially considering the aforementioned factors. Generally, the dosage can range, e.g., from about 0.0001 to 100 mg/kg, or from about 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment.

Combination Therapy

An anti-tau antibody of the present disclosure can be administered to an individual in need thereof alone (e.g., as monotherapy); or in combination therapy with one or more additional therapeutic agents.

For the treatment of AD, suitable additional therapeutic agents include, but are not limited to, acetylcholinesterase inhibitors, including, but not limited to, Aricept (donepezil), Exelon (rivastigmine), metrifonate, and tacrine (Cognex); an anti-Aβ antibody; non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art.

Another suitable additional therapeutic agent in the treatment of AD is an agent that inhibits tau aggregation, e.g., a napthoquinone derivative that inhibits tau aggregation, as described in U.S. Pat. No. 7,605,179. Another suitable additional therapeutic agent is an agent that inhibits phosphorylation of tau, e.g., a 3-substituted-4-pyrimidone derivative that inhibits tau protein kinase 1, as described in U.S. Pat. No. 7,572,793.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

Individuals to be Treated

Individuals suitable for treatment with a subject anti-tau antibody include individuals who have been diagnosed as having a tauopathy; individuals at greater risk than the general population for developing a tauopathy (e.g., individuals having a genetic predisposition to developing a tauopathy); and the like. In some cases, the individual is an adult human. In some cases, the adult human is 40 years of age or older, 50 years of age or older, 60 years of age or older, 70 years of age or older, or 80 years of age or older. For example, the adult human can be from 40 years old to 50 years old, from 50 years old to 60 years old, from 60 years old to 70 years old, or older than 70 years.

Detection Methods

The present disclosure provides methods of detecting an extracellular Tau (eTau) polypeptide (e.g., a Tau polypeptide of the present disclosure) in a biological sample obtained from an individual; and methods of detecting a tau peptide in a living individual in vivo. A detection method of the present disclosure can be used to determine whether an individual has, or is at risk of developing, a tauopathy. A detection method of the present disclosure can be used to determine the stage (severity) of a tauopathy. A detection method of the present disclosure can be used to determine a patient's response to a treatment regimen for treating a tauopathy. A biological sample can be tested using a subject detection method, where the biological sample is obtained from an individual suspected of having a tauopathy, an individual who has been diagnosed as having a tauopathy, an individual who has a genetic predisposition to developing a tauopathy, etc.

The present disclosure provides a method of diagnosing a neurodegenerative tauopathy in an individual. The method generally involves (a) assessing the level of an eTau polypeptide in a biological sample obtained from the individual; and (b) comparing the level of the eTau polypeptide to a reference, a standard, or a normal control value that indicates the level of the pathologically modified or aggregated tau in one or more control subjects. A difference or similarity between the level of pathologically modified or aggregated tau and the normal control value indicates that the individual has a neurodegenerative tauopathy.

The present disclosure provides a method of monitoring the progression of, or monitoring response to treatment for, a neurodegenerative tauopathy in an individual. The method generally involves comparing the level of an eTau polypeptide in a biological sample obtained from the individual at a first time point with the level of an eTau polypeptide in a biological sample obtained from the individual at a second time point. A difference in the level of the eTau polypeptide in a biological sample obtained from the individual at a second time point, compared to the level of the eTau polypeptide in a biological sample obtained from the individual at a first time point, can provide an indication as to: i) whether the tauopathy is progressing or whether progression of the disease has halted; and/or ii) how quickly the tauopathy is progressing; and/or iii) whether the individual is exhibiting a beneficial clinical response to treatment with a drug or other treatment regimen for treating the tauopathy.

The present disclosure provides a method of staging a tauopathy. For example, a subject method can provide for staging Alzheimer's disease. For example, the level of an eTau polypeptide in a biological sample (e.g., the CSF or other liquid biological sample) from a living individual can provide an indication as to the Braak stage of AD. Braak and Braak (1995) *Neurobiol. Aging* 16:271. For example, the level of a subject tau peptide in a biological sample from a living individual can provide an indication as to whether the individual is in transentorhinal stages I-II of AD; limbic stages III-IV of AD; or neocortical stages V-VI of AD.

The level of an eTau polypeptide in a biological sample can be assessed by any suitable method known in the art. Suitable methods include, but are not limited to, a protein ("Western") blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry.

In Vivo Imaging

As discussed above, the present disclosure provides methods of detecting an eTau polypeptide in a living individual, e.g., by an in vivo imaging technique. For example, in one embodiment, in vivo imaging of an eTau polypeptide can be accomplished by positron emission tomography (PET), single photon emission tomography (SPECT), near infrared (NIR) optical imaging, or magnetic resonance imaging (MRI). A subject anti-tau antibody is administered to an individual, and the presence and/or level of the tau peptide is detected. The anti-tau antibody can comprise a label suitable for use in PET, SPECT, NIR, or MRI. Such labels include a contrast agent or a radioisotope, where the contrast agent or radioisotope is one that is suitable for use in imaging, e.g., imaging procedures carried out on humans, as described above.

Generating a Report

In some instances, a subject detection method comprises detecting an eTau polypeptide in a biological sample obtained from an individual; and, based on the level of detected tau, generating a report and/or directing therapy or management of the individual from whom the biological sample was obtained.

A report can include one or more of: an indication as to whether the individual likely has a tauopathy; an indication of the severity of the tauopathy; an indication as to whether the individual exhibits a beneficial clinical response to treatment for the tauopathy; and the like.

Thus, a report can include information such as a predicted likelihood that the individual has, or will develop, a tauopathy; a recommendation regarding further evaluation; a recommendation regarding therapeutic drug and/or other health management intervention; and the like.

For example, the methods disclosed herein can further include a step of generating or outputting a report providing the results of a subject assessment, which report can be provided in the form of an electronic medium (e.g., an electronic display on a computer monitor), or in the form of a tangible medium (e.g., a report printed on paper or other tangible medium). An assessment as to the likelihood that a person has, or at risk of developing, a tauopathy can be referred to as a "risk report," "a risk score," or "a likelihood score." A person or entity that prepares a report ("report generator") may also perform steps such as sample gathering, sample processing, and the like. Alternatively, an entity other than the report generator can perform steps such as sample gathering, sample processing, and the like. A risk assessment report can be provided to a user. A "user" can be a health professional (e.g., a clinician, a laboratory technician, or a physician).

Directing Health Management

In some instances, a subject detection method comprises detecting an eTau polypeptide in a biological sample obtained from an individual; and, based on the level of detected tau, generating a report and/or directing therapy or management of the individual from whom the biological sample was obtained.

Thus, e.g., depending on the outcome of a subject detection method, a recommendation can be made that the individual undergo therapeutic intervention (treatment) for the tauopathy and/or that the individual be considered for special health management.

Therapeutic intervention can include, e.g., drug therapy for the treatment of Alzheimer's disease. Examples of drug therapy for the treatment of Alzheimer's disease include, but are not limited to, acetylcholinesterase inhibitors, including, but not limited to, Aricept (donepezil), Exelon (rivastigmine), metrifonate, and tacrine (Cognex); an anti-Aβ antibody (e.g., bapineuzumab; solanezumab); an anti-tau antibody; non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept can be administered at 50 mg orally per day for 6 weeks, and, if well tolerated by the individual, at 10 mg per day thereafter.

Kits and Assay Devices

The present disclosure provides kits and assay devices for carrying out a diagnostic method as described herein.

Kits

The present disclosure provides a kit for carrying out a diagnostic method as described herein. In some cases, a subject kit includes an anti-tau antibody of the present disclosure. In other cases, a subject kit includes a tau peptide of the present disclosure.

Kits Comprising an Anti-Tau Antibody

In some cases, a subject kit includes an anti-tau antibody of the present disclosure. The anti-tau antibody can be immobilized on an insoluble support (e.g., a test strip, a well of a multi-well plate, a bead (e.g., a magnetic bead), etc.), as described above.

An anti-tau antibody can comprise a detectable label. Where the antibody comprises a detectable label, a subject kit can include one or more reagents for developing the detectable label. A labeled antibody can comprise a label such as a chemiluminescent agent, a particulate label, a colorimetric agent, an energy transfer agent, an enzyme, a fluorescent agent, or a radioisotope. Suitable detectable labels include any composition detectable by spectroscopic, photochemical, biochemical, immunochemical, electrical, optical, or chemical means. Suitable detectable labels include, but are not limited to, fluorescent labels (e.g., fluorescein isothiocyanate, texas red, rhodamine, a green fluorescent protein, a red fluorescent protein, a yellow fluorescent protein, and the like); radiolabels (e.g., $^3H$, $^{125}I$, $^{35}S$, $^{14}C$ or $^{32}P$); and enzymes (e.g., horse radish peroxidase, alkaline phosphatase, luciferase, and other enzymes that act on a substrate to produce a product that can be detected by fluorometric, colorimetric, or spectrophotometric means).

In some embodiments, a subject kit includes a purified tau peptide of the present disclosure, which purified tau peptide can be used as a positive control, where the tau peptide is of greater than 90% purity, greater than 95% purity, greater than 98% purity, or greater than 99% purity. The standard tau peptide can be prepared synthetically, can be isolated from a cell that produces the tau peptide, or can be isolated from the culture medium of a cell culture comprising a cell that produces the tau peptide. In some cases, the standard tau peptide is prepared synthetically, e.g., using standard chemical methods for peptide synthesis. In some cases, the purified tau peptides are suitable for generating a standard curve, e.g., for quantitating a tau peptide detected in a test biological sample from a test individual. Examples of amounts of tau peptide suitable for generating a standard curve include, e.g., 0.5 µg, 1.0 µg, 1.5 µg, 2.0 µg, and 5.0 µg.

Kits Comprising a Tau Peptide

In other cases, a subject kit includes a tau peptide of the present disclosure. Such a kit can be used to detect the presence of an antibody that specifically binds a tau peptide of the kit. In some cases, the tau peptide is of greater than 90% purity, greater than 95% purity, greater than 98% purity, or greater than 99% purity.

A tau peptide present in the kit can include a detectable label. Suitable detectable labels include any moiety detectable by spectroscopic, photochemical, biochemical, immunochemical, electrical, optical or chemical means. Suitable detectable labels include, but are not limited to, magnetic beads (e.g. Dynabeads™); fluorescent proteins (e.g., a green fluorescent protein, a red fluorescent protein, a yellow fluorescent protein, and the like); fluorescent dyes (e.g., fluorescein isothiocyanate, texas red, rhodamine or a rhodamine derivative (e.g., rhodamine B; TAMRA), 7-Amino-4-methyl-coumarin (AMC), 5-((2-Aminoethyl)amino) napthalene-1-sulfonic acid (EDANS), 7-Nitrobenz-2-oxa-1, 3-diazole (NBD), etc.); a fluorescence quencher (e.g., Dabcyl, Dansyl, 2,4-Dinitrophenol, etc.); p-Nitroaniline; radiolabels (e.g., $^3H$, $^{125}I$, $^{35}S$, $^{14}C$, $^{14}N$, $^{13}C$, $^{15}N$, or $^{32}P$); enzymes (e.g., horse radish peroxidase, alkaline phosphatase, luciferase, and others commonly used in an enzyme-linked immunosorbent assay (ELISA)); colorimetric labels such as colloidal gold or colored glass or plastic (e.g. polystyrene, polypropylene, latex, etc.) beads; and the like.

A tau peptide present in the kit can be attached, directly or via a linker, to a solid support. Suitable supports are well known in the art and include, inter alia, commercially available column materials, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject tau peptide onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

Additional Components

The various components of the kit may be present in separate containers or certain compatible components may be pre-combined into a single container, as desired. A subject kit can further include one or more additional components, where suitable additional components include: 1) a positive control; 2) a buffer (e.g., a binding buffer; a wash buffer; etc.); 3) reagents for use in generating a detectable signal; and the like. Other optional components of the kit include: a protease inhibitor; a detectable label; etc.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Assay Devices

The present disclosure provides assay devices for carrying out a subject diagnostic method. An assay device of the present disclosure can be used for detecting, in a liquid biological sample obtained from an individual, a tau peptide as described herein.

A subject device can include a matrix defining an axial flow path. The matrix can comprise: i) a sample receiving zone at an upstream end of the flow path that receives the liquid sample. The matrix can further comprise: ii) one or more test zones positioned within the flow path and downstream from the sample receiving zone, each of the one or more test zones comprising an antibody specific for a subject tau peptide in each of the test zones, where each of the immobilized antibodies is capable of binding a different tau peptide present in the liquid sample, to form an immobilized tau peptide. The matrix can further comprise: iii) one or more control zones positioned within the flow path and downstream from the sample receiving zone, where the one or more control zones can include positive and/or negative controls. The test zones and control zones can be positioned in an alternating format within the flow path beginning with a test zone positioned upstream of any control zone. In some cases, the assay device has only one test zone positioned within the flow path and downstream from the sample receiving zone, where the one test zone comprises an antibody specific for a subject tau peptide.

In using such an assay device, in some embodiments, a labeled antibody specific for a subject tau peptide can first be mixed with a liquid sample before the liquid sample is applied to the sample receiving zone of the device, where such mixing results in a labeled antibody/tau peptide complex. In these embodiments, the liquid sample comprising the labeled antibody/tau peptide complex is applied to the sample receiving zone of the assay device. The liquid sample flows along the device until the liquid sample reaches a test zone. Antibody present in the test zone binds a tau peptide present in the labeled antibody/tau peptide complex; and can then be detected.

The assay device can further include a label zone comprising a labeled antibody specific for a tau peptide, where the labeled antibody is capable of binding a tau peptide present in an immobilized tau peptide complex, to form a labeled tau peptide complex, where the labeled antibody is mobilizable in the presence of liquid sample. In using such an assay device, a liquid sample comprising a tau peptide is applied to the sample receiving zone of the device; antibody present in the label zone binds the tau peptide, forming labeled antibody/tau peptide complex, which, like the labeled antibody, is mobilizable; and the labeled antibody/tau peptide complex flows alone the device until the liquid sample reaches a test zone. Antibody present in the test zone binds a tau peptide present in the labeled antibody/tau peptide complex; and can then be detected.

The labeled antibody can comprise a label such as a chemiluminescent agent, a particulate label, a colorimetric agent, an energy transfer agent, an enzyme, a fluorescent agent, or a radioisotope. Suitable labels are described above.

Control zones include positive control zones and negative control zones.

The matrix is generally an insoluble support, where suitable insoluble supports include, but are not limited to, polyvinyl difluoride (PVDF), cellulose, nitrocellulose, nylon, and the like. The matrix can be flexible, or can be relatively inflexible. The matrix can be positioned within a housing comprising a support and optionally a cover, where the housing contains an application aperture and one or more observation ports. The assay device can be in any of a variety of formats, e.g., a test strip, a dipstick; etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); kd or kDa, kiloDalton; Ab, antibody; and the like.

Example 1: Isolation and Characterization of Extracellular Tau Peptide

Extracellular tau ("eTau") forms were isolated from conditioned medium of cortical neurons derived from iPSC generated from an individual with Alzheimer's disease.

iPSC generated from fibroblasts from a skin punch of an AD patient were differentiated to cortical neurons and the conditioned media (CM) from these neurons was separated by sodium dodecyl sulfate-polyacrylamide gel electrophoresis (SDS-PAGE) and Western blotted with IPN002 and Tau H-150 antibodies.

FIG. 3 presents data showing the levels of eTau peptides in various samples. Multiple biological replicates of a healthy ("H") and a PSEN1 fAD (familial AD) line show more eTau present in the fAD line compared to the healthy line. These data have been quantitated for this and other experiments and lines, including multiple healthy lines, this fAD line and a Down's line (with APP duplication), and consistently show a range between 30% increase up to a 100% increase in eTau in fAD or Down's lines versus healthy lines. These increases are consistent with increased levels of tau present in AD CSF compared to healthy patient CSF.

These N-terminal eTau bands suggest tau cleavage products present in the conditioned media, and the protein sequence of these fragments has not previously been described. Thus, a process for isolating these eTau reactive proteins was developed; and the amino acid sequence of the fragments was determined. Conditioned media (1.6 liters pooled from sAD (sporadic AD) and fAD patient iPSC-derived cortical neuron cultures) were precleared on an IgG coupled Sepharose 4B resin and then affinity isolated on column where IPN001 antibody (tau amino acid reactivity #2-18) was coupled to Sepharose 4B resin. The flow through from the IPN001 resin was added to a Tau46 C-terminal antibody-coupled Sepharose 4B column and affinity isolated via elution with low pH glycine buffer. Eluates from both these columns were concentrated, and a small fraction tested on Western blots probed with IPN002 and Dako Tau (C-terminal tau).

Figure 4:
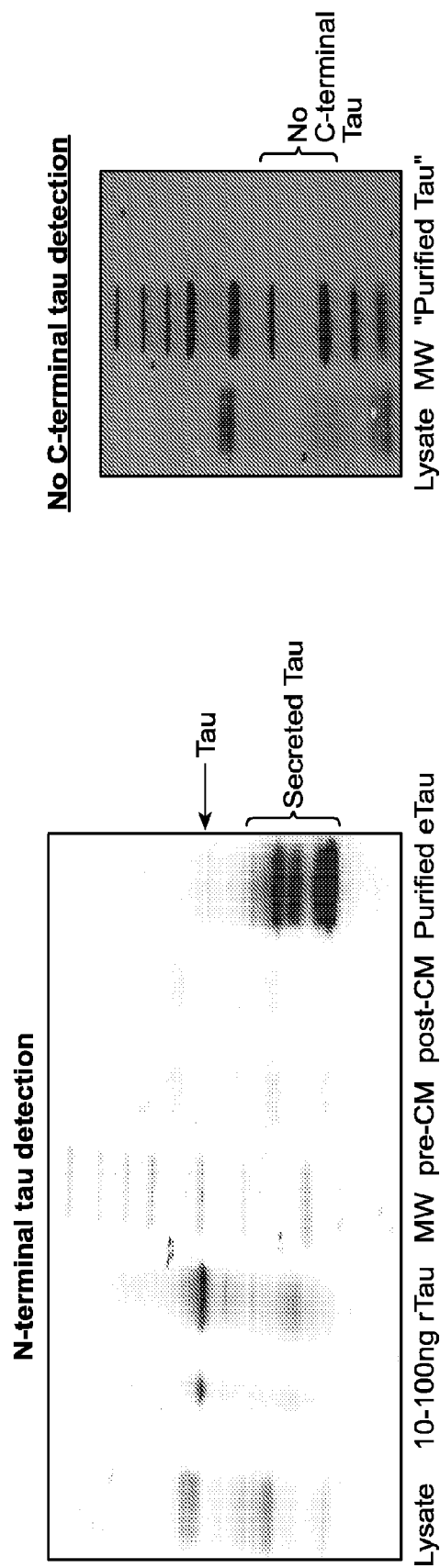
FIG. 4 is a Western blot showing IPN002-reactive eTau in conditioned medium from cortical neurons derived from a patient with AD.

FIG. 4 shows that IPN002 recognizes a weak band at the full length molecular weight size of 50 kd in the IPN001 eluate and multiple IPN002 reactive eTau bands from 20-30 kd in size. In contrast, the Dako C-terminal antibody probe of the Tau14 eluate showed no immunoreactive bands, suggesting that the AD iPSC-conditioned media contains N-terminal forms of tau, but not C-termini intact tau.

To determine the sequence of the IPN002 immunoreactive bands, the remainder of the sample was separated on SDS-PAGE, stained with Coomassie, and eTau bands present in four bands (20-30 kd) cut out of the gel, as well as full length tau, and submitted for LC/MS/MS analysis. These gel slices were proteolytically processed separately with three distinct proteases: trypsin, chymotrypsin, and elastase. Proteolytic fragments were separated and processed by nano LC/MS/MS with a Waters NanoAcquity HPLC system interfaced to a ThermoFisher Orbitrap Velos Pro. The sequence data were searched using Mascot against the Swissprot Human database.

Amino acid sequences of eTau fragments referred to as eTau1 (amino acids 2-166; amino acids 2-172; and amino acids 2-176), eTau2, eTau3, and eTau4 are depicted in FIG. 1A.

Example 2: Active Immunization with a Tau Peptide

A tau peptide is tested in a non-human animal model for the ability of the tau peptide to induce an immune response in the animal model that is effective to reduce one or more pathological features of a tauopathy.

Suitable non-human animal models include a transgenic mouse that expresses a human tau isoform with the P301L mutation; e.g., a JNPL3 transgenic mouse that expresses mutant (P301L) tau. See, e.g., Lewis et al. (2000) *Nat. Genet.* 25:402; and Lin et al. (2003) *Am. J. Pathol.* 162:213.

A tau peptide of the present disclosure is adsorbed onto aluminum phosphate particles to generate an immunogen, or is linked to a carrier such as keyhole limpet hemocyanin (KLH). The tau peptide immunogen is injected subcutaneously (with or without CFA or IFA) into the mice, beginning at about 2 months of age, or 4 months of age, or older than 4 months; subsequent immunizations are carried out approximately every two weeks. Control mice are administered aluminum phosphate particles without the tau peptide.

An antibody response to the peptide is determined using an ELISA to detect the presence in plasma taken from the mice of antibody specific for the tau peptide immunogen. Wells of a 96-well plate are coated with a subject tau peptide; plasma from a mouse is added to the well; and binding of antibody present in the plasma is detected using a detectably labeled secondary antibody specific for mouse IgG. For example, the secondary antibody can be linked to an enzyme such as horse radish peroxidase.

The effect of immunization with the tau peptide on various pathological features of a tauopathy is determined. For example, brains of tau peptide-immunized mice and control mice are analyzed using immunohistochemical methods for the presence of tau aggregates. For example, the dentate gyrus of tau peptide-immunized mice and control mice are analyzed using immunohistochemical methods for the presence of tau aggregates. The presence and amount of neurofibrillary tangles can be assessed.

The effect of immunization with the tau peptide on behavioral features of a tauopathy can be analyzed. See, e.g., Carter, R. J., Morton, J. and Dunnett, S. B. 2001. Motor Coordination and Balance in Rodents. Current Protocols in Neuroscience. 8.12.1-8.12.14. For example, locomotor activity can be tested. Tau peptide-immunized mice and control mice can be subjected to a rotarod test (see, e.g., Jones and Roberts (1968) *J Pharm Pharmacol.* 1968 April; 20(4):302-4. "The quantitative measurement of motor incoordination in naive mice using an accelerating rotarod"); and/or a traverse beam test. See, e.g., Brooks and Dunnett (2009) *Nat. Rev. Neurosci.* 10:519-29: "Tests to assess motor phenotype in mice: a user's guide".

The effect of immunization with the tau peptide on cognitive function can be tested. For example, tau peptide-immunized mice and control mice can be subjected to a spontaneous object recognition test (which measures deficits in short-term memory). See, e.g., Ennaceur and Delacour (1988) *Behav. Brain Res.* 31:47. Behavioral tests designed to assess learning and memory deficits can be employed. An example of such as test is the Morris Water maze (Morris (1981) *Learn Motivat* 12:239-260). Memory and learning deficits can be studied using a 3 runway panel for working memory impairment (attempts to pass through two incorrect panels of the three panel-gates at four choice points) (Ohno et al. *Pharmacol Biochem Behav* 57:257-261 (1997)).

Example 3: Passive Immunization with an Anti-Tau Antibody

An anti-tau antibody is tested in a non-human animal model for the ability of the anti-tau antibody to reduce one or more pathological features of a tauopathy.

Suitable non-human animal models include a transgenic mouse that expresses a human tau isoform with the P301L mutation; e.g., a JNPL3 transgenic mouse that expresses mutant (P301L) tau, as noted in Example 2.

An antibody specific for a tau peptide of the present disclosure is injected intraperitoneally into mice; control mice are injected with mouse IgG. Mice are injected with anti-tau antibody at about 3 months of age, 4 months of age, or older than 4 months of age; followed by additional injections 7 days apart.

Mice can be analyzed as described in Example 2.

Example 4: Detection of eTau in Patient Samples

Materials and Methods
Conditioned Media Collection from iPS C-Derived Cortical Neurons iPSC (induced pluripotent stem cells) were generated from healthy age matched controls and Alzheimer's patients using the Yamanaka method (Takahashi et al. (2007) *Cell* 131(5), 861) as described in Dimos et al. (2008) *Science* 321:1218. iPSC were differentiated to cortical neurons largely in line with published protocols using the dual SMAD monolayer method (Chambers et al. (2009) *Nat. Biotechnol.* 27:275) followed by cortical neuron differentiation as described in Burkhardt et al. (2012) Mol. Cell Neurosci. 56C:355-364. iPSC-derived cortical neurons (iPSC-CN), cultured for 108 days, were washed, fresh media added, and conditioned media collected after three days unless otherwise noted. Multiple differentiations from the lines were conducted to ensure reproducibility of the eTau levels. Conditioned media was spun at 15,000 rpm for 15 minutes prior to processing for Western blot or tau ELISA. For the brefeldin A experiment, iPSC-CN cultures were washed with PBS prior to addition of fresh media with and without 1 µM brefeldin A and media conditioned for one hour prior to collection.

Conditioned Media Collection from Human Primary Cortical Neurons

Human cortical neuron cultures (HCC) were prepared as described in Wright et al. (2007) *Neurobiol. Aging* 28:226. Briefly, human fetal cerebral cortical tissue was obtained by Advanced Bioscience Resources (Alameda, Calif.) and complied with federal guidelines for fetal research and with the Uniformed Anatomical Gift Act. The tissue was rinsed in Hank's buffered saline solution (Cellgro) and triturated in the presence of 1 µg/ml DNase (EMD) and passed through a 100 µm cell strainer. After centrifugation the pellet was resuspended in 0.05% trypsin/EDTA (Invitrogen) for 20 min at 37° C. Trypsin was inactivated by adding an equal volume of media containing 10% fetal bovine serum (FBS) and sample gently triturated again in presence of DNase. After centrifugation, cells were resuspended in plating media (Neurobasal containing B27, Invitrogen) and counted. Cells were plated in plates or on coverslips coated with poly-d-lysine with laminin. Three week old HCC were washed, fresh media added and media collected after three days of conditioning. Conditioned media was spun at 15,000 rpm for 15 minutes prior to processing for Western blot.

P301L Mouse ISF and Human CSF Collections

Mice were anesthetized using isoflurane (2%, 800 mL/min $O_2$). Bupivacain/epinephrine was used for local analgesia and fynadine or carprophen for peri-/post-operative analgesia. The animals were placed in a stereotaxic frame (Kopf instruments, USA). Push-pull microdialysis probes (phosphatidyl ethanolamine (PEE) membrane, Brainlink, the Netherlands) were inserted into the hippocampus (3 mm exposed surface). Microdialysis sampling was performed 24 and 48 hours after surgery. On the days of the sampling, the probes of the animals were connected with fluorinated ethylene propylene (FEP) tubing to a microperfusion pump (Harvard PHD 2000 Syringe pump, Holliston, Mass. or similar). Microdialysis probes were perfused with artificial CSF (aCSF) containing 147 mM NaCl, 3.0 mM KCl, 1.2 mM $CaCl_2$ and 1.2 mM $MgCl_2$, and 0.15% bovine serum albumin (BSA) at a flow rate of 0.75 µL/min. Microdialysis samples were collected for 60 minute periods. After the stabilization period, basal samples were collected. On the second day of sampling, the above procedure was repeated (Brains Online) The interstitial fluid (ISF) was spun at 15,000 rpm for 15 minutes and cleared supernatants used for eTau Western blots.

10 mls of CSF (Precision Med) from a pool of 10 healthy (Precision Med), 10 AD patients (Precision Med) and 10 PSP patients were collected, spun at 15,000 rpm for 15 minutes, supernatants precleared on IgG affinity resin followed by tau isolation on an IPN002 anti-tau affinity resin, washed, eluted with 50 mM glycine, pH 2.3 with 150 mM NaCl into a tube containing 1M TBS, pH 8.3 to neutralize the pH, concentrated on YM10 filters and prepared for tau Western blots. iPSC-CN conditioned media from a fAD PSEN1 patient was similarly isolated as a positive control to compare banding patterns.

Western Blots

Conditioned media were diluted in Laemmli buffer (Sigma). Cultured neurons were rinsed with PBS before incubation in 0.05% trypsin in DMEM (Invitrogen), rinsed and lysed in Laemmli buffer. All samples were boiled, separated on tris-glycine polyacrylamide gels (Invitrogen) and transferred to nitrocellulose using iBlot (Invitrogen). Membranes were incubated in blocking buffer (LiCor), probed with 0.5 µg/ml IPN001 antibody to tau and antibody to β-actin (1:2000; Abcam) in blocking buffer containing 0.1% Tween-20, and anti-mouse 680 and anti-rabbit 800 secondary antibodies (LiCor). Blots were scanned with the Odyssey SA infrared imaging system and analyzed using Odyssey SA software (LiCor).

Tau ELISA

Media were collected after a three day conditioning period from iPSC-derived cortical neuron cultures and assayed using an Alphascreen homogeneous assay to measure tau. 10 µg/ml anti-tau AlphaLISA acceptor beads and 1 nM biotinylated-anti-tau antibody were mixed with conditioned media overnight at room temperature. 40 µg/ml streptavidin-donor beads (Perkin Elmer) were added for 30 minutes at room temperature and the plate read on Envision plate reader.

eTau Purification

Conditioned media collected from iPSC-CN from AD patients was spun at 15,000 rpm for 15 minutes, supernatants collected and precleared on an IgG affinity resin. The precleared supernatant was passed through an IPN002 anti-tau antibody resin, washed and eTau eluted with 50 mM sodium citrate, pH 2.3 with 150 mM NaCl into a tube containing 1M TBS, pH 8.3 to neutralize the pH. The eluate was concentrated and buffer exchanged to PBS.

Results

Assays were conducted to detect eTau fragments in various fluids. The results are depicted in FIG. 5.

As shown in FIG. 5A, left panel, endogenous tau is secreted from cortical neurons derived from human induced pluripotent stem cells (human iPSC-cortical neurons; iPSC-CN), where the secreted Tau is referred to as extracellular Tau or "eTau." As shown in FIG. 5A, second panel from left, eTau is also present in conditioned media from human primary neurons (human cortical cells; "HCC"), confirming that eTau is not an artifact of iPSC-differentiation. These eTau fragments were also detected in neuronal lysates, suggesting that tau is cleaved inside neurons prior to eTau secretion.

As shown in FIG. 5A, middle panel, similar tau fragments were detected in interstitial fluid (ISF) from P301L tau mice, where full length tau was not detected in either system. P301L mice are transgenic for a form of human tau having a P301L mutation; P301L mice are models for human tauopathy. See, e.g., Gotz et al. (2001) *J. Biol. Chem.* 276:529; and Lewis et al. (2000) *Nature Genetics* 25:402.

As shown in FIG. 5A, right panels, eTau levels are increased in CSF from AD patients, and in multiple lines from familial AD (fAD) patients compared to lines from healthy patients. As shown in FIG. 5A, right panels, eTau was also detected in CSF from PSP patients.

To elucidate mechanisms of eTau secretion, the kinetics of eTau release were characterized. The data, presented in FIG. 5B, show that eTau is secreted from healthy and fAD-derived neurons as quickly as two minutes after fresh media is added.

Neurons were treated with Brefeldin A, an inhibitor of the canonical ER-Golgi secretory pathway. As shown in FIG. 5C, Brefeldin A had no significant effect on eTau secretion, suggesting a non-canonical pathway for eTau secretion. These data show that eTau is rapidly secreted from neurons and suggest an intriguing parallel between elevated eTau levels in AD neurons and the increased tau levels in CSF from AD patients.

Figure 6:
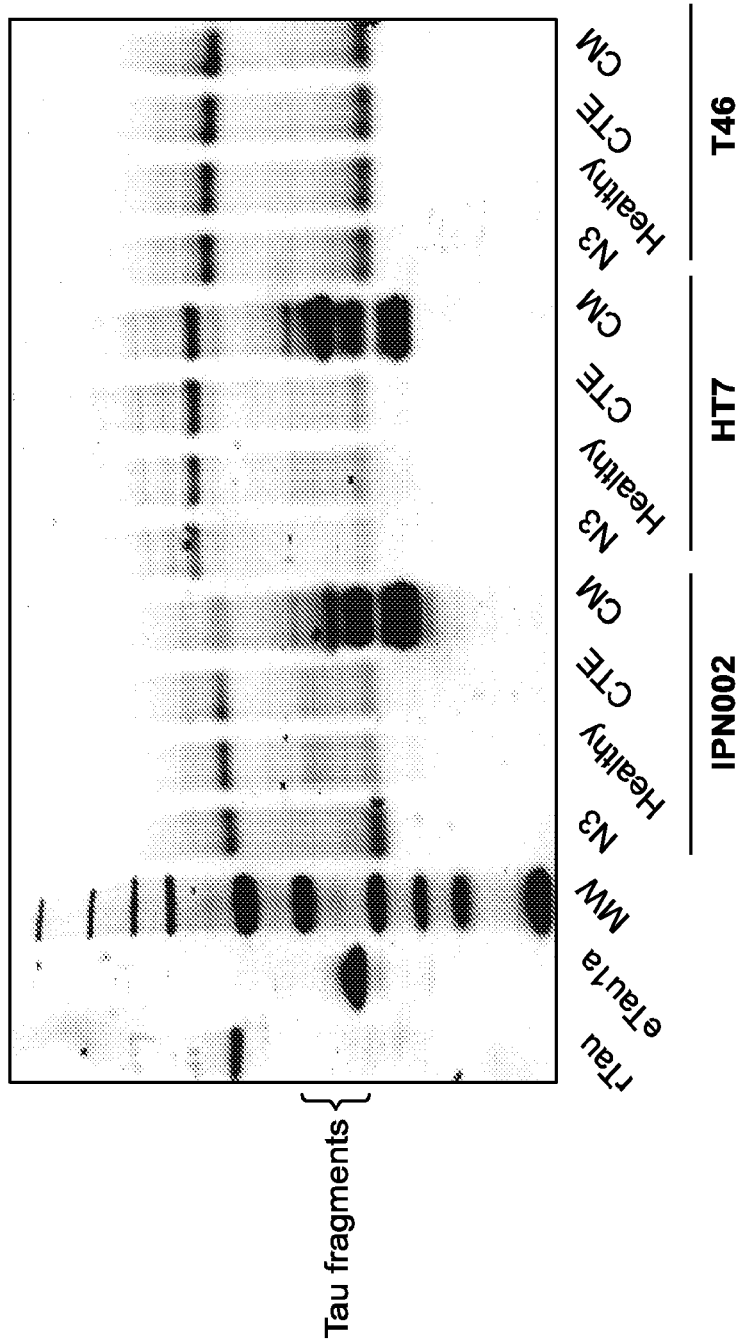
FIG. 6 depicts detection in protein blots showing detection of Tau fragments present in cerebrospinal fluid (CSF) from National Football League (NFL) players with likely chronic traumatic encephalopathy (CTE).

CSF from healthy individuals and from individuals with likely chronic traumatic encephalopathy (CTE) was immunoprecipitated with IPN002 (a mAb that recognizes an epitope within amino acids 15-24 of Tau); HT7 (a mouse monoclonal antibody that binds an epitope within amino acids 159-163 of human tau); or T46 (an antibody that binds an epitope in a C-terminal region of Tau). The immunoprecipitated material was separated on a gel, the separated material was transferred to a membrane, and the membrane was probed with IPN001 (a mAb that recognizes and epitope within amino acids 1-30 of Tau). The data are shown in FIG. 6. N3 is a medium control; CM is conditioned medium from fAd iPSC-CN line 11369.1. Recombinant full-length Tau ("rTau") and eTau1a (amino acids 2-166; SEQ ID NO:3), as well as molecular weight (MW) markers, were run in the same gel. The data indicate that Tau fragments are present in CSF of individuals with CTE, and that these Tau fragments are recognized by IPN002 and HT7, but not by T46.

Figure 7:
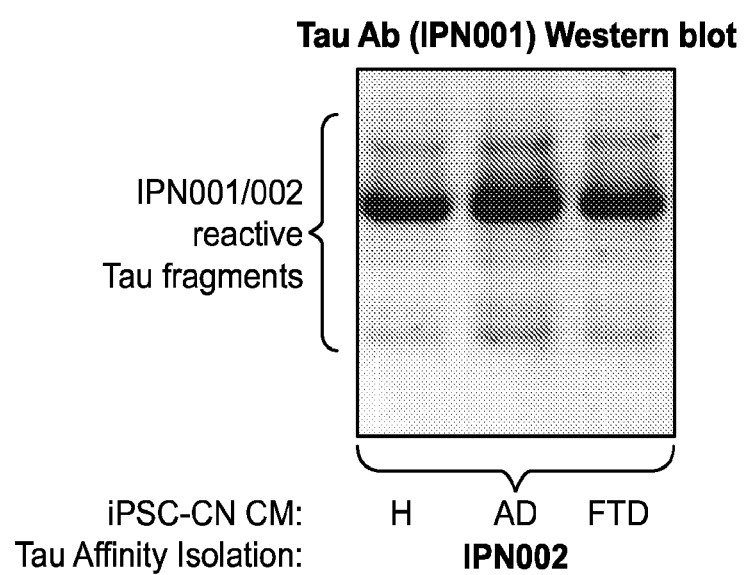
FIG. 7 depicts protein blots showing detection of Tau fragments in conditioned medium (CM) of iPSC-CN from healthy individuals (H), individuals with AD, and individuals with frontotemporal dementia (FTD).

Conditioned medium from iPSC-CN derived from cells obtained from healthy individuals, individuals with AD, and individuals with FTD was immunoprecipitated with IPN001. The immunoprecipitated material was separated on a gel, the separated material was transferred to a membrane, and the membrane was probed with IPN002. The data are shown in FIG. 7. As shown in FIG. 7, IPN001/IPN002-reactive Tau fragments are present in iPSC-CN derived from cells obtained from individuals with AD and from individuals with FTD.

Example 5: eTau Induces Neuronal Hyperactivity

Methods

Whole cell patch clamp recording from iPSC-CN cultured on monolayer of normal human astrocytes using micropipette (2-5 MOhm) were filled with solution containing (mM): K-methyl-sulfate (140), NaCl (10), $CaCl_2$ (1), Mg-ATP (3); Na-GTP (0.4), EGTA (0.2), HEPES (10), Phosphocreatine (10) with adjusted pH=7.3, and mOsm=305. Neurons were perfused (2 ml/min) with artificial cerebral spinal fluid containing (mM): NaCl (140), KCl (2.5), $MgCl_2$ (2) $CaCl_2$ (2), Hepes (10), D-Glucose (10), sucrose (20), adjusted pH=7.4 mOsm=310. Recordings were made using pClamp-10.3 data acquisition software (Molecular Devices) and MultiClamp 700B amplifier (Axon Instrument; Foster City Calif.). Puff application of eTau, or eTau with inhibitors, tetrodotoxin (TTX) (Tocris), MK801 (Sigma), or NBQX (Tocris), was performed using MiniSquirt microperfusion system (AutoMate, Berkeley, Calif.). Off-line data analysis used Clampfit 10.2 analysis software (Molecular Devices). Recordings were conducted at 34-37° C.

Results

To determine whether eTau can alter neuronal function, purified eTau fragments were applied to iPSC-CN or HCC. As shown in FIG. 8A, addition of eTau onto these neurons promoted hyperactivity. As shown in FIG. 8B, eTau-induced hyperactivity was inhibited by tetrodotoxin (TTX) and by the NMDA and AMPA glutamate receptor antagonists, MK801 and NBQX, respectively. TTX blocks action potentials in nerves by binding to the voltage-gated, fast sodium channels in nerve cell membranes. These data suggest that eTau-induced neuronal hyperactivity is dependent on action potential-mediated release of glutamate. In contrast, as shown in the middle panel of FIG. 8A, application of full length tau produced no detectable changes in neuronal activity even at substantially higher concentrations, showing that eTau-induced hyperactivity is dependent on tau fragments. These eTau-induced hyperactivity results strongly suggest that calcium mobilization could be occurring in the neurons. To determine whether calcium mobilization occurs in the neurons, the effect of eTau on calcium mobilization was tested. As shown in FIG. 8C, eTau-1a robustly mobilized calcium. This type of neuronal hyperactivity, if sustained in a chronic setting such as in AD, could result in neuronal dysfunction through altered synaptic firing and aberrant neuronal stimulation.

Example 6: eTau Uptake by Mouse Cortical Neurons

Methods eTau Uptake by Mouse Cortical Neurons

Mouse cortical cells (MCC) were prepared from 15-day old mouse cortices/hippocampus (BrainBits) as described by Wright et al. ((2012) *Neurobiol. Aging* 33:1379) and cultured for 3 weeks in Neurobasal Medium including Pen/Strep, glutamax and B27 (Invitrogen). MCC were treated with 50 nM eTau in growth medium for 1 day unless otherwise noted. eTau uptake assays were also performed in the presence of 5 µg/ml cytochalasin D (Sigma) for 1 hour or after MCC incubation at 4° C. followed by eTau treatment for 1 hour.

Immunofluorescence

MCC were rinsed with PBS, fixed in 4% paraformaldehyde, blocked with 10% normal donkey serum (Jackson ImmunoResearch) in PBS, permeabilized (unless otherwise specified) with 0.2% Triton-x-100 in PBS for 15 minutes, and stained using IPN001 antibody to tau with donkey-anti-mouse-A488 secondary antibody (Molecular Probes) and DAPI (Invitrogen). Images were acquired using the Leica DMI 600 B microscope at 40× using the LAS AF software (Leica). Confocal images were acquired using the Nikon Eclipse Ti confocal microscope (Nikon).

Results

To address whether eTau is taken up by recipient neurons, human eTau was purified from AD patient iPSC-CN conditioned media and added to mouse cortical neurons. It was found that eTau associates with cortical neurons as detected by human tau blotting (FIG. 9A) and tau immunofluorescence (FIG. 9B). As shown in FIG. 9B, cell permeabilization is required to detect eTau, confirming that eTau is inside the neurons. eTau is predominantly distributed within the soma but is also present along neuronal processes. The pattern of eTau, as detected by confocal imaging, appears to be in cytosolic vesicles and is suggestive of eTau internalization via endocytosis, as shown in FIG. 9C.

To understand the mechanism of eTau uptake into neurons, the rate of uptake of eTau was characterized. As shown in FIG. 8D, eTau begins to be taken up by recipient neurons as soon as 2 minutes and reaches a maximum level at 60 minutes with steady state levels maintained through 72 hours. eTau likely is taken up by an active transport mechanism since treatment with cytochalasin D, an actin polymerization inhibitor and incubation at 4° C. inhibit uptake, as shown in FIG. 9E. Taken together these data demonstrate for the first time the endogenous secretion of a novel form of tau, eTau, and establish a neuronal model of tau uptake and a potential role for eTau in AD.

Figure 10:
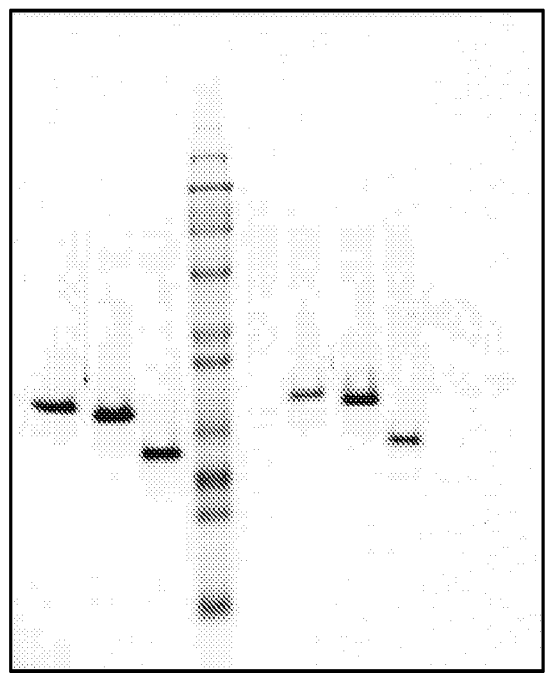
FIG. 10 depicts uptake of recombinant eTau polypeptides by mouse cortical neurons.

Uptake of eTau into mouse cortical neurons (MCC) in vitro is depicted in FIG. 10. Lane 1 depicts eTau-1a (recombinant eTau-1a; "reTau1a") in medium; Lane 2 depicts eTau2 (recombinant eTau2; "reTau2") in medium; Lane 3 depicts recombinant eTau3 ("reTau3") in medium; Lane 4 is a MW ladder; Lane 5 depicts MCC not cultured in the presence of eTau; Lane 6 depicts reTau1a in MCC; Lane 7 depicts reTau2 in MCC; and Lane 8 depicts reTau3 in MCC. The data show that eTau is taken up by MCC in vitro.

Example 7: In Vivo Uptake of eTau

Figure 11:
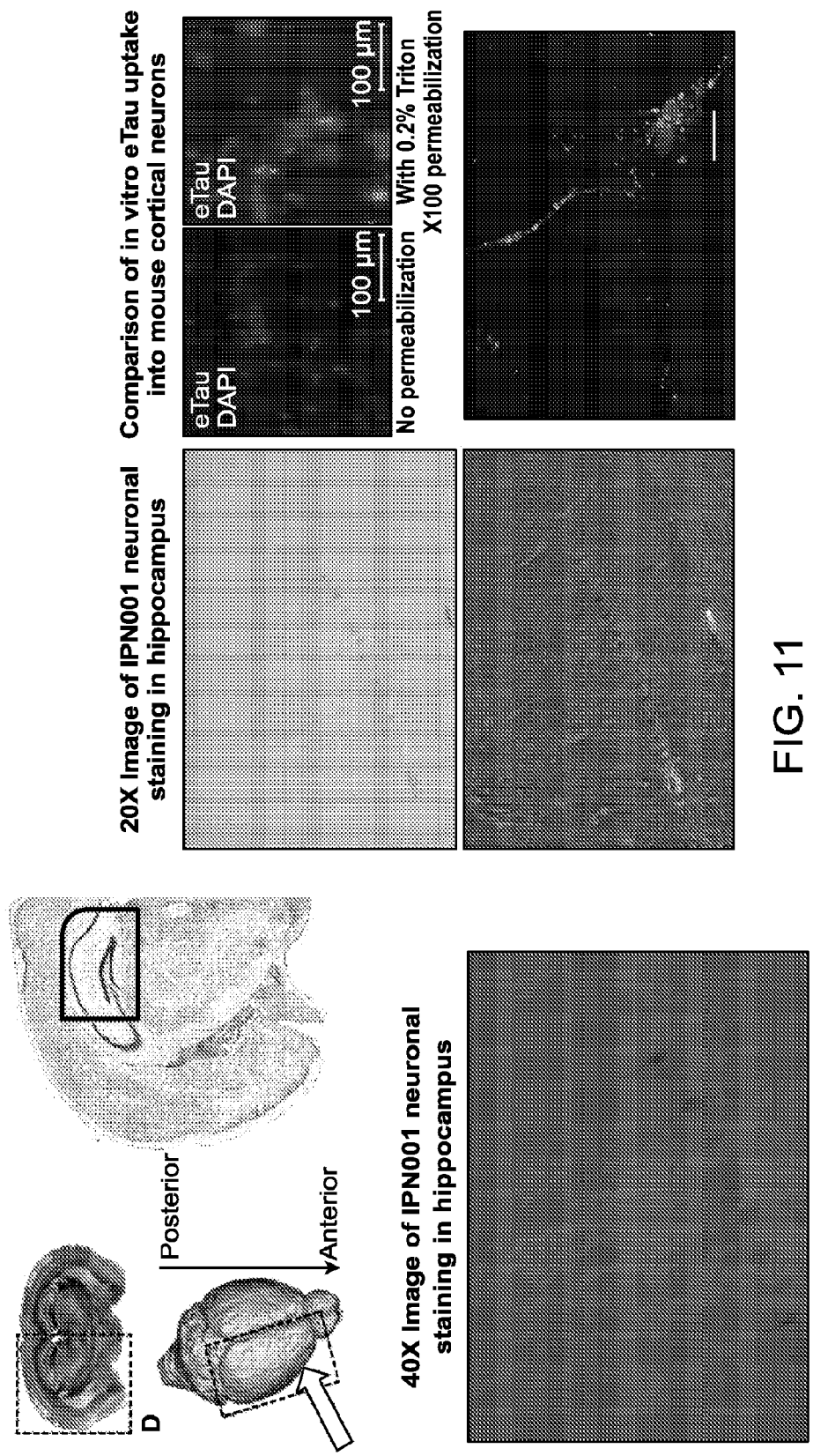
FIG. 11 depicts the effect of stereotactic injection of eTau into the hippocampus.

Extracellular Tau fragments were injected into mice. Hippocampal brain slices were stained with IPN001. The results are shown in FIG. 11. As shown in FIG. 11, eTau is taken up by neurons in the hippocampus.

Figure 12:
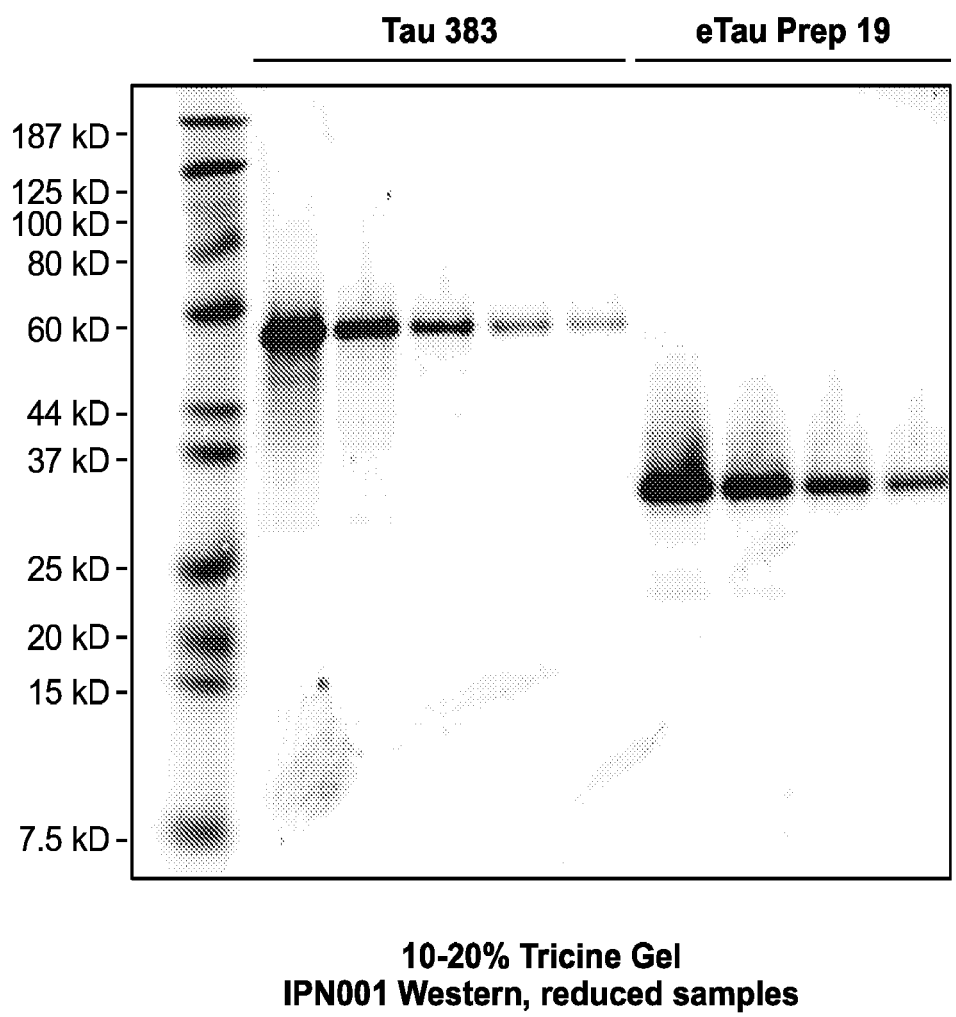
FIG. 12 depicts Western blot analysis of eTau Prep19.

Example 8: Mass Spectrometry Analysis of eTau from Neuronal Culture Media eTau secreted into conditioned medium from iPS-derived cortical neurons was analyzed by mass spectrometry (MS). iPSC were generated from fibroblasts from a skin punch of an AD patient, as described in Example 1, and were differentiated to cortical neurons. Conditioned medium from these cortical neurons was subjected to affinity chromatography using IPN001, an antibody that binds tau. The affinity-purified eTau thus obtained was designated "Prep 19" eTau. Affinity purified Prep 19 eTau was separated by 10-20% gradient Tricine polyacrylamide gel electrophoresis. The gel was blotted and the blot stained with IPN001, an antibody binds tau. The results, shown in FIG. 12, show that the ~30 kDa band was the major Tau product present in the conditioned medium. Tau-383 (full-length) is shown for comparison.

Figure 13:
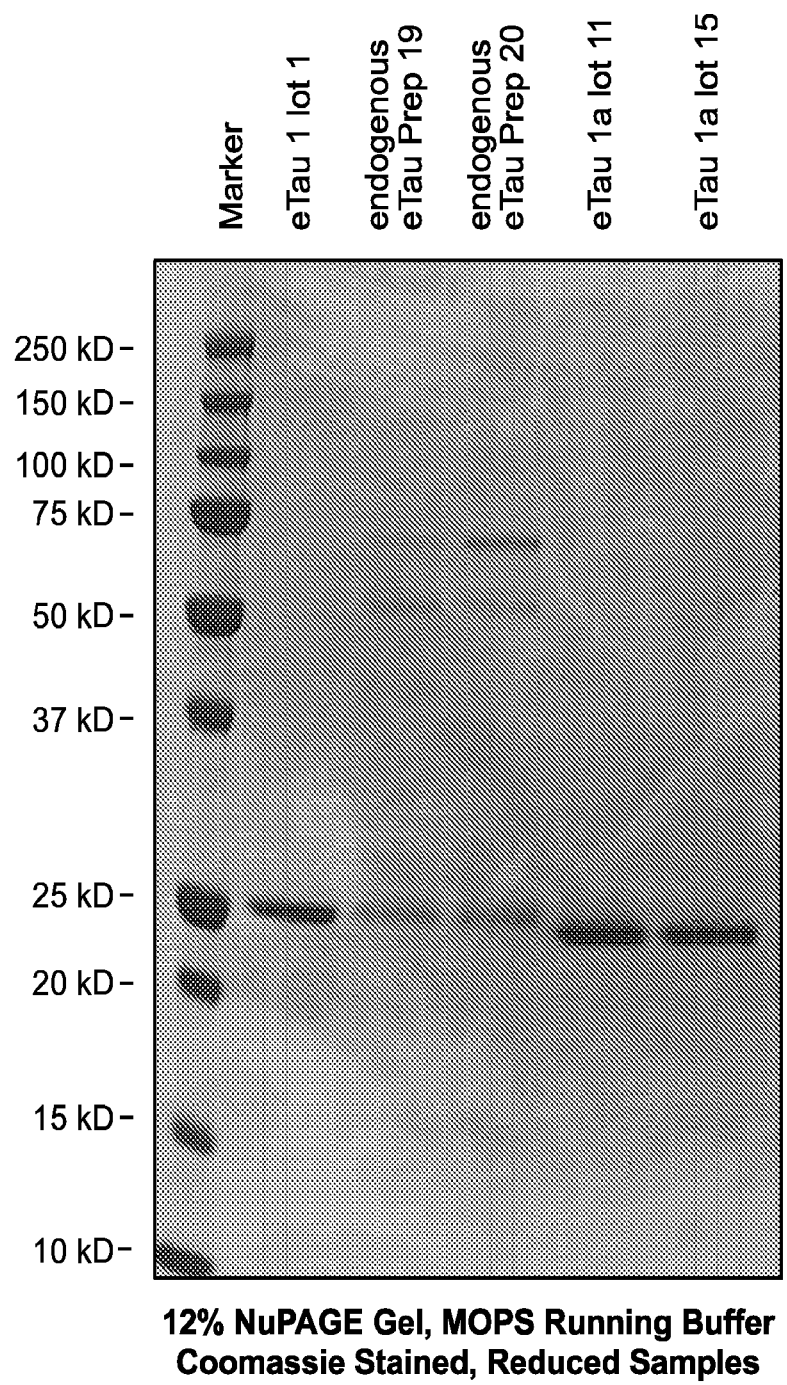
FIG. 13 depicts a Coomassie-stained gel of: i) recombinantly produced eTau 2-172 ("eTau1 lot 1"); ii) eTau present in conditioned medium of cortical neurons differentiated from iPSCs derived from a patient with AD ("endogenous eTau Prep19" and "endogenous eTau Prep20"); and iii) recombinantly produced eTau 2-166 ("eTau1a lot 11"; and "eTau1a lot 15").

FIG. 13 depicts a Coomassie-stained gel of: i) recombinantly produced eTau 2-172 ("eTau1 lot 1"); ii) eTau present in conditioned medium of cortical neurons differentiated from iPSCs derived from a patient with AD ("endogenous eTau Prep19" and "endogenous eTau Prep20"); and iii) recombinantly produced eTau 2-166 ("eTau1a lot 11"; and "eTau1a lot 15"). Proteins in the samples were separated on a 12% NuPAGE gel, using MOPS running buffer. The gel was then stained with Coomassie blue. FIG. 12 shows that recombinantly produced eTau 2-166 ("eTau1a lot 11"; and "eTau1a lot 15") samples had a molecular weight (MW) slightly lower than that of eTau present in conditioned medium of cortical neurons differentiated from iPSCs derived from a patient with AD. The eTau present in conditioned medium of cortical neurons differentiated from iPSCs derived from a patient with AD had a similar MW to that of recombinantly produced eTau 2-172.

Figure 14:
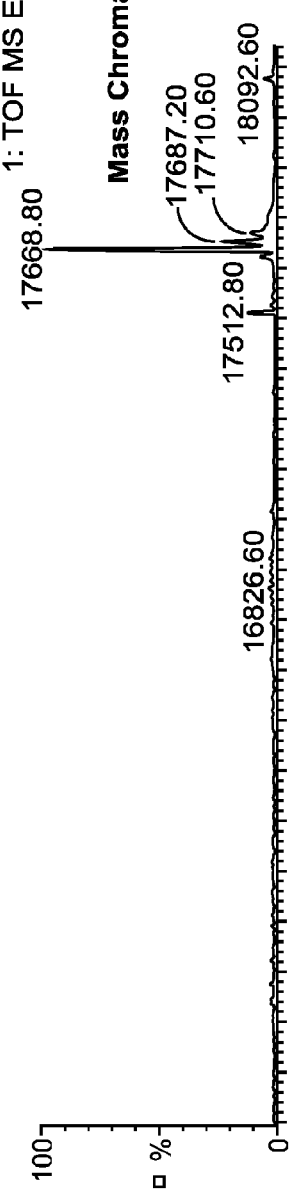
FIGS. 14A-C depict eTau species present in conditioned medium of cortical neurons differentiated from iPSCs derived from a patient with AD.

The endogenous eTau Prep 19 was affinity purified and subjected to mass spectrometry (MS) analysis. As shown in FIG. 14B, a predominant peak of 17668.80, and minor peaks of 17512.80, 18092.60, and 17710.60 were observed. FIG. 14A depicts the amino acid sequence of eTau 2-166 (SEQ ID NO:3), compared to Tau 0N3R (SEQ ID NO:73). The C-terminal amino acids for eTau 2-172 and eTau 2-176 are depicted by arrows. The major species with a MW of 17669 is consistent with an acetylated fragment of tau containing amino acids 2-172. FIG. 14C provides a table showing the expected and observed molecular weights of eTau species present in endogenous eTau Prep19.

Example 9: Anti-Tau Antibodies

As described above, several fragments of tau present in the conditioned media of cortical neuron cultures derived from AD patient induced pluripotent stem cells were identified. These fragments of tau were purified from culture supernatants by affinity chromatography using a tau-specific monoclonal antibody. After purification, four major fragments (eTau1, eTau2, eTau3 and eTau4) were identified and sequencing of these fragments by LC/MS confirmed that they were derived from the N-terminal domain of tau.

To prepare antibodies against each fragment of eTau and to identify neoepitope antibodies (i.e. antibodies against epitopes generated after proteolytic cleavage of a protein) mice were immunized with peptides derived from the C-terminal region of each peptide (Table 2) conjugated to bovine serum albumin (BSA) via a free cysteine residue.

Briefly, antibodies to eTau fragments were produced as follows: NZBW mice were immunized with specific peptides (Table 2) conjugated to BSA and the resulting hybridoma library was screened with peptides containing the same sequence or extended peptide sequences (Table 2) immobilized onto 96-well plates using techniques known to those skilled in the art (see, e.g., Galfre et al., Methods in Enzymology 73:346 (1981). Tau-derived sequences of peptides used as immunogens are underlined in FIG. 1A. Flow cytometry was used to generate single cell clones, and supernatants from these individual clones were screened for binding to biotin-labeled full-length tau or recombinantly expressed eTau fragments using a solution phase monoclonal antibody capture assay, such as that disclosed, e.g., in Nix et al., in Immunoassays, A Practical Approach, editor J. P. Gosling, pp. 239-261, Oxford University Press (2000).

TABLE 2

Peptides used to generate and screen antibodies specific for eTau fragments

| Target Protein | Immunogen[1] | Screening peptide |
|---|---|---|
| eTau1 | CSLPTPPTREPK (SEQ ID NO: 93) | CSLPTPPTREPKKVAVVRTP (SEQ ID NO: 94) |
| eTau2 | CSSPGSPGTPGSR (SEQ ID NO: 95) | CSSPGSPGTPGSRSRTPSL (SEQ ID NO: 96) |
| eTau3 | CRIPAKTPPAPK (SEQ ID NO: 97) | CRIPAKTPPAPKTPPSS (SEQ ID NO: 98) |
| eTau4 | CEDEAAGHVTQAR (SEQ ID NO: 99) | CEDEAAGHVTQARMVSKS (SEQ ID NO: 100) |

[1]Cysteine amino acid in plain text was used to conjugate the peptide to BSA

Table 3 summarizes the number of monoclonal antibodies identified in each library screen and identifies the highest affinity clones that were selected for further characterization. The eight selected monoclonal antibodies were purified from tissue culture supernatants by protein A chromatography and the purified antibodies further characterized in direct binding ELISA type assays.

TABLE 3

Results of hybridoma screening: identification of antibodies specific for eTau fragments

| Target Protein | Immunogen[1] | Number of Positive Clones | Selected Clones |
|---|---|---|---|
| eTau1 | CSLPTPPTREPK (SEQ ID NO: 93) | 14 | 7295-M6, -M8 |
| eTau2 | CSSPGSPGTPGSR (SEQ ID NO: 95) | 20 | 7297-2M1 |
| eTau3 | CRIPAKTPPAPK (SEQ ID NO: 97) | 10 | 7298-M1, -M2 |
| eTau4 | CEDEAAGHVTQAR (SEQ ID NO: 99) | 20 | 7299-M2, -M5, -M9 |

[1]Cysteine amino acid in plain text was used to conjugate the peptide to BSA

As shown in Table 4, seven of the purified anti-tau antibodies bound to full-length recombinant tau (0N4R) with high affinity ($K_D$ range 8.00E-11 to 6.68E-9 M). Surprisingly, antibody 7299-M2, identified in a hybridoma library from mice immunized with a peptide from the C-terminus of the eTau4 fragment, did not show any detectable binding to full-length tau. To further define the specificity of the purified monoclonal antibodies, binding assays were performed using each isolated recombinant eTau fragment.

TABLE 4

Characterization of anti-eTau monoclonal antibodies

| Antibody | Isotype | Target protein | Binding to Tau 0N4R $K_D$ (M) |
|---|---|---|---|
| 7295-M6 | IgG2b | eTau1 | 1.17E-10 |
| 7295-M8 | IgG2b | eTau1 | 8.00E-11 |
| 7297-2M1 | IgG1 | eTau2 | 2.21E-09 |
| 7298-M1 | IgG2a | eTau3 | 6.68E-09 |
| 7298-M2 | IgG2a | eTau3 | 4.41E-09 |
| 7299-M2 | IgG1 | eTau4 | ND[1] |
| 7299-M5 | IgG2b | eTau4 | 5.11E-10 |
| 7299-M9 | IgG1 | eTau4 | 2.77E-10 |

[1]ND—no detectable binding to Tau 0N4R

Figure 15:
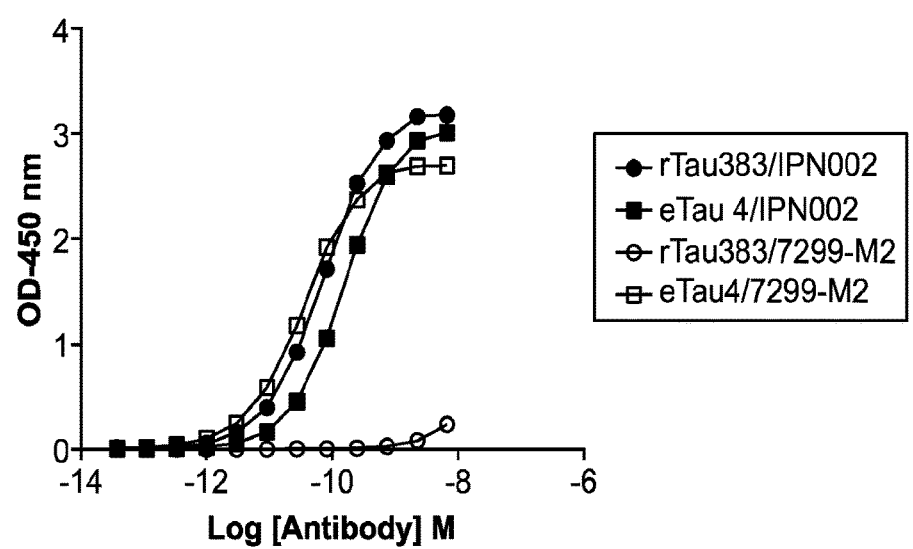
FIG. 15 depicts binding of 7299-M2 or IPN002 to recombinant full-length tau (rTau383) or eTau4.

As shown in Table 5, the antibodies demonstrated the expected range of specificity. For example, antibodies generated against the C-terminus of eTau1 only bound to the eTau1 fragment. Antibodies generated against eTau2 bound both eTau2 and eTau1 because eTau1 contains the entire eTau2 sequence. Antibody 7299-M2 demonstrated a unique specificity for eTau4, with no detectable binding to other eTau fragments (Table 5 and FIG. 15). As the eTau4 fragment is contained within all of the longer eTau fragments these data suggest that antibody 7299-M2 is specific for a novel epitope (neoepitope) defined by the C-terminus of eTau4.

TABLE 5

Binding of selected monoclonal antibodies to specific eTau fragments

| Antibody | Target protein | eTau1 $K_D$ (M) | eTau2 $K_D$ (M) | eTau3 $K_D$ (M) | eTau4 $K_D$ (M) |
|---|---|---|---|---|---|
| 7295-M6 | eTau1 | 5.28E-11 | ND | ND | ND |
| 7295-M8 | eTau1 | 4.40E-11 | ND | ND | ND |
| 7297-2M1 | eTau2 | 1.00E-10 | 9.00E-11 | ND | ND |
| 7298-M1 | eTau3 | 3.00E-09 | 1.00E-09 | 1.00E-10 | ND |
| 7298-M2 | eTau3 | 2.00E-09 | 7.00E-10 | 8.00E-11 | ND |
| 7299-M2 | eTau4 | ND[1] | ND | ND | 8.00E-10 |
| 7299-M5 | eTau4 | 6.00E-10 | 1.00E-09 | 6.00E-10 | 5.00E-10 |
| 7299-M9 | eTau4 | 6.00E-10 | 7.00E-10 | 1.00E-09 | 6.00E-10 |

[1]ND—no detectable binding

Amino acid sequencing of the VH and VL regions of each of the anti-Tau antibodies was conducted using known methods (MCLAB, South San Francisco, Calif.). Specifically, cell pellets were prepared for each monoclonal antibody and RNA was extracted using an RNAqueous®-4PCR kit (Life Technologies Inc., Grand Island, N.Y.). V-regions were amplified by reverse transcription-polymerase chain reaction (RT-PCR) using degenerate primer pools for murine antibody signal sequences together with constant region primers for IgMVH, IgGVH, IgκVL and IgλVL. The polymerase chain reaction (PCR) products obtained from each of the successful amplifications were purified and cloned into a 'TA' cloning vector (pGEM-T® Easy, Promega, Madison, Wis.) from which sequences were obtained. The deduced amino acid sequences of the VH and VL regions of each antibody are provided in FIGS. 17-20, which provide Tables 6-9. Also provided in Tables 6-9 are the CDRs of each of the respective antibodies, determined using the method described at www(dot)bioinf(dot)org(dot)uk/abs/("How to identify the CDRs by looking at a sequence").

Anti-Tau antibodies can be used in methods to detect eTau fragments in a biological sample. FIG. 16 provides an example of such an assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An antibody or antigen-binding fragment thereof that binds an epitope within SEQ ID NO:94, wherein the antibody or antigen-binding fragment thereof comprises:
   a) a light chain variable region (VL) comprising VL complementarity determining regions (CDRs), VL-CDR1, VL-CDR2, and VL-CDR3 set forth in SEQ ID NO:9, SEQ ID NO:10, and SEQ ID NO:11, respectively; and a heavy chain variable region (VH) comprising VH CDRs, VH-CDR1, VH-CDR2, and VH-CDR3 set forth in SEQ ID NO:12, SEQ ID NO:13, and SEQ ID NO:14, respectively; or
   b) a VL comprising VL CDRs, VL-CDR1, VL-CDR2, and VL-CDR3 set forth in SEQ ID NO:17, SEQ ID NO:18, and SEQ ID NO:19, respectively; and a VH comprising VH CDRs, VH-CDR1, VH-CDR2, and VH-CDR3 set forth in SEQ ID NO:20, SEQ ID NO:21, and SEQ ID NO:22, respectively.

2. The antibody or antigen-binding fragment thereof of claim 1, wherein:
   a) the VH comprises the amino acid sequence set forth in SEQ ID NO:16 and the VL comprises the amino acid sequence set forth in SEQ ID NO:15; or
   b) a) the VH comprises the amino acid sequence set forth in SEQ ID NO:24 and the VL comprises the amino acid sequence set forth in SEQ ID NO:23.

3. An antibody or antigen-binding fragment thereof that binds an epitope within SEQ ID NO:96, wherein the antibody or antigen-binding fragment thereof comprises:
   a VL comprising VL CDRs, VL-CDR1, VL-CDR2, and VL-CDR3 set forth in SEQ ID NO:65, SEQ ID NO:66, and SEQ ID NO:67, respectively; and a VH comprising VH CDRs, VH-CDR1, VH-CDR2, and VH-CDR3 set forth in SEQ ID NO:68, SEQ ID NO:69, and SEQ ID NO:70, respectively.

4. The antibody or antigen-binding fragment thereof of claim 3, wherein:

the VH comprises the amino acid sequence set forth in SEQ ID NO:72 and the VL comprises the amino acid sequence set forth in SEQ ID NO:71.

5. An antibody or antigen-binding fragment thereof that binds an epitope within SEQ ID NO:98, wherein the antibody or antigen-binding fragment thereof comprises:
   (a) a VL comprising VL CDRs, VL-CDR1, VL-CDR2, and VL-CDR3 set forth in SEQ ID NO:25, SEQ ID NO:26, and SEQ ID NO:27, respectively; and a VH comprising VH CDRs, VH-CDR1, VH-CDR2, and VH-CDR3 set forth in SEQ ID NO:28, SEQ ID NO:29, and SEQ ID NO:30, respectively; or
   (b) a VL comprising VL CDRs, VL-CDR1, VL-CDR2, and VL-CDR3 set forth in SEQ ID NO:33, SEQ ID NO:34, and SEQ ID NO:35, respectively; and a VH comprising VH CDRs, VH-CDR1, VH-CDR2, and VH-CDR3 set forth in SEQ ID NO:36, SEQ ID NO:37, and SEQ ID NO:38, respectively.

6. The antibody or antigen-binding fragment thereof of claim 5, wherein:
   a) the VH comprises the amino acid sequence set forth in SEQ ID NO:32 and the VL comprises the amino acid sequence set forth in SEQ ID NO:31; or
   b) the VH comprises the amino acid sequence set forth in SEQ ID NO:40 and the VL comprises the amino acid sequence set forth in SEQ ID NO:39.

7. An antibody or antigen-binding fragment thereof that binds an epitope within SEQ ID NO:100, wherein the antibody or antigen-binding fragment thereof comprises:
   (a) a VL comprising VL CDRs, VL-CDR1, VL-CDR2, and VL-CDR3 set forth in SEQ ID NO:41, SEQ ID NO:42, and SEQ ID NO:43, respectively; and a VH comprising VH CDRs, VH-CDR1, VH-CDR2, and VH-CDR3 set forth in SEQ ID NO:44, SEQ ID NO:45, and SEQ ID NO:46, respectively;
   (b) a VL comprising VL CDRs, VL-CDR1, VL-CDR2, and VL-CDR3 set forth in SEQ ID NO:49, SEQ ID NO:50, and SEQ ID NO:51, respectively; and a VH comprising VH CDRs, VH-CDR1, VH-CDR2, and VH-CDR3 set forth in SEQ ID NO:52, SEQ ID NO:53, and SEQ ID NO:54, respectively; or
   (c) (b) a VL comprising VL CDRs, VL-CDR1, VL-CDR2, and VL-CDR3 set forth in SEQ ID NO:57, SEQ ID NO:58, and SEQ ID NO:59, respectively; and a VH comprising VH CDRs, VH-CDR1, VH-CDR2, and VH-CDR3 set forth in SEQ ID NO:60, SEQ ID NO:61, and SEQ ID NO:62, respectively.

8. The antibody or antigen-binding fragment thereof of claim 1, wherein:
   a) the VH comprises the amino acid sequence set forth in SEQ ID NO:48 and the VL comprises the amino acid sequence set forth in SEQ ID NO:47;
   b) the VH comprises the amino acid sequence set forth in SEQ ID NO:56 and the VL comprises the amino acid sequence set forth in SEQ ID NO:55; or
   c) b) the VH comprises the amino acid sequence set forth in SEQ ID NO:64 and the VL comprises the amino acid sequence set forth in SEQ ID NO:63.

9. The antibody or antigen-binding fragment thereof of claim 1, which is humanized.

10. The antibody or antigen-binding fragment thereof of claim 3, which is humanized.

11. The antibody or antigen-binding fragment thereof of claim 5, which is humanized.

12. The antibody or antigen-binding fragment thereof of claim 7, which is humanized.

13. The antibody or antigen-binding fragment thereof of claim 1, which is an IgG1, IgG2, IgG3, or IgG4 antibody.

14. The antibody or antigen-binding fragment thereof of claim 2, which is an IgG1, IgG2, IgG3, or IgG4 antibody.

15. The antibody or antigen-binding fragment thereof of claim 3, which is an IgG1, IgG2, IgG3, or IgG4 antibody.

16. The antibody or antigen-binding fragment thereof of claim 4, which is an IgG1, IgG2, IgG3, or IgG4 antibody.

17. The antibody or antigen-binding fragment thereof of claim 5, which is an IgG1, IgG2, IgG3, or IgG4 antibody.

18. The antibody or antigen-binding fragment thereof of claim 6, which is an IgG1, IgG2, IgG3, or IgG4 antibody.

19. The antibody or antigen-binding fragment thereof of claim 7, which is an IgG1, IgG2, IgG3, or IgG4 antibody.

20. The antibody or antigen-binding fragment thereof of claim 8, which is an IgG1, IgG2, IgG3, or IgG4 antibody.

21. The antibody or antigen-binding fragment thereof of claim 1, which is a Fab, a F(ab')$_2$, scFv, or a Fv.

22. The antibody or antigen-binding fragment thereof of claim 3, which is a Fab, a F(ab')$_2$, scFv, or a Fv.

23. The antibody or antigen-binding fragment thereof of claim 5, which is a Fab, a F(ab')$_2$, scFv, or a Fv.

24. The antibody or antigen-binding fragment thereof of claim 7, which is a Fab, a F(ab')$_2$, scFv, or a Fv.

25. A pharmaceutical formulation comprising: the antibody or antigen-binding fragment thereof of claim 1, and a pharmaceutically acceptable excipient.

26. A pharmaceutical formulation comprising: the antibody or antigen-binding fragment thereof of claim 2, and a pharmaceutically acceptable excipient.

27. A pharmaceutical formulation comprising: the antibody or antigen-binding fragment thereof of claim 3, and a pharmaceutically acceptable excipient.

28. A pharmaceutical formulation comprising: the antibody or antigen-binding fragment thereof of claim 4, and a pharmaceutically acceptable excipient.

29. A pharmaceutical formulation comprising: the antibody or antigen-binding fragment thereof of claim 5, and a pharmaceutically acceptable excipient.

30. A pharmaceutical formulation comprising: the antibody or antigen-binding fragment thereof of claim 6, and a pharmaceutically acceptable excipient.

31. A pharmaceutical formulation comprising: the antibody or antigen-binding fragment thereof of claim 7, and a pharmaceutically acceptable excipient.

32. A pharmaceutical formulation comprising: the antibody or antigen-binding fragment thereof of claim 8, and a pharmaceutically acceptable excipient.

* * * * *

UNITED STATES PATENT AND TRADEMARK OFFICE
CERTIFICATE OF CORRECTION

PATENT NO. : 10,400,018 B2
APPLICATION NO. : 15/117268
DATED : September 3, 2019
INVENTOR(S) : Irene Griswold-Prenner, Graham Parry and Tony SangYoung Byun Page 1 of 1

It is certified that error appears in the above-identified patent and that said Letters Patent is hereby corrected as shown below:

In the Claims

Column 172, Claim 2:
Line 54, delete "b) a)" and insert -- b) --.

Column 173, Claim 7:
Line 42, delete "(c) (b)" and insert -- (c) --.

Column 173, Claim 8:
Line 56, delete "c) b)" and insert -- c) --.

Signed and Sealed this
Nineteenth Day of November, 2019

Andrei Iancu
*Director of the United States Patent and Trademark Office*